(12) United States Patent
Gao et al.

(10) Patent No.: US 10,193,070 B2
(45) Date of Patent: Jan. 29, 2019

(54) ELECTROACTIVE MATERIALS

(71) Applicant: E I DU PONT DE NEMOURS AND COMPANY, Wilmington, DE (US)

(72) Inventors: Weiying Gao, Landenberg, PA (US); Michael Henry Howard, Jr., Montchanin, DE (US); Viacheslav V. Diev, Wilmington, DE (US); Weishi Wu, Landenberg, PA (US); Hong Meng, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 15/518,854

(22) PCT Filed: Oct. 20, 2015

(86) PCT No.: PCT/US2015/056364
§ 371 (c)(1),
(2) Date: Apr. 13, 2017

(87) PCT Pub. No.: WO2016/069321
PCT Pub. Date: May 6, 2016

(65) Prior Publication Data
US 2017/0229654 A1 Aug. 10, 2017

Related U.S. Application Data

(60) Provisional application No. 62/073,424, filed on Oct. 31, 2014, provisional application No. 62/073,561, (Continued)

(51) Int. Cl.
*C07D 487/06* (2006.01)
*C07D 493/06* (2006.01)
(Continued)

(52) U.S. Cl.
CPC ........ *H01L 51/0035* (2013.01); *C07D 487/06* (2013.01); *C07D 493/06* (2013.01);
(Continued)

(58) Field of Classification Search
CPC ... C07D 487/06; C07D 493/06; C07D 495/06
See application file for complete search history.

(56) References Cited

U.S. PATENT DOCUMENTS

| | | |
|---|---|---|
| 6,670,645 B2 | 12/2003 | Grushin et al. |
| 2004/0102577 A1 | 5/2004 | Hsu et al. |

(Continued)

FOREIGN PATENT DOCUMENTS

| | | |
|---|---|---|
| WO | 2003/008424 A1 | 1/2003 |
| WO | 2003/040257 A1 | 5/2003 |

(Continued)

OTHER PUBLICATIONS

Sawada, et al. Document No. 156:547436, retrieved from STN; Apr. 19, 2012 entered in STN.*
(Continued)

*Primary Examiner* — Shawquia Jackson

(57) ABSTRACT

There is disclosed a compound having Formula I, Formula II, Formula III, Formula VIII, Formula IX, or Formula X (Continued)

-continued

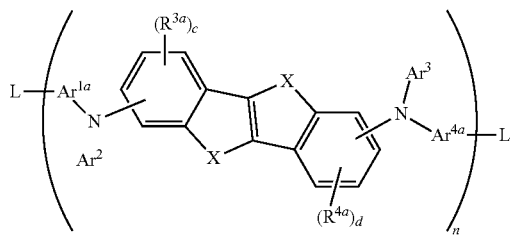
(X)

The variables are described in detail in the application.

17 Claims, 2 Drawing Sheets

Related U.S. Application Data filed on Oct. 31, 2014, provisional application No. 62/073,543, filed on Oct. 31, 2014, provisional application No. 62/073,408, filed on Oct. 31, 2014.

(51) Int. Cl.

| | | |
|---|---|---|
| *C07D 495/06* | (2006.01) | |
| *H01L 51/00* | (2006.01) | |
| *C09K 11/02* | (2006.01) | |
| *H01L 51/50* | (2006.01) | |
| *H01L 51/52* | (2006.01) | |
| *C08G 73/02* | (2006.01) | |
| *C07D 517/06* | (2006.01) | |

(52) U.S. Cl.
CPC ......... *C07D 495/06* (2013.01); *C07D 517/06* (2013.01); *C08G 73/026* (2013.01); *C09K 11/025* (2013.01); *H01L 51/006* (2013.01); *H01L 51/0052* (2013.01); *H01L 51/0058* (2013.01); *H01L 51/0059* (2013.01); *H01L 51/0081* (2013.01); *H01L 51/5016* (2013.01); *H01L 51/5024* (2013.01); *H01L 51/5064* (2013.01); *H01L 51/5206* (2013.01); *H01L 51/5221* (2013.01); *C09K 2211/1007* (2013.01); *H01L 2251/308* (2013.01)

(56) References Cited

U.S. PATENT DOCUMENTS

| | | |
|---|---|---|
| 2004/0127637 A1 | 7/2004 | Hsu et al. |
| 2005/0184287 A1 | 8/2005 | Herron et al. |
| 2005/0205860 A1 | 9/2005 | Hsu et al. |
| 2013/0082251 A1 | 4/2013 | Park et al. |
| 2013/0193429 A1* | 8/2013 | Sawada ................ C07D 487/04 257/40 |

FOREIGN PATENT DOCUMENTS

| | | |
|---|---|---|
| WO | 2003/063555 A1 | 7/2003 |
| WO | 2003/091688 A2 | 11/2003 |
| WO | 2004/016710 A1 | 2/2004 |
| WO | 2005/052027 A1 | 6/2005 |
| WO | 2007/145979 A3 | 4/2008 |
| WO | 2009/018009 A1 | 2/2009 |
| WO | 2015/089304 A1 | 6/2015 |

OTHER PUBLICATIONS

Yoo, et al. Document No. 158:143512, retrieved from STN; Dec. 14, 2012.*
Sawada, et al. Document No. 156:465908, retrieved from STN; Mar. 22, 2012.*
Ahn, et al. Document No. 155:628879, retrieved from STN; Oct. 27, 2011.*
Chen, et al. Document No. 155:656341, retrieved from STN; 2011.*
Nakatsuka. Document No. 150:342314, retrieved from STN; Mar. 12, 2009.*
Ito. Document No. 118:180013, retrieved from STN; Nov. 18, 1992.*
Van der Auweraer, et al. Document No. 106:92869; retrieved from STN; 1987.*
Wang, Y., Kirk-Othmer Encyclopedia of Chemical Technology, Fourth Edition, 1996, vol. 18, pp. 837-860 (Book Not Included).
PCT International Search Report for Application No. PCT/US2015/056364; Chang, Bong Ho, Authorized Officer; ISA/KR; Jul. 1, 2016.
Jin et al., "New Conjugated Polymer Based on Dihydroindoloindole for LEDs," Bull. Korean Chem. Doc., 2006, vol. 27, No. 7, pp. 1043-1047.
Gustafsson, G. et al. "Flexible light-emitting diodes made from soluble conducting polymers" Letters to Nature, vol. 357, Jun. 11, 1992, pp. 477-479.
CRC Handbook of Chemistry & Physics, 81st Edition, (2000-2001) (Book Not Included).

* cited by examiner

ELECTROACTIVE MATERIALS

RELATED APPLICATION DATA

This application claims priority under 35 U.S.C. § 119(e) from U.S. Provisional Application Nos. 62/073,408, 62/073,424, 62/073,543, and 62/073,561, which all were filed on Oct. 31, 2014, and which are incorporated by reference herein in their entirety.

BACKGROUND INFORMATION

Field of the Disclosure

The present disclosure relates to novel electroactive compounds.

The disclosure further relates to electronic devices having at least one layer comprising such an electroactive compound.

Description of the Related Art

In organic electronic devices, such as organic light emitting diodes ("OLED"), that make up OLED displays, one or more organic electroactive layers are sandwiched between two electrical contact layers. In an OLED at least one organic electroactive layer emits light through the light-transmitting electrical contact layer upon application of a voltage across the electrical contact layers.

It is well known to use organic electroluminescent compounds as the light-emitting component in light-emitting diodes. Simple organic molecules, conjugated polymers, and organometallic complexes have been used.

Devices that use electroluminescent materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode.

There is a continuing need for electroactive materials for use in electronic devices.

SUMMARY

There is provided a compound having Formula I, Formula II, Formula III, Formula VIII, Formula IX, or Formula X

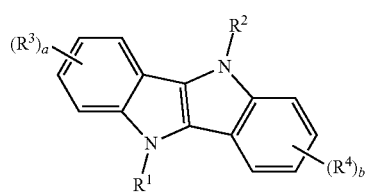

(I)

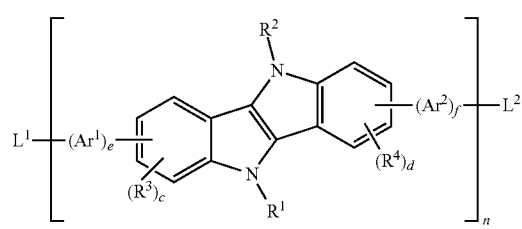

(II)

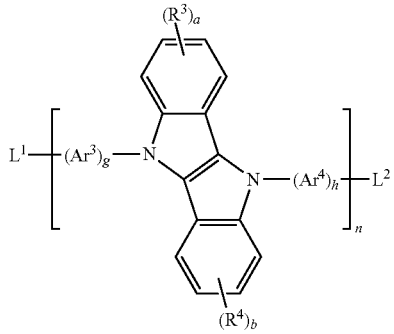

(III)

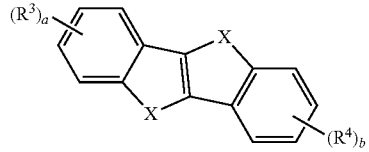

(VIII)

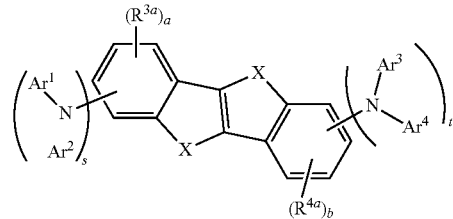

(IX)

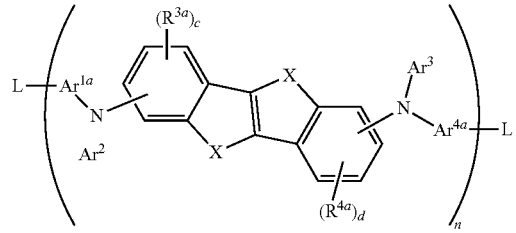

(X)

wherein:
Ar$^1$-Ar$^4$, Ar$^{1a}$ and Ar$^{4a}$ are the same or different and are selected from the group consisting of aryl groups, heteroaryl groups, substituted derivatives thereof, and deuterated analogs thereof;

R$^1$ and R$^2$ are the same or different at each occurrence and are selected from the group consisting of alkyl, silyl, germyl, aryl, heteroaryl, and deuterated analogs thereof;

R$^3$ and R$^4$ are the same or different at each occurrence and are selected from the group consisting of D, alkyl, alkoxy, silyl, siloxy, siloxane, germyl, aryl, alkenylaryl, aryloxy, heteroaryl, diarylamino, deuterated alkyl, deuterated alkoxy, deuterated silyl, deuterated siloxy, deuterated siloxane, deuterated germyl, deuterated aryl, deuterated alkenylaryl, deuterated aryloxy, deuterated heteroaryl, and deuterated diarylamino;

R$^{3a}$ and R$^{4a}$ are the same or different at each occurrence and are selected from the group consisting of D, alkyl, alkoxy, silyl, siloxy, siloxane, germyl, aryl, alkenylaryl, aryloxy, heteroaryl, deuterated alkyl, deuterated alkoxy, deuterated silyl, deuterated siloxy, deuterated siloxane, deuterated germyl, deuterated aryl, deuterated alkenylaryl, deuterated aryloxy, and deuterated heteroaryl;

L, L$^1$ and L$^2$ are the same or different at each occurrence and are selected from the group consisting of H, D, halogen, aryl, arylamino, crosslinkable groups, deuterated aryl, deuterated arylamino, and deuterated crosslinkable groups;

X is O, S, or Se;

a and b are the same or different and are an integer from 0-4;

c and d are the same or different and are an integer from 0-3;

e and f are the same or different and are 0 or 1;

g and h are the same or different and are 0 or 1, with the proviso that g+h>0;

n is an integer greater than 0; and s and t are 0 or 1, with the proviso that s+t>0 and when s=1, a is 0-3, and when t=1, b is 0-3.

There is also provided a copolymer having at least one monomeric unit of Formula IV, Formula V, or Formula XI

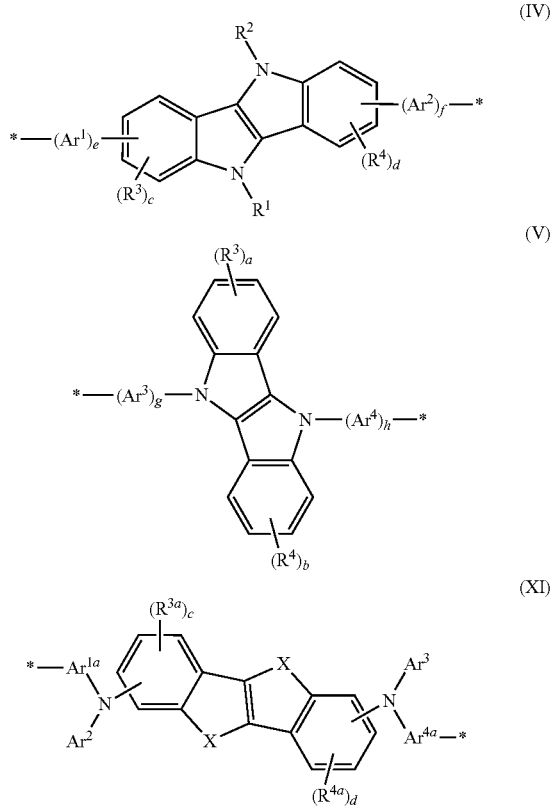

where * represents a point of attachment in the copolymer and Ar$^1$-Ar$^4$, Ar$^{1a}$, Ar$^{4a}$, R$^1$-R$^4$, R$^{3a}$, R$^{4a}$, a-h and n are as defined above.

There is also provided a copolymer having Formula VI, Formula VII, or Formula XII

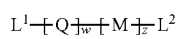 Formula VI

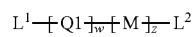 Formula VII

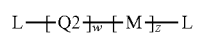 Formula XII where:

M is a conjugated moiety;

Q is a monomeric unit having Formula IV;

Q1 is a monomeric unit having Formula V;

Q2 is a monomeric unit having Formula XI;

w and z represent non-zero mole fractions such that w+z=1;

and L, L$^1$ and L$^2$ are as defined above.

There is also provided an electronic device having at least one layer comprising a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
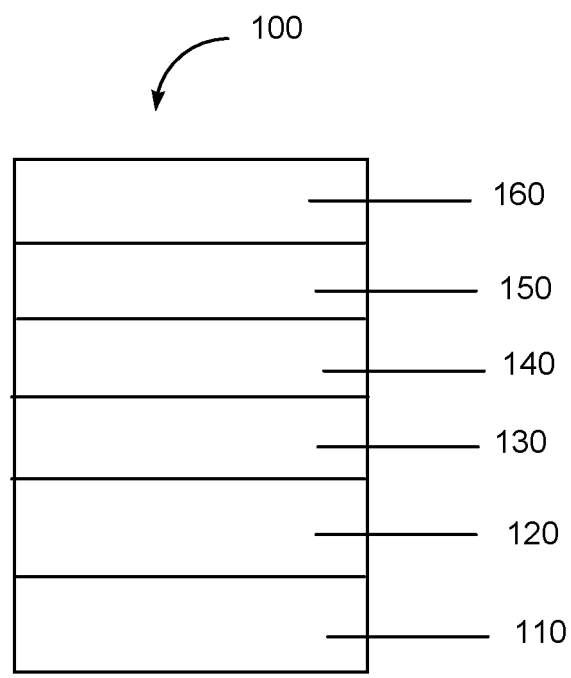
FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

There is provided a compound having Formula I, Formula II, Formula III, Formula VIII, Formula IX, or Formula X, a copolymer having at least one monomeric unit of Formula IV, Formula V, or Formula XI, and a copolymer having Formula VI, Formula VII, or Formula XII, as described in detail below.

There is also provided an electronic device having at least one layer comprising a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Compound of Formula I; the Compound of Formula II or Formula III; the Copolymer Having at Least one Unit of Formula IV or Formula V and the Copolymer of Formula VI or Formula VII; the Compound of Formula VIII; the Compound of Formula IX or Formula X; the Copolymer Having at Least one Unit of Formula XI and the Copolymer of Formula XII; the Electronic Device; and finally Examples.

1. Definitions and Clarification of Terms

Before addressing details of embodiments described below, some terms are defined or clarified.

As used herein, the term "alkyl" includes branched and straight-chain saturated aliphatic hydrocarbon groups. Unless otherwise indicated, the term is also intended to include cyclic groups. Examples of alkyl groups include methyl, ethyl, propyl, isopropyl, isobutyl, secbutyl, tertbutyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "aromatic compound" is intended to mean an organic compound comprising at least one unsaturated cyclic group having 4n+2 delocalized pi electrons. The term is intended to encompass both aromatic compounds having only carbon and hydrogen atoms, and heteroaromatic compounds wherein one or more of the carbon atoms within the cyclic group has been replaced by another atom, such as nitrogen, oxygen, sulfur, or the like.

The term "aryl" or "aryl group" means a moiety derived from an aromatic compound. A group "derived from" a compound, indicates the radical formed by removal of one or more H or D. The aryl group may be a single ring (monocyclic) or multiple rings (bicyclic, or more) fused together or linked covalently. Examples of aryl moieties include, but are not limited to, phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. In some embodiments, aryl groups have 6 to 60 ring carbon atoms; in some embodiments, 6 to 30 ring carbon atoms. The term is intended to include heteroaryl groups. Heteroaryl groups may have from 4-50 ring carbon atoms; in some embodiments, 4-30 ring carbon atoms.

The term "alkoxy" is intended to mean the group —OR, where R is alkyl.

The term "aryloxy" is intended to mean the group —OR, where R is aryl.

Unless otherwise indicated, all groups can be substituted or unsubstituted. An optionally substituted group, such as, but not limited to, alkyl or aryl, may be substituted with one or more substituents which may be the same or different. Suitable substituents include D, alkyl, aryl, nitro, cyano, —N(R')(R"), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxy, siloxane, germyl, thioalkoxy, —S(O)$_2$—, —C(=O)—N(R')(R"), (R')(R")N-alkyl, (R')(R")N-alkoxyalkyl, (R')(R")N-alkylaryloxyalkyl, —S(O)$_s$-aryl (where s=0-2) or —S(O)$_s$-heteroaryl (where s=0-2). Each R' and R" is independently an optionally substituted alkyl, cycloalkyl, or aryl group. R' and R", together with the nitrogen atom to which they are bound, can form a ring system in certain embodiments. Substituents may also be crosslinking groups. Any of the preceding groups with available hydrogens, may also be deuterated.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "CN" refers to the cyano group, —C≡N.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "deuterated" is intended to mean that at least one hydrogen ("H") has been replaced by deuterium ("D"). The term "deuterated analog" refers to a structural analog of a compound or group in which one or more available hydrogens have been replaced with deuterium. In a deuterated compound or deuterated analog, the deuterium is present in at least 100 times the natural abundance level.

The term "electroactive" as it refers to a layer or a material, is intended to indicate a layer or material which electronically facilitates the operation of the device. Examples of electroactive materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The prefix "fluoro" is intended to indicate that one or more hydrogens in a group has been replaced with fluorine.

The term "FWHM" stands for "full width half maximum" and is intended to mean the width of the emission profile at half the maximum intensity.

The term "germyl" refers to the group R$_3$Ge—, where R is the same or different at each occurrence and is H, D, C1-20 alkyl, deuterated alkyl, fluoroalkyl, aryl, or deuterated aryl.

The prefix "hetero" indicates that one or more carbon atoms has been replaced with a different atom. In some embodiments, the heteroatom is O, N, S, or combinations thereof.

The term "fused ring core" indicates the structure below, where X=O, S, or Se. The positions on the fused ring core are numbered as follows:

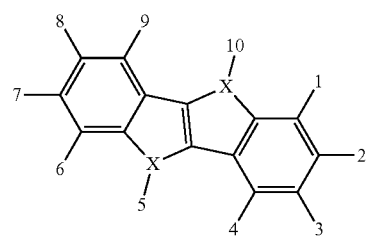

The term "indoloindole" or "indoloindole core" indicates the structure shown below. The positions on the indoloindole core are numbered as follows:

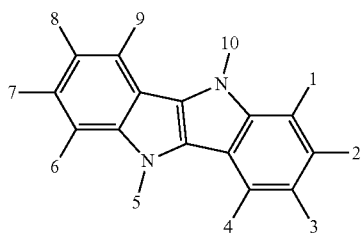

The term "liquid composition" is intended to mean a liquid medium in which a material is dissolved to form a solution, a liquid medium in which a material is dispersed to form a dispersion, or a liquid medium in which a material is suspended to form a suspension or an emulsion.

The term "photoactive" refers to a material or layer that emits light when activated by an applied voltage (such as in a light emitting diode or chemical cell), that emits light after the absorption of photons (such as in down-converting phosphor devices), or that responds to radiant energy and generates a signal with or without an applied bias voltage (such as in a photodetector or a photovoltaic cell).

The term "siloxane" refers to the group $R_3SiOR_2Si—$, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

The term "siloxy" refers to the group $R_3SiO—$, where R is the same or different at each occurrence and is H, D, C1-20 alkyl, deuterated alkyl, fluoroalkyl, aryl, or deuterated aryl.

The term "silyl" refers to the group $R_3Si—$, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

In a structure where a substituent bond passes through one or more rings as shown below,

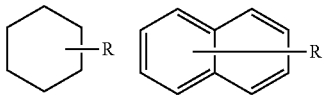

it is meant that the substituent R may be bonded at any available position on the one or more rings.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). Exemplary adjacent R groups are shown below:

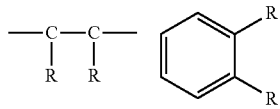

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics,* 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

In some embodiments, the compound having Formula I, Formula II, Formula III, Formula VIII, Formula IX, or Formula X, the copolymer having at least one monomeric unit of Formula IV, Formula V, or Formula XI, or the copolymer having Formula VI, Formula VII, or Formula XII is deuterated. In some embodiments, the compound is at least 10% deuterated. By "% deuterated" or "% deuteration" is meant the ratio of deuterons to the sum of protons plus deuterons, expressed as a percentage. In some embodiments, the compound, polymer or copolymer is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

The compounds, polymers and copolymers described herein can be formed into layers for electronic devices. The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous liquid deposition techniques, include but are not limited to, spin coating, gravure coating, curtain coating, dip coating, slot-die coating, spray coating, and continuous nozzle coating. Discontinuous liquid deposition techniques include, but are not limited to, ink jet printing, gravure printing, and screen printing.

In some embodiments, the compounds, polymers and copolymers described herein can be used as hole transport materials in devices.

In some embodiments, the compounds, polymers and copolymers described herein are electroluminescent and can be used as emissive materials in devices.

In some embodiments, the compounds, polymers and copolymers described herein can be used as hosts for photoactive dopants.

In some embodiments, the compounds, polymers and copolymers described herein can be used as hosts for photoactive dopants in combination with one or more additional hosts.

In some embodiments, the compounds, polymers and copolymers described herein can be used as electron transport materials in devices.

In some embodiments, the compounds, polymers and copolymers described herein have a photoluminescence emission profile with a FWHM that is less than 75 nm; in some embodiments, less than 60 nm; in some embodiments, less than 50 nm. This is advantageous for display devices for producing more saturated color.

2. Compound Having Formula I

In some embodiments, the new compound is an electroactive compound having Formula I

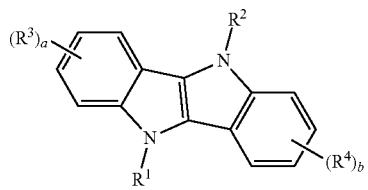

(I)

wherein:
$R^1$ and $R^2$ are the same or different at each occurrence and are selected from the group consisting of alkyl, silyl, germyl, aryl, heteroaryl, and deuterated analogs thereof;
$R^3$ and $R^4$ are the same or different at each occurrence and are selected from the group consisting of D, alkyl, alkoxy, silyl, siloxy, siloxane, germyl, aryl, alkenylaryl, aryloxy, heteroaryl, diarylamino, deuterated alkyl, deuterated alkoxy, deuterated silyl, deuterated siloxy, deuterated siloxane, deuterated germyl, deuterated aryl, deuterated alkenylaryl, deuterated aryloxy, deuterated heteroaryl, and deuterated diarylamino; and a and b are the same or different and are an integer from 0-4.

In some embodiments of Formula I, $R^1=R^2$.
In some embodiments of Formula I, $R^1 \neq R^2$.
In some embodiments of Formula I, $R^3=R^4$.
In some embodiments of Formula I, $R^3 \neq R^4$.
In some embodiments of Formula I, $R^1$ is an alkyl group or deuterated alkyl group having 1-30 carbons; in some embodiments, 3-20 carbons; in some embodiments, 5-20 carbons.

In some embodiments of Formula I, $R^1$ is a hydrocarbon aryl group having 6-36 ring carbons. The hydrocarbon aryl group can include one or more single ring groups bonded together, one or more fused rings, or combinations thereof.

In some embodiments of Formula I, $R^1$ has no heteroaromatic groups.

In some embodiments of Formula I, $R^1$ has Formula a

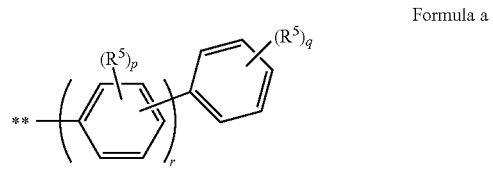

Formula a where:
$R^5$ is the same or different at each occurrence and is selected from the group consisting of D, alkyl, alkoxy, siloxane, silyl, germyl, deuterated alkyl, deuterated alkoxy, deuterated siloxane, deuterated silyl, and deuterated germyl, where adjacent $R^5$ groups can be joined together to form an fused aromatic ring or a deuterated fused aromatic ring;
p is the same or different at each occurrence and is an integer from 0-4;
q is an integer from 0-5;
r is an integer from 1 to 5; and
** represents a point of attachment to N.

In some embodiments of Formula I, $R^1$ has Formula b

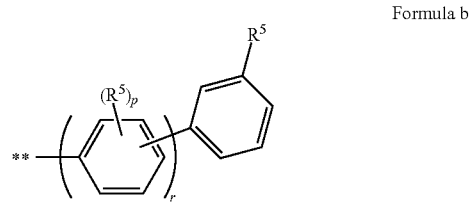

Formula b where $R^5$, p, r and ** are as in Formula a.

In some embodiments of Formula I, $R^1$ is selected from the group consisting of phenyl, naphthyl, anthracenyl, a group derived from benz[de]anthracene, Formula a, and deuterated analogs thereof.

In some embodiments of Formula I, $R^1$ is a heteroaryl group having at least one ring atom which is selected from the group consisting of N, O, and S.

In some embodiments of Formula I, $R^1$ is an N-heteroaryl group, having at least one ring atom that is N.

In some embodiments, the N-heteroaryl is derived from a compound selected from the group consisting of pyrrole, pyridine, pyrimidine, carbazole, imidazole, benzimidazole, imidazolobenzimidazole, triazole, benzotriazole, triazolopyridine, indole, indolocarbazole, phenanthroline, quinoline, isoquinoline, quinoxaline, substituted derivatives thereof, and deuterated analogs thereof.

In some embodiments, the N-heteroaryl is a carbazole or deuterated carbazole.

In some embodiments, the N-heteroaryl is a carbazole or deuterated carbazole having formula Cz-1:

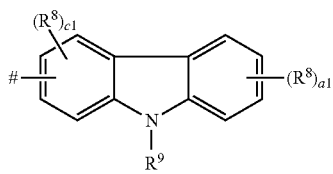

Cz-1 wherein:
$R^8$ is the same or different at each occurrence and is selected from the group consisting of D, alkyl, silyl, germyl, aryl, deuterated alkyl, deuterated silyl, deuterated germyl, and deuterated aryl;
$R^9$ is selected from the group consisting of aryl and deuterated aryl;
c1 is an integer of 0-3;
a1 is an integer of 0-4; and
# represents a point of attachment.

In some embodiments, the N-heteroaryl is a carbazole or deuterated carbazole having formula Cz-2:

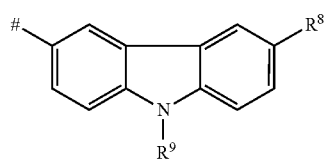

Cz-2 where $R^8$, $R^9$ and # are as defined above for Cz-1.

In some embodiments, the N-heteroaryl which is a carbazole or deuterated carbazole having formula Cz-3:

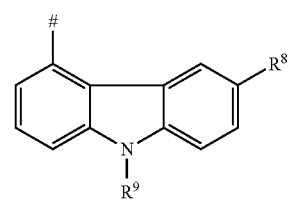

Cz-3 where $R^8$, $R^9$ and # are as defined above for Cz-1.

In some embodiments, the N-heteroaryl is a benzimidazole or deuterated benzimidazole having formula Bzl-1:

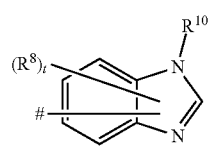

Bzl-1 where $R^{10}$ is selected from the group consisting of alkyl, aryl, and deuterated analogs thereof; $R^8$ and # are as defined above for Cz-1.

In some embodiments, the N-heteroaryl is a benzimidazole or deuterated benzimidazole having formula Bzl-2:

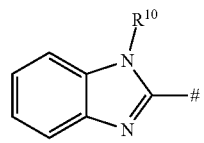

Bzl-2 where $R^{10}$ and # are as defined above for Bzl-1.

In some embodiments of Formula I, $R^1$ is an O-heteroaryl having at least one ring atom that is O.

In some embodiments, the O-heteroaryl is derived from a compound selected from the group consisting of furan, benzofuran, dibenzofuran, substituted derivatives thereof, and deuterated analogs thereof.

In some embodiments, the O-heteroaryl is a dibenzofuran or deuterated dibenzofuran.

In some embodiments, the O-heteroaryl is a dibenzofuran or deuterated dibenzofuran having formula DBF-1:

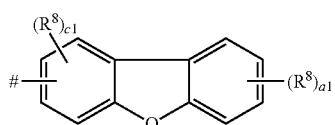

DBF-1 where a1, c1, $R^8$ and # are as defined above for Cz-1.

In some embodiments, the O-heteroaryl is a dibenzofuran or deuterated dibenzofuran having formula DBF-2:

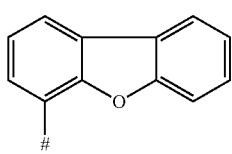

DBF-2 where # represents the point of attachment.

In some embodiments, the O-heteroaryl is a dibenzofuran or deuterated dibenzofuran having formula DBF-3:

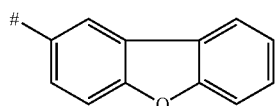

DBF-3 where # represents the point of attachment.

In some embodiments of Formula I, $R^1$ is an S-heteroaryl having at least one ring atom which is S.

In some embodiments, the S-heteroaryl is derived from a compound selected form the group consisting of thiophene, benzothiophene, dibenzothiophene, substituted derivatives thereof, and deuterated analogs thereof.

In some embodiments, the S-heteroaryl is a dibenzothiophene or deuterated dibenzothiophene.

In some embodiments, the S-heteroaryl is a dibenzothiophene or deuterated dibenzothiophene having formula DBT-1

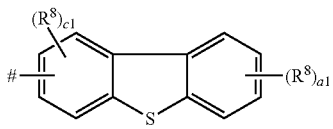

DBT-1 where a1, c1, $R^8$, and # are as defined above for Cz-1.

In some embodiments, the S-heteroaryl is a dibenzothiophene or deuterated dibenzothiophene having formula DBT-2:

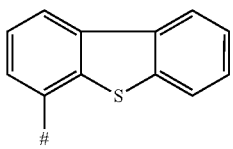

DBT-2 where # represents the point of attachment.

In some embodiments, the S-heteroaryl is a dibenzothiophene or deuterated dibenzothiophene having formula DBT-3:

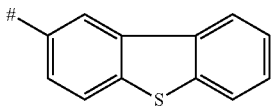

DBT-3 wherein # represents the point of attachment.

In some embodiments of Formula I, $R^1$ is an N,O-heteroaryl having at least one ring atom that is N and at least one ring atom that is O.

In some embodiments, the N,O-heteroaryl is derived from a compound selected from the group consisting of oxazole, benzoxazole, phenoxazine, substituted derivatives thereof, and deuterated analogs thereof.

In some embodiments, the N,O-heteroaryl is a benzoxazole or deuterated benzoxazole having formula BzO-1:

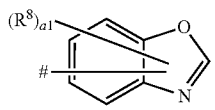

BzO-1 where a1, $R^8$ and # are as defined above for Cz-1.

In some embodiments, the N,O-heteroaryl is a benzoxazole or deuterated benzoxazole having formula BzO-2:

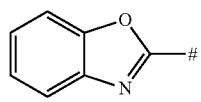

BzO-2 where # represents the point of attachment.

In some embodiments of Formula I, $R^1$ is an N,S-heteroaryl having at least one ring atom that is N and at least one ring atom that is S.

In some embodiments, the N,S-heteroaryl is derived from a compound selected from the group consisting of thiazole, benzothiazole, substituted derivatives thereof, and deuterated analogs thereof.

In some embodiments, the N,S-heteroaryl is a benzothiazole or deuterated benzothiazole having formula BT-1:

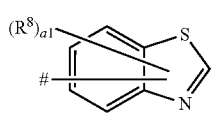

BT-1 where a1, $R^8$ and # are as defined above for Cz-1.

In some embodiments, the N,S-heteroaryl is a benzothiazole or deuterated benzothiazole having formula BT-2:

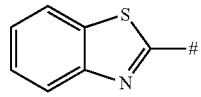

BT-2 where # represents the point of attachment.

In some embodiments of Formula I, $R^1$ is an aryl or heteroaryl group and has at least one substituent selected from the group consisting of D, alkyl, silyl, germyl, aryl, heteroaryl, deuterated alkyl, deuterated silyl, deuterated germyl, deuterated aryl, and deuterated heteroaryl.

All of the above-described embodiments for $R^1$ apply equally to $R^2$.

In some embodiments of Formula I, a=0.
In some embodiments of Formula I, a=1.
In some embodiments of Formula I, a=2.
In some embodiments of Formula I, a=3.
In some embodiments of Formula I, a=4.
In some embodiments of Formula I, a>0.

In some embodiments of Formula I, a>0 and at least one $R^3$ is at position 6 on the indoloindole core, as defined above.

In some embodiments of Formula I, a>0 and at least one $R^3$ is at position 7 on the indoloindole core, as defined above.

In some embodiments of Formula I, a>0 and at least one $R^3$ is at position 8 on the indoloindole core, as defined above.

In some embodiments of Formula I, a>0 and at least one $R^3$ is at position 9 on the indoloindole core, as defined above.

In some embodiments of Formula I, a>0 and at least one $R^3$ is D.

In some embodiments of Formula I, a>0 and at least one $R^3$ is alkenylaryl or deuterated alkenylaryl.

In some embodiments, the alkenylaryl is selected from the group consisting of styryl, stilbenyl, substituted derivatives thereof, and deuterated analogs thereof.

In some embodiments of Formula I, a>0 and at least one $R^3$ is a hydrocarbon aryl group having 6-36 ring carbons. The hydrocarbon aryl group can include one or more single ring groups bonded together, one or more fused rings, or combinations thereof.

In some embodiments of Formula I, a>0 and at least one $R^3$ has no heteroaromatic groups.

In some embodiments of Formula I, a>0 and at least one $R^3$ has Formula a1

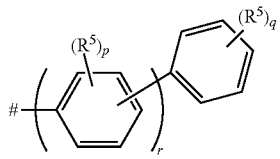

Formula a1 where:
R[5] is the same or different at each occurrence and is selected from the group consisting of D, alkyl, alkoxy, siloxane, silyl, germyl, deuterated alkyl, deuterated alkoxy, deuterated siloxane, deuterated silyl, and deuterated germyl, where adjacent R[5] groups can be joined together to form an fused aromatic ring or a deuterated fused aromatic ring;

p is the same or different at each occurrence and is an integer from 0-4;

q is an integer from 0-5;

r is an integer from 1 to 5; and # indicates a point of attachment.

In some embodiments of Formula I, a>0 and at least one R[3] has Formula b1

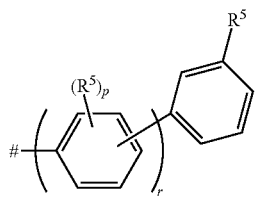

Formula b1 where R[5], p, r and # are as in Formula a1.

In some embodiments of Formula I, R[3] is selected from the group consisting of styryl, stilbenyl, phenyl, naphthyl, Formula a1, substituted derivatives thereof, and deuterated analogs thereof.

In some embodiments of Formula I, a>0 and at least one R[3] is a heteroaryl group having at least one ring atom which is selected from the group consisting of N, O, and S.

In some embodiments of Formula I, a>0 and at least one R[3] is an N-heteroaryl group, having at least one ring atom that is N.

In some embodiments of Formula I, a>0 and at least one R[3] is an O-heteroaryl having at least one ring atom that is O.

In some embodiments of Formula I, a>0 and at least one R[3] is an S-heteroaryl having at least one ring atom which is S.

In some embodiments of Formula I, a>0 and at least one R[3] is an N,O-heteroaryl having at least one ring atom that is N and at least one ring atom that is O.

In some embodiments of Formula I, a>0 and at least one R[3] is an N,S-heteroaryl having at least one ring atom that is N and at least one ring atom that is S.

In some embodiments of Formula I, a>0 and at least one R[3] is a diarylamino group or deuterated diarylamino group.

In some embodiments, the diarylamino group has Formula c

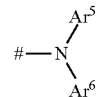

Formula c where:
Ar[5] and Ar[6] are the same or different and are selected from the group consisting of aryl groups, heteroaryl groups, substituted derivatives thereof, and deuterated analogs thereof; and # indicates a point of attachment.

In some embodiments of Formula c, Ar[5]=Ar[6].

In some embodiments of Formula c, Ar[5]≠Ar[6].

In some embodiments of Formula c, Ar[5] has Formula a, as defined above.

In some embodiments of Formula c, Ar[5] has Formula b, as defined above.

In some embodiments of Formula I, Ar[5] is selected from the group consisting of phenyl, naphthyl, Formula a, substituted derivatives thereof, and deuterated analogs thereof.

All of the above-described embodiments for Ar[5] apply equally to Ar[6].

In some embodiments of Formula I, a>0 and at least one R[3] has substituents selected from the group consisting of D, CN, alkyl, silyl, germyl, diarylamino, aryl, heteroaryl, deuterated alkyl, deuterated silyl, deuterated germyl, deuterated diarylamino, deuterated aryl, and deuterated heteroaryl.

In some embodiments of Formula I, b=0.
In some embodiments of Formula I, b=1.
In some embodiments of Formula I, b=2.
In some embodiments of Formula I, b=3.
In some embodiments of Formula I, b=4.
In some embodiments of Formula I, b>0.
In some embodiments of Formula I, b>0 and at least one R[4] is at position 1 on the indoloindole core, as defined above.
In some embodiments of Formula I, b>0 and at least one R[4] is at position 2 on the indoloindole core, as defined above.
In some embodiments of Formula I, b>0 and at least one R[4] is at position 3 on the indoloindole core, as defined above.
In some embodiments of Formula I, b>0 and at least one R[4] is at position 4 on the indoloindole core, as defined above.

All of the above-described embodiments for R[3] apply equally to R[4].

In some embodiments of Formula I, the compound has Formula I-a

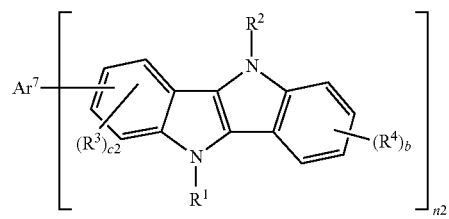

(I-a)

wherein:
Ar[7] is selected from the group consisting of aryl, heteroaryl, substituted derivatives thereof, and deuterated analogs thereof;

R[1] and R[2] are the same or different at each occurrence and are selected from the group consisting of alkyl, silyl, germyl, aryl, heteroaryl, and deuterated analogs thereof;

R³ and R⁴ are the same or different at each occurrence and are selected from the group consisting of D, alkyl, alkoxy, silyl, siloxy, siloxane, germyl, aryl, alkenylaryl, aryloxy, heteroaryl, diarylamino, deuterated alkyl, deuterated alkoxy, deuterated silyl, deuterated siloxy, deuterated siloxane, deuterated germyl, deuterated aryl, deuterated alkenylaryl, deuterated aryloxy, deuterated heteroaryl, and deuterated diarylamino; and b is an integer from 0-4;
c2 is an integer from 0-3; and
n2 is an integer from 2-6.

In some embodiments of Formula I-a, Ar⁷ is bonded to position 6 on the indoloindole core, as defined above.

In some embodiments of Formula I-a, Ar⁷ is bonded to position 7 on the indoloindole core, as defined above.

In some embodiments of Formula I-a, Ar⁷ is bonded to position 8 on the indoloindole core, as defined above.

In some embodiments of Formula I-a, Ar⁷ is bonded to position 9 on the indoloindole core, as defined above.

In some embodiments of Formula I-a, Ar⁷ is a hydrocarbon aryl group having 6-36 ring carbons. The hydrocarbon aryl group can include one or more single ring groups bonded together, one or more fused rings, or combinations thereof.

In some embodiments of Formula I-a, Ar⁷R¹ has no heteroaromatic groups.

In some embodiments of Formula I-a, Ar⁷ has Formula a1, as defined above.

In some embodiments of Formula I-a, Ar⁷ is a group derived from a compound selected from the group consisting of benzene, biphenyl, terphenyl, naphthalene, anthracene, fluorene, benzofluorene, benzanthracene, 7H-benz[de]anthracene, substituted derivatives thereof, and deuterated analogs thereof.

In some embodiments of Formula I-a, Ar⁷ is a heteroaryl group having at least one ring atom which is selected from the group consisting of N, O, and S, as described above.

In some embodiments of Formula I-a, Ar⁷ is an N-heteroaryl group, as described above.

In some embodiments of Formula I-a, Ar⁷ is an N,O-heteroaryl group, as described above.

In some embodiments of Formula I-a, Ar⁷ is an O-heteroaryl group, as described above.

In some embodiments of Formula I-a, Ar⁷ is an S-heteroaryl group, as described above.

In some embodiments of Formula I-a, Ar⁷ is an N,S-heteroaryl group as described above.

In some embodiments of Formula I-a, Ar⁷ is derived from a compound selected from the group consisting of pyrrole, pyridine, pyrimine, carbazole, imidazole, substituted derivatives thereof, and deuterated analogs thereof.

In some embodiments of Formula I-a, c2=0.
In some embodiments of Formula I-a, c2=1.
In some embodiments of Formula I-a, c2=2.
In some embodiments of Formula I-a, c2=3.
In some embodiments of Formula I-a, c2>0.
In some embodiments of Formula I-a, n2=2.
In some embodiments of Formula I-a, n2=3.
In some embodiments of Formula I-a, n2=4.
In some embodiments of Formula I-a, n2=5.
In some embodiments of Formula I-a, n2=6.

All of the above-described embodiments for R¹, R², R³, R⁴, and b in Formula I, apply equally to R¹, R², R³, R⁴, and b in Formula I-a.

In some embodiments of Formula I-a, b=c2=0, and n2=2.

Any of the above embodiments for Formula I can be combined with one or more of the other embodiments, so long as they are not mutually exclusive. For example, the embodiment in which a=2 can be combined with the embodiment in which a>0 and at least one R³ is D and the embodiment in which a>0 and at least one R³ has Formula a. The same is true for the other non-mutually-exclusive embodiments discussed above. The skilled person would understand which embodiments were mutually exclusive and would thus readily be able to determine the combinations of embodiments that are contemplated by the present application.

The compounds of Formula I can be made using any technique that will yield a C—C or C—N bond. A variety of such techniques are known, such as Suzuki, Yamamoto, Stille, and metal-catalyzed C—N couplings as well as metal catalyzed and oxidative direct arylation.

One way to prepare the indoloindole core (shown as F) is given below:

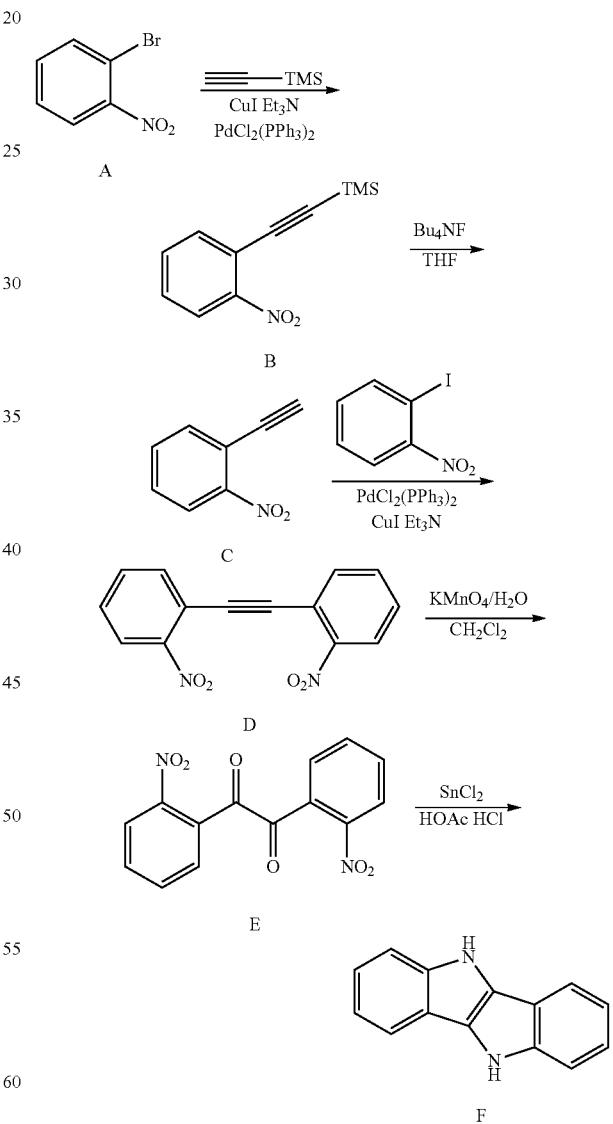

Deuterated compounds can be prepared in a similar manner using deuterated precursor materials or, more generally, by treating the non-deuterated compound with deuterated solvent, such as benzene-d6, in the presence of a Lewis acid H/D exchange catalyst, such as trifluoromethanesulfonic acid, aluminum trichloride or ethyl aluminum dichloride.
Exemplary preparations are given in the Examples.
Some non-limiting examples of compounds having Formula I are shown below.
Compound I-1
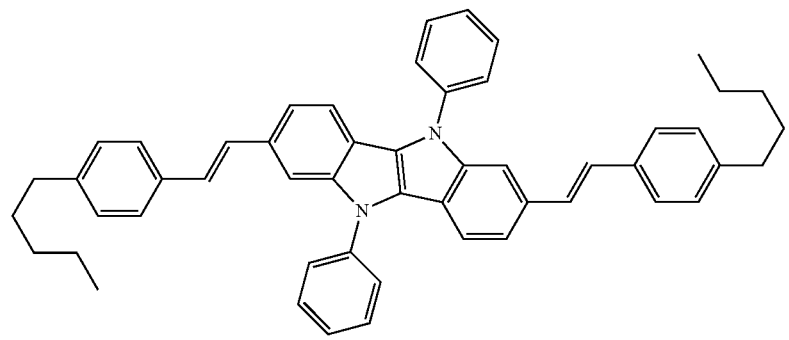
Compound I-2
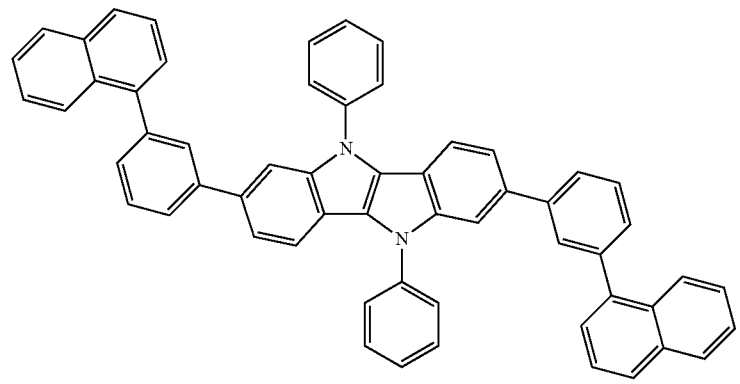
Compound I-3
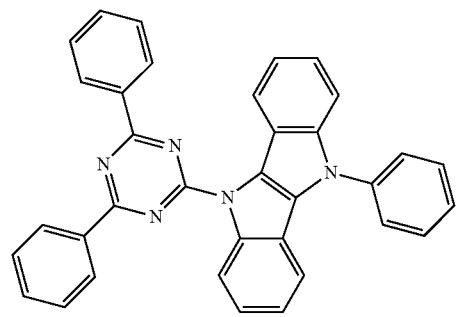
Compound I-4
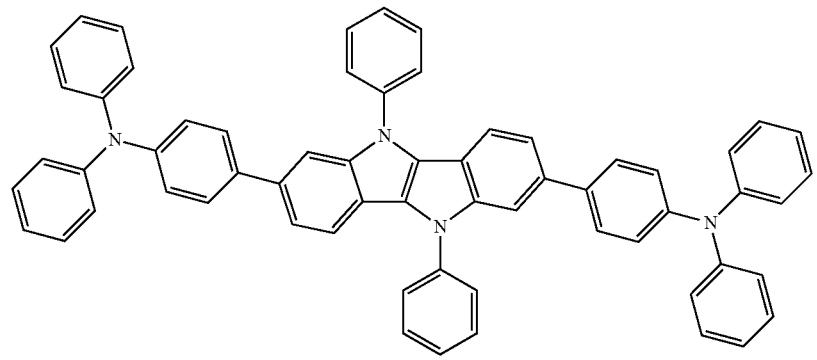

Compound I-5
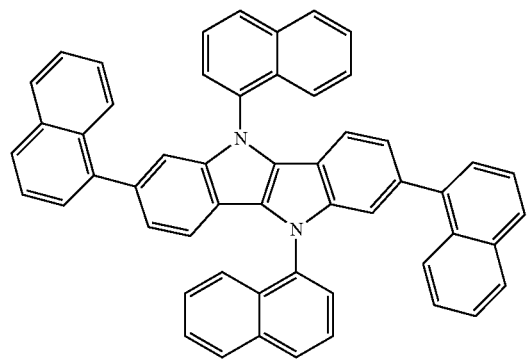
Compound I-6
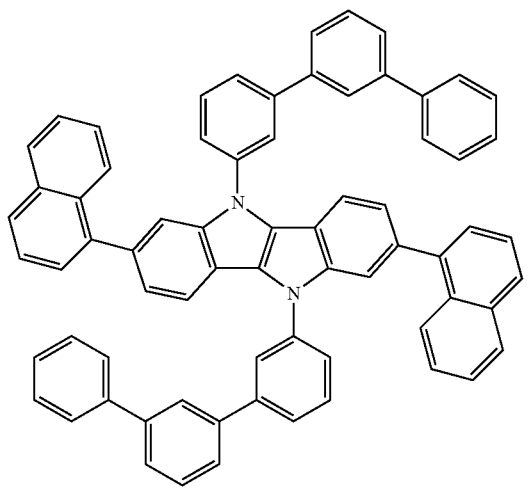
Compound I-7
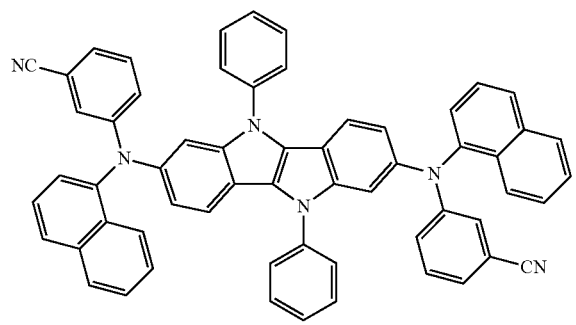
Compound I-8
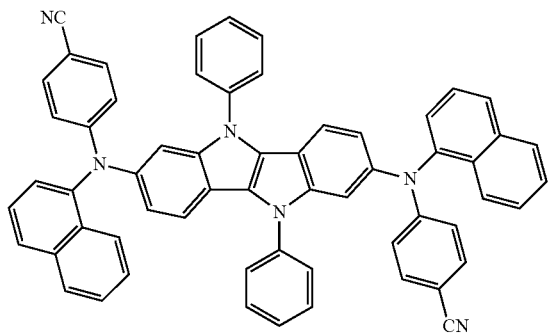
Compound I-9
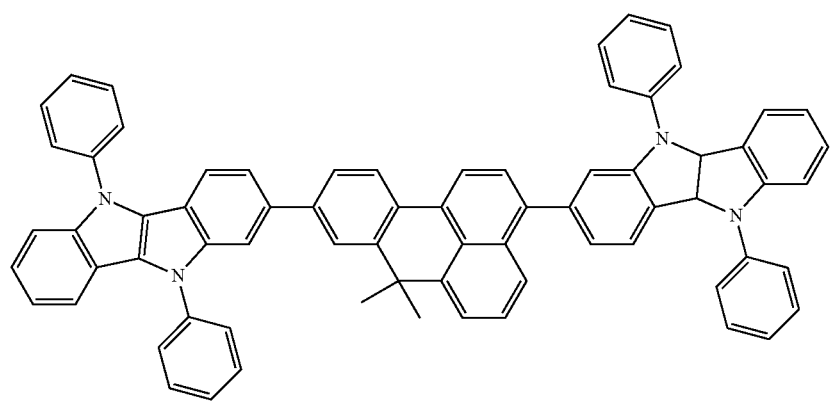
Compound I-10
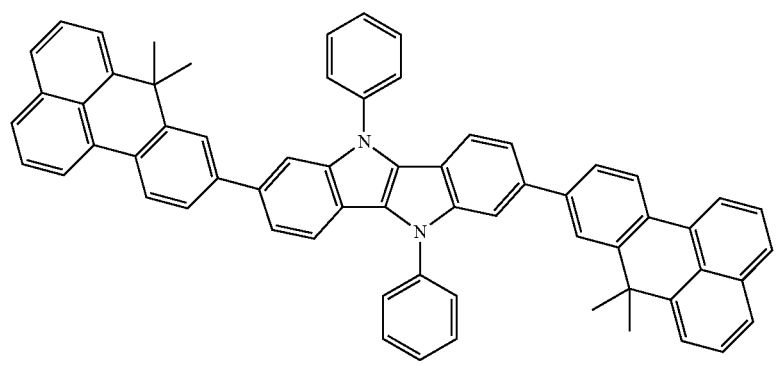

-continued
Compound I-11
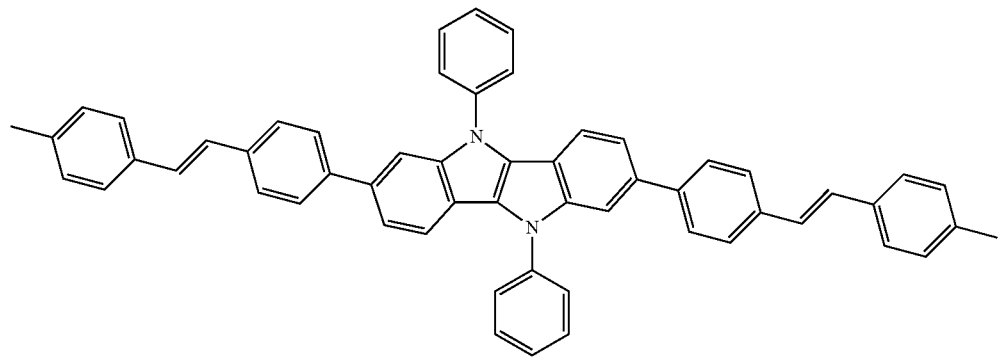
Compound I-12
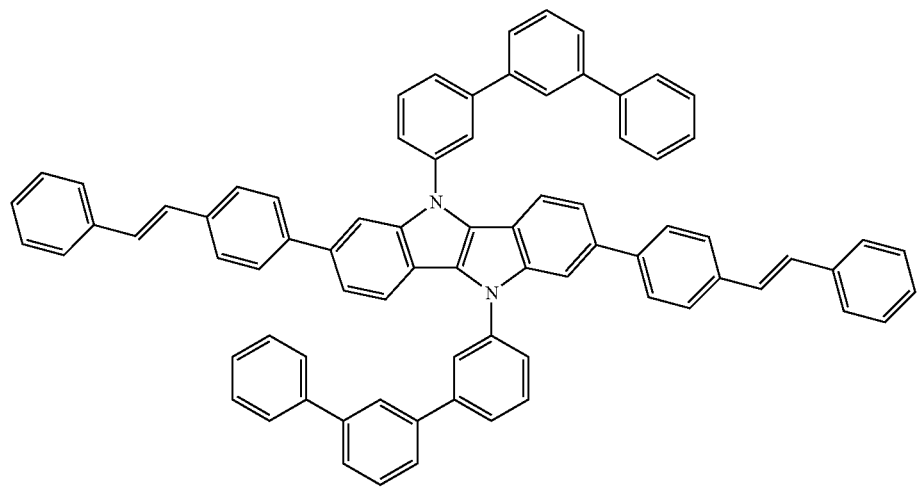
Compound I-13
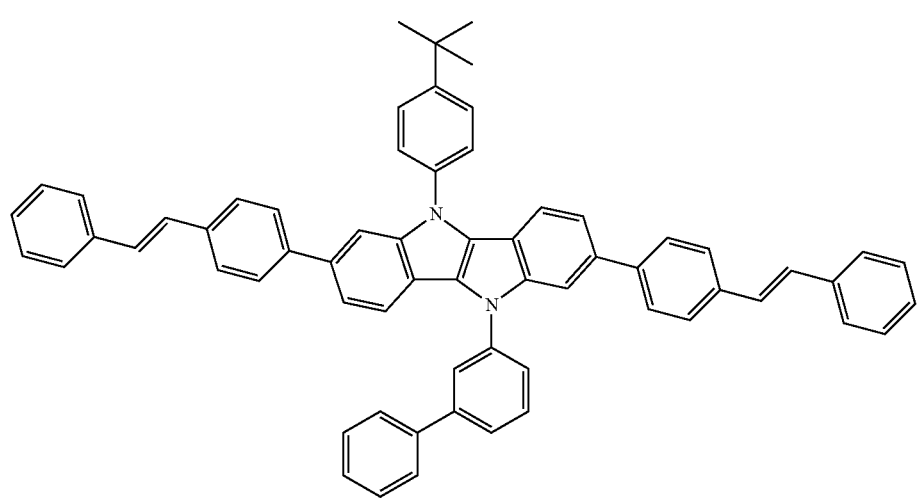

-continued
Compound I-14
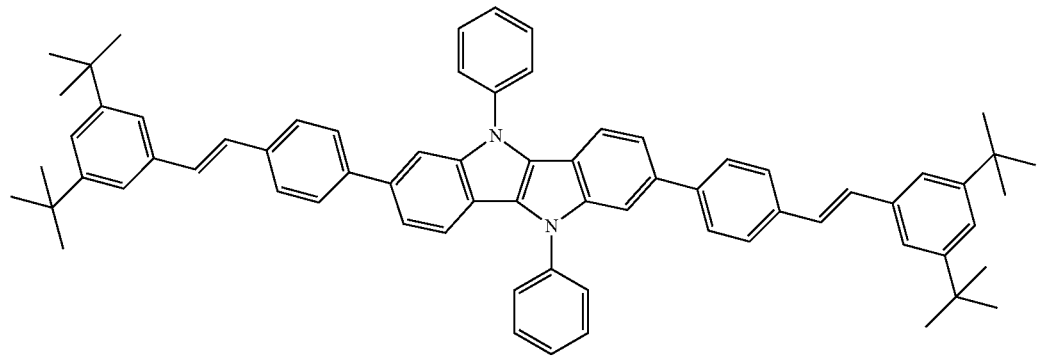
Compound I-15
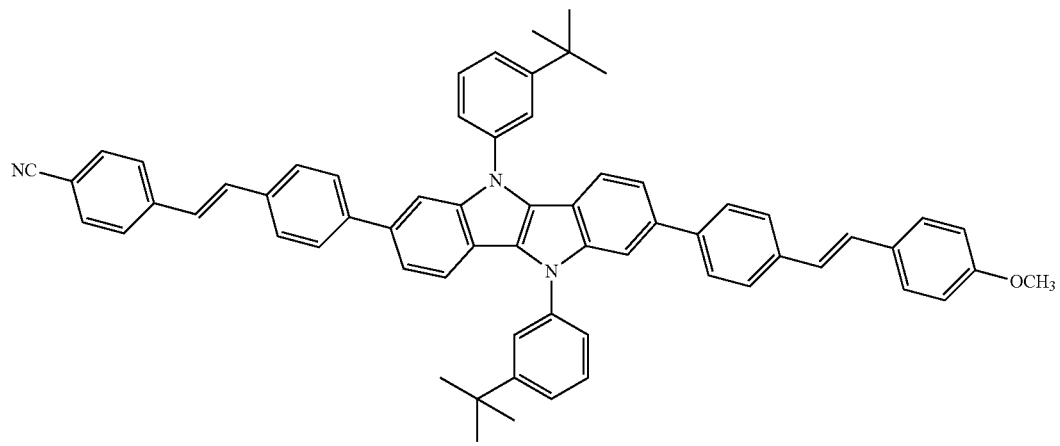
Compound I-16
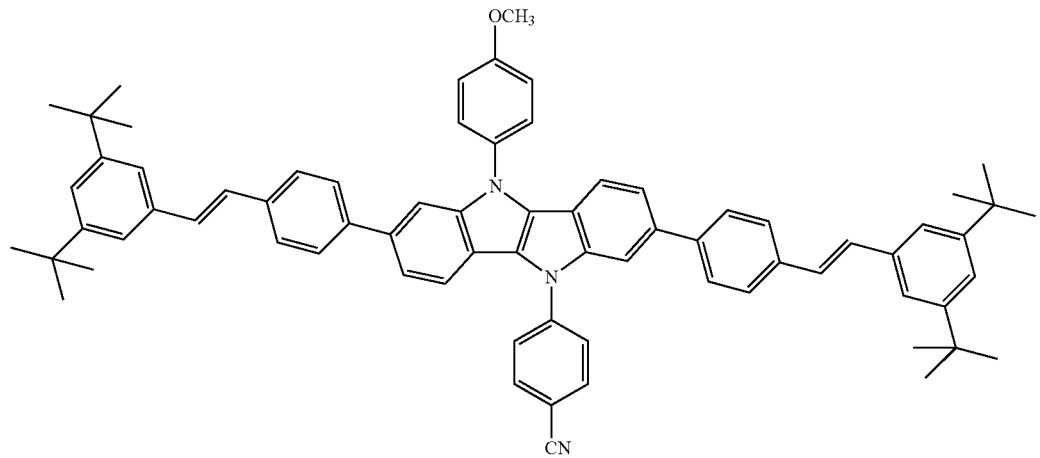
Compound I-17
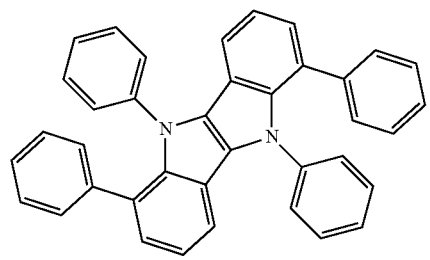

-continued
Compound I-18
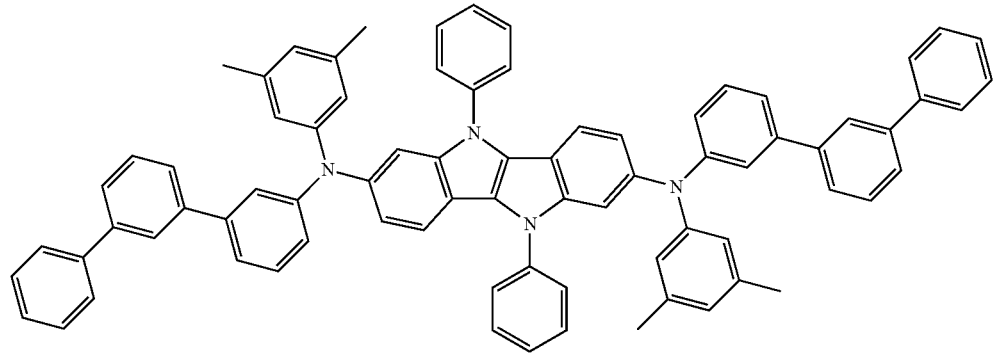
Compound I-19
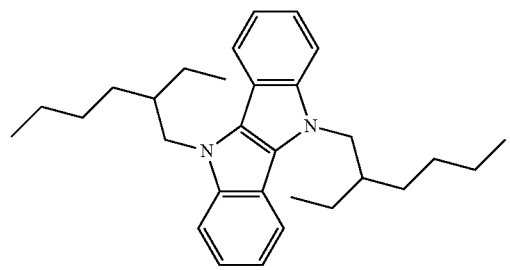
Compound I-20
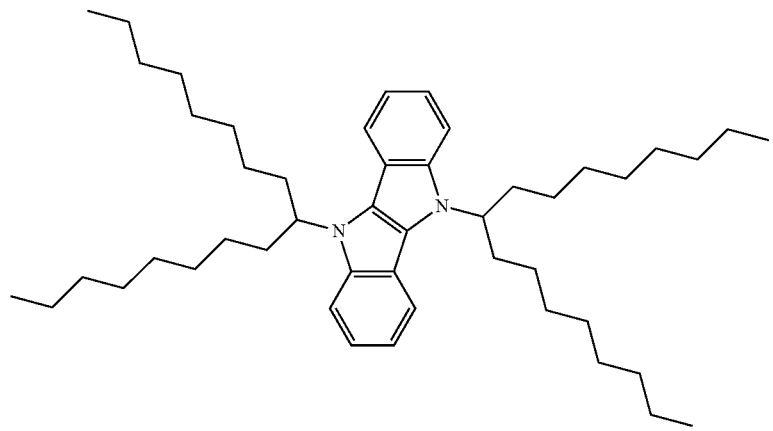
Compound I-21
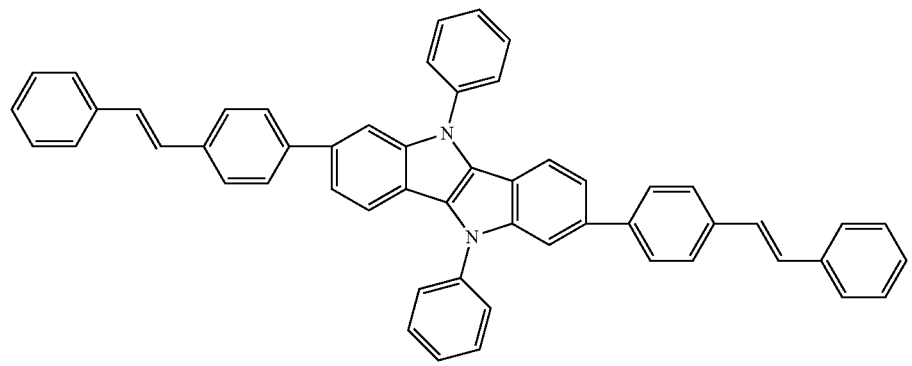

Compound I-22
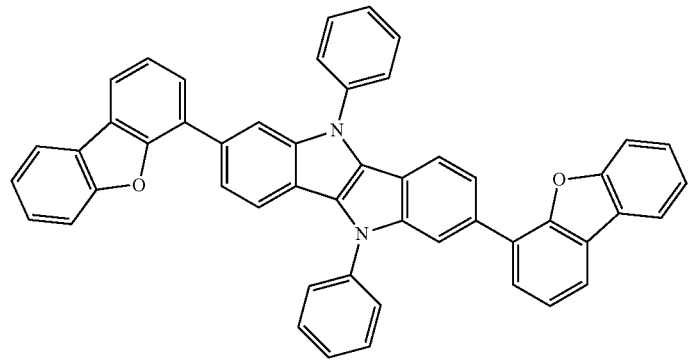
Compound I-23 Compound I-24
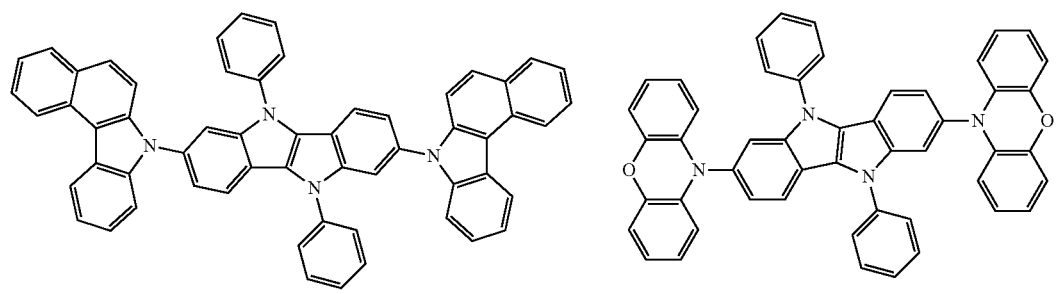
Compound I-25 Compound I-26
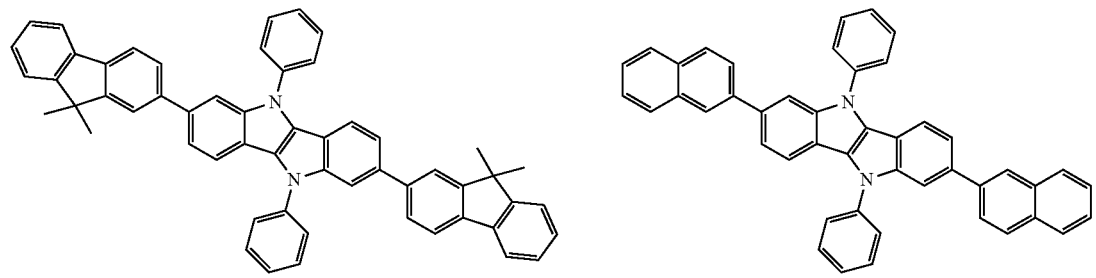
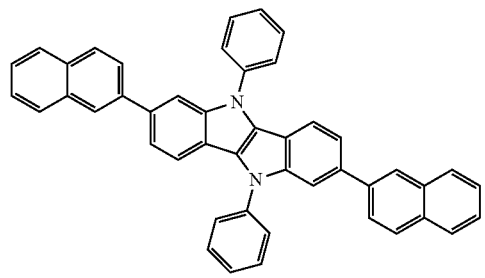
Compound I-27
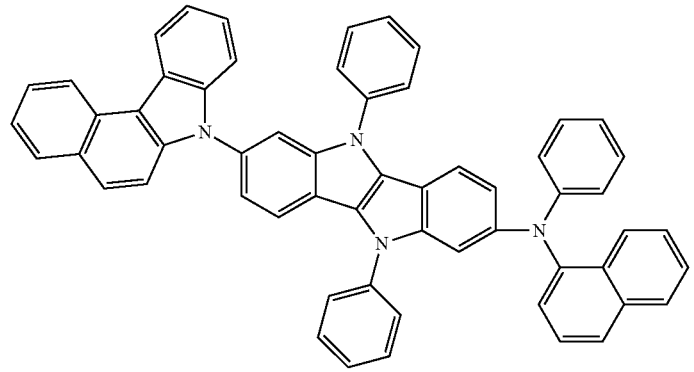
Compound I-28
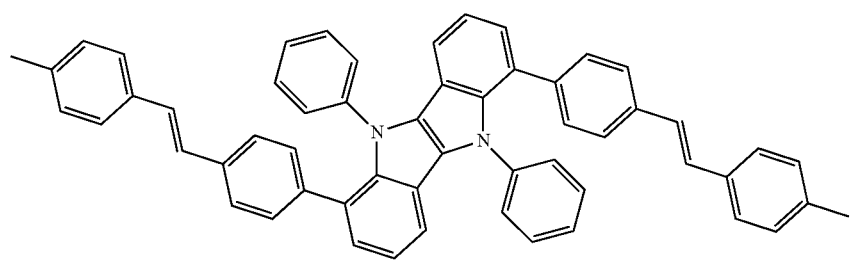

-continued
Compound I-29
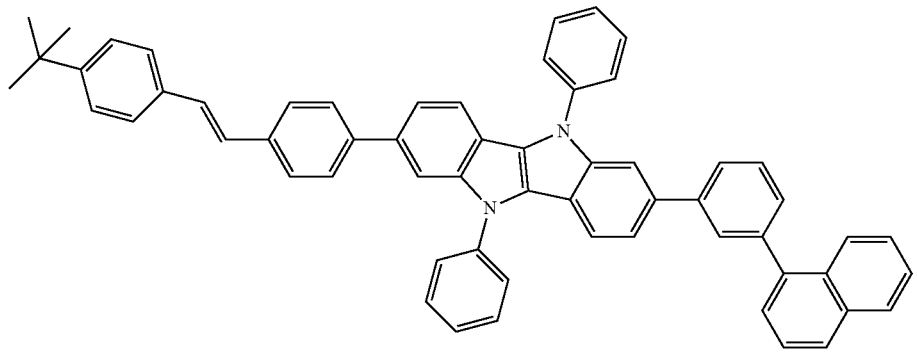
Compound I-30
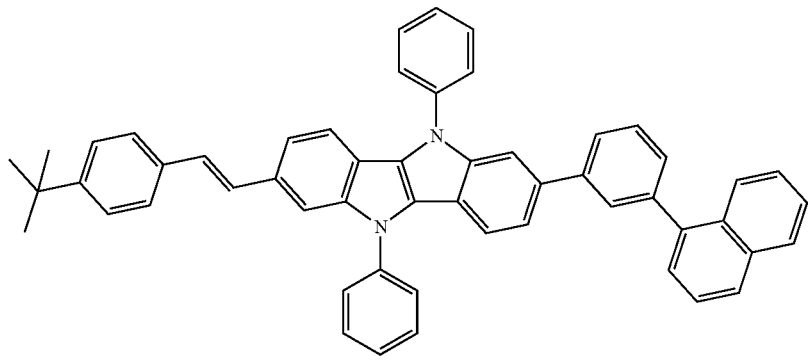
Compound I-31
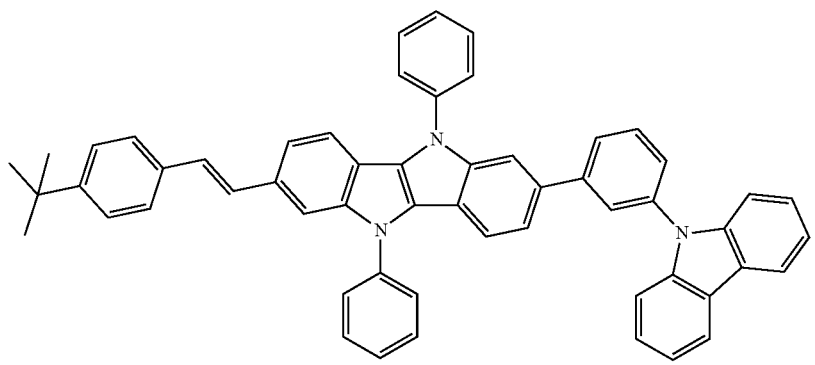
Compound I-32
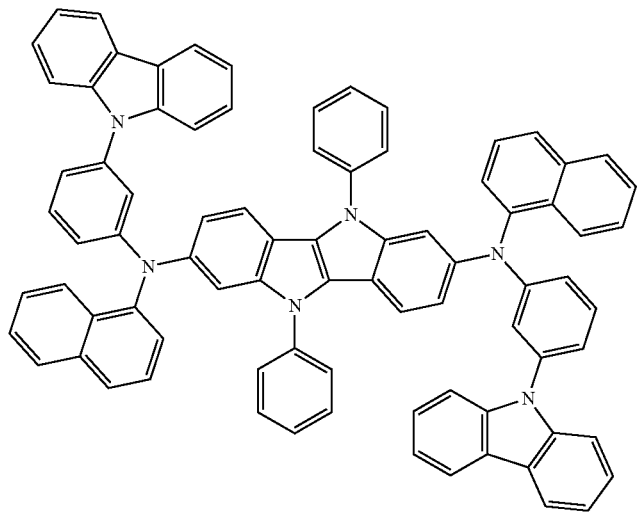

3. Compound Having Formula II or Formula III

In some embodiments, the new compound is an electroactive compound has having Formula II

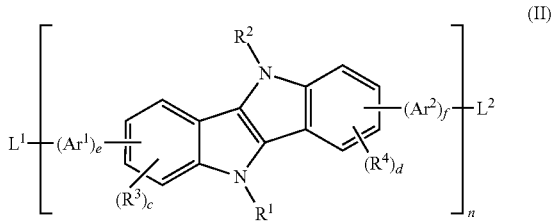

wherein:
- $Ar^1$ and $Ar^2$ are the same or different and are selected from the group consisting of aryl groups, heteroaryl groups, substituted derivatives thereof, and deuterated analogs thereof;
- $R^1$ and $R^2$ are the same or different at each occurrence and are selected from the group consisting of alkyl, silyl, germyl, aryl, heteroaryl and deuterated analogs thereof;
- $R^3$ and $R^4$ are the same or different at each occurrence and are selected from the group consisting of D, alkyl, alkoxy, silyl, siloxy, siloxane, germyl, aryl, alkenylaryl, aryloxy, heteroaryl, diarylamino, deuterated alkyl, deuterated alkoxy, deuterated silyl, deuterated siloxy, deuterated siloxane, deuterated germyl, deuterated aryl, deuterated alkenylaryl, deuterated aryloxy, deuterated heteroaryl, and deuterated diarylamino;
- $L^1$ and $L^2$ are the same or different and are selected from the group consisting of H, D, halogen, aryl, arylamino, crosslinkable groups, deuterated aryl, deuterated arylamino, and deuterated crosslinkable groups;
- c and d are the same or different and are an integer from 0-3;
- e and f are the same or different and are 0 or 1; and
- n is an integer greater than 0.

The compound having Formula II can be a small molecule with n=1, an oligomer, or a polymer. As used herein, the term "compound having Formula II" is intended to include small molecules, oligomers and polymers.

In some embodiments of Formula II, n=1 and $L^1$ is halogen. Such compounds can be useful as monomers for the formation of polymeric compounds.

In some embodiments, the halogen is Cl or Br; in some embodiments, Br.

In some embodiments of Formula II, n=1 and $L^2$ is halogen.

In some embodiments of Formula II, n=1 and $L^1$ is a crosslinking group or deuterated crosslinking group.

In some embodiments of Formula II, n=1 and $L^2$ is a crosslinking group or deuterated crosslinking group.

In some embodiments of Formula II, n=1 and $L^1$ is H or D.

In some embodiments of Formula II, n=1 and $L^2$ is H or D.

In some embodiments of Formula II, n=2-10.

In some embodiments of Formula II, the compound is a polymer with n>10. In some embodiments, the compound is a polymer with $M_n$>20,000; in some embodiments, $M_n$>50,000.

In some embodiments of Formula II, n>10 and $L^1$ is selected from aryl, arylamino, crosslinkable groups, and deuterated analogs thereof.

In some embodiments of Formula II, n>10 and $L^2$ is selected from aryl, arylamino, crosslinkable groups, and deuterated analogs thereof.

In some embodiments of Formula II, n>10 and $L^1$ is selected from phenyl, diphenylamino, and deuterated analogs thereof.

In some embodiments of Formula II, n>10 and $L^2$ is selected from phenyl, diphenylamino, and deuterated analogs thereof.

In some embodiments of Formula II, e=0.
In some embodiments of Formula II, e=1.
In some embodiments of Formula II, f=0.
In some embodiments of Formula II, f=1.
In some embodiments of Formula II, e=f=0.
In some embodiments of Formula II, e=f=1.

In some embodiments of Formula II, e=0 and $L^1$ is bonded to position 6 on the indoloindole core, as defined above.
In some embodiments of Formula II, e=0 and $L^1$ is bonded to position 7 on the indoloindole core, as defined above.
In some embodiments of Formula II, e=0 and $L^1$ is bonded to position 8 on the indoloindole core, as defined above.
In some embodiments of Formula II, e=0 and $L^1$ is bonded to position 9 on the indoloindole core, as defined above.
In some embodiments of Formula II, f=0 and $L^2$ is bonded to position 1 on the indoloindole core, as defined above.
In some embodiments of Formula II, f=0 and $L^2$ is bonded to position 2 on the indoloindole core, as defined above.
In some embodiments of Formula II, f=0 and $L^2$ is bonded to position 3 on the indoloindole core, as defined above.
In some embodiments of Formula II, f=0 and $L^2$ is bonded to position 4 on the indoloindole core, as defined above.

In some embodiments of Formula II, $Ar^1$=$Ar^2$.
In some embodiments of Formula II, $Ar^1$≠$Ar^2$.

In some embodiments of Formula II, e=1 and $Ar^1$ is bonded to position 6 on the indoloindole core, as defined above.
In some embodiments of Formula II, e=1 and $Ar^1$ is bonded to position 7 on the indoloindole core, as defined above.
In some embodiments of Formula II, e=1 and $Ar^1$ is bonded to position 8 on the indoloindole core, as defined above.
In some embodiments of Formula II, e=1 and $Ar^1$ is bonded to position 9 on the indoloindole core, as defined above.
In some embodiments of Formula II, f=1 and $Ar^2$ is bonded to position 1 on the indoloindole core, as defined above.
In some embodiments of Formula II, f=1 and $Ar^2$ is bonded to position 2 on the indoloindole core, as defined above.
In some embodiments of Formula II, f=1 and $Ar^2$ is bonded to position 3 on the indoloindole core, as defined above.
In some embodiments of Formula II, f=1 and $Ar^2$ is bonded to position 4 on the indoloindole core, as defined above.

In some embodiments of Formula II, e=1 and $Ar^1$ is a hydrocarbon aryl group having 6-36 ring carbons. The hydrocarbon aryl group can include one or more single ring groups bonded together, one or more fused rings, or combinations thereof.

In some embodiments of Formula II, e=1 and $Ar^1$ has no heteroaromatic groups.

In some embodiments of Formula II, e=1 and $Ar^1$ has Formula d

Formula d

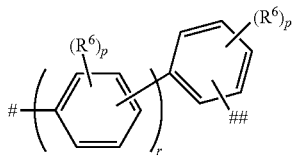

where:
R⁶ is the same or different at each occurrence and is selected from the group consisting of D, alkyl, alkoxy, siloxane, silyl, germyl, diarylamino, carbazolyl, deuterated alkyl, deuterated alkoxy, deuterated siloxane, deuterated silyl, deuterated germyl, deuterated diarylamino, and deuterated carbazolyl, where adjacent R⁶ groups can be joined together to form a fused aromatic ring or a deuterated fused aromatic ring;
p is the same or different at each occurrence and is an integer from 0-4;
r is an integer from 1 to 5;
\# indicates a point of attachment; and
\#\# indicates a point of attachment.

In some embodiments, e=1 and Ar¹ has Formula e

Formula e

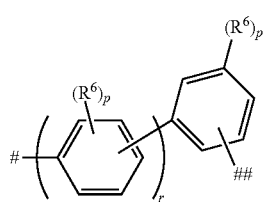

where R⁶, p, r, \# and \#\# are as in Formula d.

In some embodiments of Formula II, e=1 and Ar¹ is selected from the group consisting of phenyl, biphenyl, 1-naphthyl, 2-naphthyl, anthracenyl, fluorenyl, stilbenyl, deuterated analogs thereof, and derivatives thereof having one or more substituents selected from the group consisting of fluoro, alkyl, alkoxy, silyl, siloxy, germyl, a substituent with a crosslinking group, and deuterated analogs thereof.

In some embodiments of Formula II, e=1 and Ar¹ is an N-heteroaryl or deuterated N-heteroaryl, as described above.

In some embodiments of Formula II, e=1 and Ar¹ is an S-heteroaryl, as described above.

In some embodiments of Formula II, e=1 and Ar¹ is an O-heteroaryl, as described above.

In some embodiments of Formula II, e=1 and Ar¹ is an N,O-heteroaryl, as described above.

In some embodiments of Formula II, e=1 and Ar¹ is an N,S-heteroaryl, as described above.

All of the above-described embodiments for Ar¹ apply equally to Ar².

In some embodiments of Formula II, c=0.
In some embodiments of Formula II, c=1.
In some embodiments of Formula II, c=2.
In some embodiments of Formula II, c=3.
In some embodiments of Formula II, c>0.
In some embodiments of Formula II, d=0.
In some embodiments of Formula II, d=1.
In some embodiments of Formula II, d=2.
In some embodiments of Formula II, d=3.
In some embodiments of Formula II, d>0.

All of the above-described embodiments for R¹, R², R³, and R⁴ in Formula I apply equally to R¹, R², R³, and R⁴ in Formula II.

In some embodiments, the electroactive compound of Formula II has Formula II-a

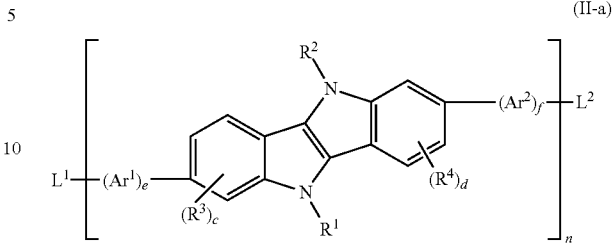

(II-a)

wherein:
Ar¹ and Ar² are the same or different and are selected from the group consisting of aryl groups, heteroaryl groups, substituted derivatives thereof, and deuterated analogs thereof;
R¹ and R² are the same or different at each occurrence and are selected from the group consisting of alkyl, silyl, germyl, aryl, heteroaryl and deuterated analogs thereof;
R³ and R⁴ are the same or different at each occurrence and are selected from the group consisting of D, alkyl, alkoxy, silyl, siloxy, siloxane, germyl, aryl, alkenylaryl, aryloxy, heteroaryl, diarylamino, deuterated alkyl, deuterated alkoxy, deuterated silyl, deuterated siloxy, deuterated siloxane, deuterated germyl, deuterated aryl, deuterated alkenylaryl, deuterated aryloxy, deuterated heteroaryl, and deuterated diarylamino;
L¹ and L² are the same or different and are selected from the group consisting of H, D, halogen, aryl, arylamino, crosslinkable groups, deuterated aryl, deuterated arylamino, and deuterated crosslinkable groups;
c and d are the same or different and are an integer from 0-3;
e and f are the same or different and are 0 or 1; and
n is an integer greater than 0.

The compound having Formula II-a can be a small molecule with n=1, an oligomer, or a polymer. As used herein, the term "compound having Formula II-a" is intended to include small molecules, oligomers and polymers.

In some embodiments of Formula II-a, n=2-10.

In some embodiments of Formula II-a, the compound is a polymer with n>10. In some embodiments, the compound is a polymer with $M_n$>20,000; in some embodiments, $M_n$>50,000.

In some embodiments of Formula II-a, L¹ is bonded to position 6 on the indoloindole core, as defined above.

In some embodiments of Formula II-a, L¹ is bonded to position 7 on the indoloindole core, as defined above.

In some embodiments of Formula II-a, L¹ is bonded to position 8 on the indoloindole core, as defined above.

In some embodiments of Formula II-a, L¹ is bonded to position 9 on the indoloindole core, as defined above.

In some embodiments of Formula II-a, L² is bonded to position 1 on the indoloindole core, as defined above.

In some embodiments of Formula II-a, L² is bonded to position 2 on the indoloindole core, as defined above.

In some embodiments of Formula II-a, L² is bonded to position 3 on the indoloindole core, as defined above.

In some embodiments of Formula II-a, L² is bonded to position 4 on the indoloindole core, as defined above.

The above-described embodiments for L¹, L², Ar¹, Ar², R¹, R², R³, R⁴, R¹, R², c, d, e, f, and n in Formula II, apply equally to L¹, L², Ar¹, Ar², R¹, R², R³, R⁴, R¹, R², c, d, e, f, and n in Formula II-a.

In some embodiments, the electroactive compound of Formula II, has Formula II-b

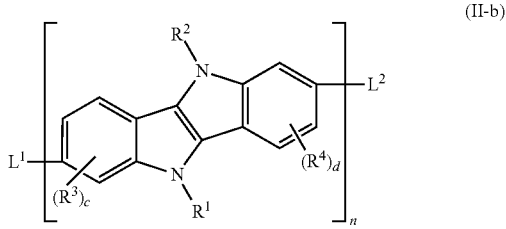

(II-b)

wherein:

R[1] and R[2] are the same or different at each occurrence and are selected from the group consisting of alkyl, silyl, germyl, aryl, heteroaryl and deuterated analogs thereof;

R[3] and R[4] are the same or different at each occurrence and are selected from the group consisting of D, alkyl, alkoxy, silyl, siloxy, siloxane, germyl, aryl, alkenylaryl, aryloxy, heteroaryl, diarylamino, deuterated alkyl, deuterated alkoxy, deuterated silyl, deuterated siloxy, deuterated siloxane, deuterated germyl, deuterated aryl, deuterated alkenylaryl, deuterated aryloxy, deuterated heteroaryl, and deuterated diarylamino;

L[1] and L[2] are the same or different and are selected from the group consisting of H, D, halogen, aryl, arylamino, crosslinkable groups, deuterated aryl, deuterated arylamino, and deuterated crosslinkable groups;

c and d are the same or different and are an integer from 0-3;

e and f are the same or different and are 0 or 1; and n is an integer greater than 0.

The compound having Formula II-b can be a small molecule with n=1, an oligomer, or a polymer. As used herein, the term "compound having Formula II-b" is intended to include small molecules, oligomers and polymers.

In some embodiments of Formula II-b, n=2-10.

In some embodiments of Formula II-b, the compound is a polymer with n>10. In some embodiments, the compound is a polymer with $M_n$>20,000; in some embodiments, $M_n$>50,000.

In some embodiments of Formula II-b, L[1] is bonded to position 6 on the indoloindole core, as defined above.

In some embodiments of Formula II-b, L[1] is bonded to position 7 on the indoloindole core, as defined above.

In some embodiments of Formula II-b, L[1] is bonded to position 8 on the indoloindole core, as defined above.

In some embodiments of Formula II-b, L[1] is bonded to position 9 on the indoloindole core, as defined above.

In some embodiments of Formula II-b, L[2] is bonded to position 1 on the indoloindole core, as defined above.

In some embodiments of Formula II-b, L[2] is bonded to position 2 on the indoloindole core, as defined above.

In some embodiments of Formula II-b, L[2] is bonded to position 3 on the indoloindole core, as defined above.

In some embodiments of Formula II-b, L[2] is bonded to position 4 on the indoloindole core, as defined above.

The above-described embodiments for L[1], L[2], R[1], R[2], R[3], R[4], R[1], R[2], c, d, and n in Formula II, apply equally to L[1], L[2], R[1], R[2], R[3], R[4], R[1], R[2], c, d, and n in Formula II-b.

Any of the above embodiments for Formula II, Formula II-a, or Formula II-b can be combined with one or more of the other embodiments, so long as they are not mutually exclusive. For example, the embodiment in which R[1] is a hydrocarbon aryl group or deuterated hydrocarbon aryl having 6-36 ring carbons can be combined with the embodiment in which d>0 and at least one R[4] is an S-heteroaryl. The same is true for the other non-mutually-exclusive embodiments discussed above. The skilled person would understand which embodiments were mutually exclusive and would thus readily be able to determine the combinations of embodiments that are contemplated by the present application.

In some embodiments, the new compound is an electroactive compound having Formula III

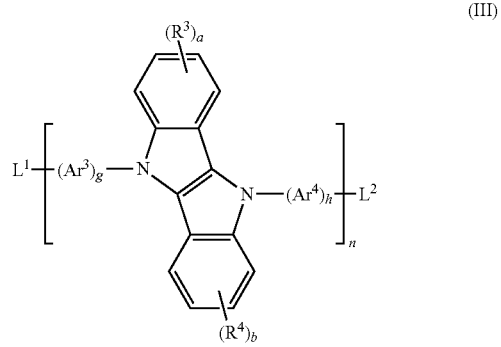

(III)

wherein:

Ar[3] and Ar[4] are the same or different and are selected from the group consisting of aryl groups, heteroaryl groups, substituted derivatives thereof, and deuterated analogs thereof;

R[1] and R[2] are the same or different at each occurrence and are selected from the group consisting of alkyl, silyl, germyl, aryl, heteroaryl and deuterated analogs thereof;

R[3] and R[4] are the same or different at each occurrence and are selected from the group consisting of D, alkyl, alkoxy, silyl, siloxy, siloxane, germyl, aryl, alkenylaryl, aryloxy, heteroaryl, diarylamino, deuterated alkyl, deuterated alkoxy, deuterated silyl, deuterated siloxy, deuterated siloxane, deuterated germyl, deuterated aryl, deuterated alkenylaryl, deuterated aryloxy, deuterated heteroaryl, and deuterated diarylamino;

L[1] and L[2] are the same or different and are selected from the group consisting of H, D, halogen, aryl, arylamino, crosslinkable groups, deuterated aryl, deuterated arylamino, and deuterated crosslinkable groups;

a and b are the same or different and are an integer from 0-4;

g and h are the same or different and are 0 or 1, with the proviso that g+h>0; and n is an integer greater than 0.

The compound having Formula III can be a small molecule with n=1, an oligomer, or a polymer. As used herein, the term "compound having Formula III" is intended to include small molecules, oligomers and polymers.

In some embodiments of Formula III, g=0 and h=1.

In some embodiments of Formula III, g=1 and h=0.

In some embodiments of Formula III, g=h=1.

All of the above-described embodiments for Ar[1] in Formula II apply equally to Ar[3] in Formula III.

All of the above-described embodiments for Ar[2] in Formula II apply equally to Ar[4] in Formula III.

In some embodiments of Formula III, a=0.

In some embodiments of Formula III, a=1.

In some embodiments of Formula III, a=2.

In some embodiments of Formula III, a=3.

In some embodiments of Formula III, a=4.

In some embodiments of Formula III, a>0.

In some embodiments of Formula III, a>0 and at least one R[3] is at position 6 on the indoloindole core, as defined above.

In some embodiments of Formula III, a>0 and at least one R[3] is at position 7 on the indoloindole core, as defined above.

In some embodiments of Formula III, a>0 and at least one R[3] is at position 8 on the indoloindole core, as defined above.

In some embodiments of Formula III, a>0 and at least one $R^3$ is at position 9 on the indoloindole core, as defined above.

In some embodiments of Formula III, b=0.
In some embodiments of Formula III, b=1.
In some embodiments of Formula III, b=2.
In some embodiments of Formula III, b=3.
In some embodiments of Formula III, b=4.
In some embodiments of Formula III, b>0.

In some embodiments of Formula III, b>0 and at least one $R^4$ is at position 1 on the indoloindole core, as defined above.

In some embodiments of Formula III, b>0 and at least one $R^4$ is at position 2 on the indoloindole core, as defined above.

In some embodiments of Formula III, b>0 and at least one $R^4$ is at position 3 on the indoloindole core, as defined above.

In some embodiments of Formula III, b>0 and at least one $R^4$ is at position 4 on the indoloindole core, as defined above.

All of the above-described embodiments for n, $L^1$, and $L^2$ in Formula II apply equally to n, $L^1$, and $L^2$ in Formula III.

All of the above-described embodiments for $R^1$, $R^2$, $R^3$, and $R^4$ in Formula I apply equally to $R^1$, $R^2$, $R^3$, and $R^4$ in Formula III.

Any of the above embodiments for Formula III can be combined with one or more of the other embodiments, so long as they are not mutually exclusive. For example, the embodiment in which f=1 and Ar1 has Formula c can be combined with the embodiment in which a=2 and at least one $R^3$ is naphthyl and the embodiment in which at least one $R^3$ is D. The same is true for the other non-mutually-exclusive embodiments discussed above. The skilled person would understand which embodiments were mutually exclusive and would thus readily be able to determine the combinations of embodiments that are contemplated by the present application.

The compounds of Formula II or Formula III can be made using known coupling techniques and polymerization techniques, as described above. Deuterated compounds can be prepared as described above.

Exemplary preparations are given in the Examples.

Some non-limiting examples of compounds having Formula II are shown below.

Compound II-1

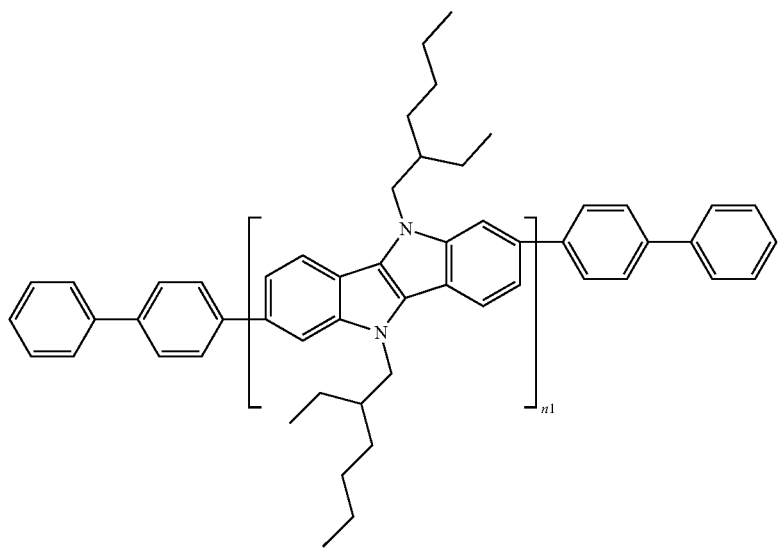

Compound II-2

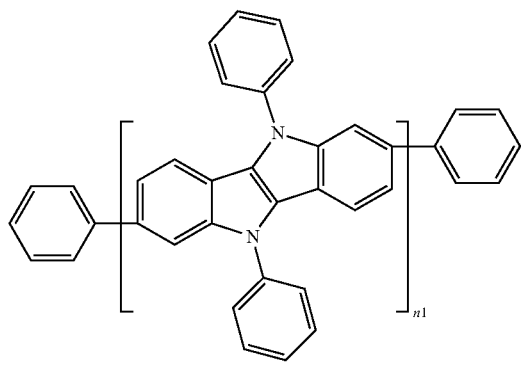

Compound II-3

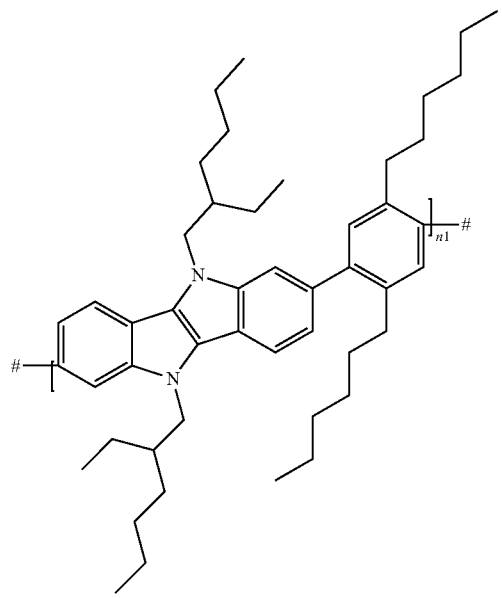

-continued
Compound II-4
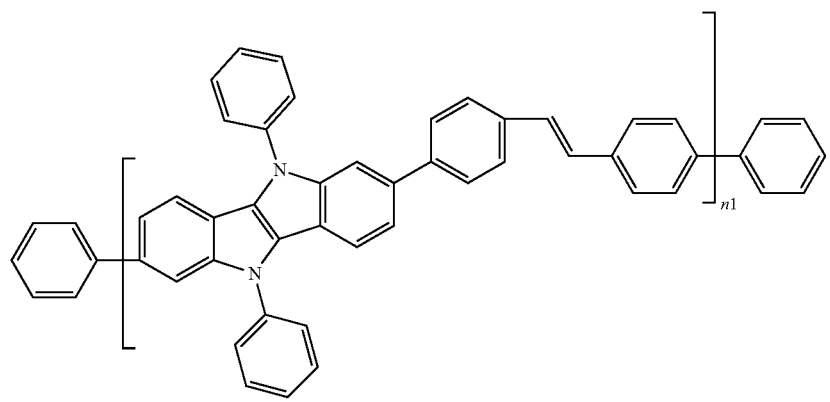
Compound II-5
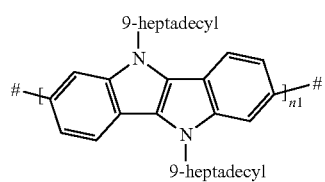
Compound II-6
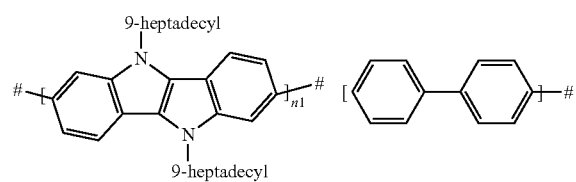
Compound II-7
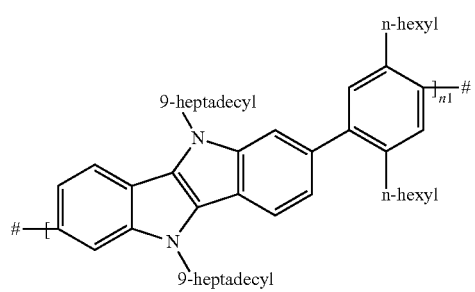
Compound II-8
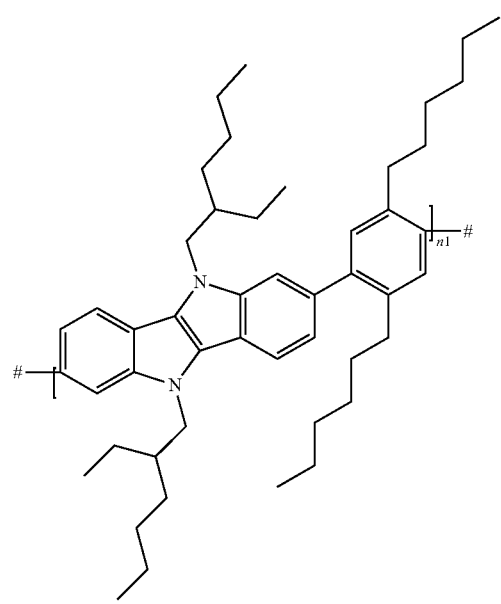

In the above compounds, n1 is an integer greater than 1 and # indicates a point of attachment. In some embodiments of the above compounds, n1>10.

Some non-limiting examples of compounds having Formula III are shown below.

Compound III-1

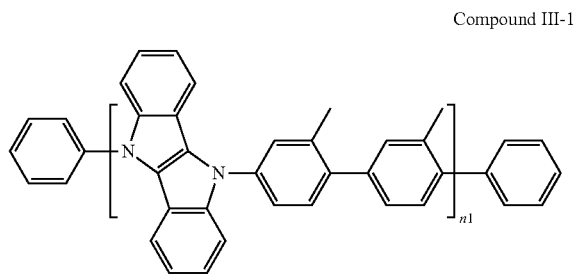

In the above compounds, n1 is an integer greater than 1. In some embodiments of the above compound, n1>10.

4. Copolymer Having at Least One Unit of Formula IV or Formula V and the Copolymer of Formula VI or Formula VII In some embodiments, the electroactive compound is a copolymer having at least one unit of Formula IV

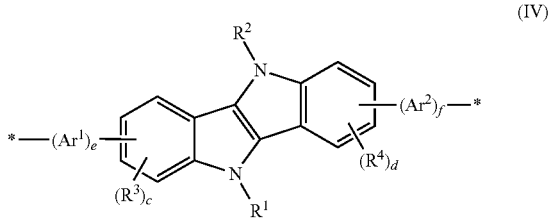

(IV)

wherein:
$Ar^1$ and $Ar^2$ are the same or different and are selected from the group consisting of aryl groups, heteroaryl groups, substituted derivatives thereof, and deuterated analogs thereof;
$R^1$ and $R^2$ are the same or different at each occurrence and are selected from the group consisting of alkyl, silyl, germyl, aryl, heteroaryl and deuterated analogs thereof;
$R^3$ and $R^4$ are the same or different at each occurrence and are selected from the group consisting of D, alkyl, alkoxy, silyl, siloxy, siloxane, germyl, aryl, alkenylaryl, aryloxy, heteroaryl, diarylamino, deuterated alkyl, deuterated alkoxy, deuterated silyl, deuterated siloxy, deuterated siloxane, deuterated germyl, deuterated aryl, deuterated alkenylaryl, deuterated aryloxy, deuterated heteroaryl, and deuterated diarylamino;
c and d are the same or different and are an integer from 0-3;
e and f are the same or different and are 0 or 1; and
* represents a point of attachment to the copolymer.

In some embodiments of Formula IV, e=1 and $Ar^1$ is bonded to position 6 on the indoloindole core, as defined above.

In some embodiments of Formula IV, e=1 and $Ar^1$ is bonded to position 7 on the indoloindole core, as defined above.

In some embodiments of Formula IV, e=1 and $Ar^1$ is bonded to position 8 on the indoloindole core, as defined above.

In some embodiments of Formula IV, e=1 and $Ar^1$ is bonded to position 9 on the indoloindole core, as defined above.

In some embodiments of Formula IV, f=1 and $Ar^2$ is bonded to position 1 on the indoloindole core, as defined above.

In some embodiments of Formula IV, f=1 and $Ar^2$ is bonded to position 2 on the indoloindole core, as defined above.

In some embodiments of Formula IV, f=1 and $Ar^2$ is bonded to position 3 on the indoloindole core, as defined above.

In some embodiments of Formula IV, f=1 and $Ar^2$ is bonded to position 4 on the indoloindole core, as defined above.

All of the above-described embodiments for $Ar^1$, $Ar^2$, $R^1$, $R^2$, $R^3$, $R^4$, c, d, e, and f in Formula II, apply equally to $Ar^1$, $Ar^2$, $R^1$, $R^2$, $R^3$, $R^4$, c, d, e, and f in Formula IV.

In some embodiments, the electroactive compound is a copolymer having at least one unit of Formula IV-a

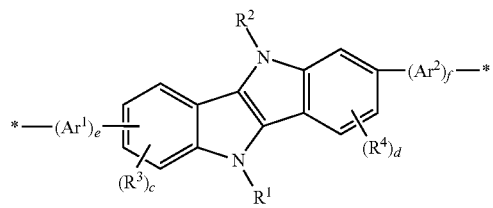

(IV-a)

wherein:
$Ar^1$ and $Ar^2$ are the same or different and are selected from the group consisting of aryl groups, heteroaryl groups, substituted derivatives thereof, and deuterated analogs thereof;
$R^1$ and $R^2$ are the same or different at each occurrence and are selected from the group consisting of alkyl, silyl, germyl, aryl, heteroaryl and deuterated analogs thereof;
$R^3$ and $R^4$ are the same or different at each occurrence and are selected from the group consisting of D, alkyl, alkoxy, silyl, siloxy, siloxane, germyl, aryl, alkenylaryl, aryloxy, heteroaryl, diarylamino, deuterated alkyl, deuterated alkoxy, deuterated silyl, deuterated siloxy, deuterated siloxane, deuterated germyl, deuterated aryl, deuterated alkenylaryl, deuterated aryloxy, deuterated heteroaryl, and deuterated diarylamino;
c and d are the same or different and are an integer from 0-3;
e and f are the same or different and are 0 or 1; and
* represents a point of attachment to the copolymer.

All of the above-described embodiments for $Ar^1$, $Ar^2$, $R^1$, $R^2$, $R^3$, $R^4$, c, d, e, and f in Formula IV, apply equally to $Ar^1$, $Ar^2$, $R^1$, $R^2$, $R^3$, $R^4$, c, d, e, and f in Formula IV-a.

In some embodiments, the electroactive compound is a copolymer having at least one unit of Formula IV-b

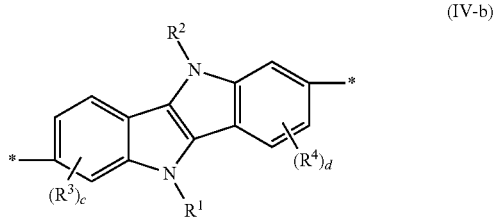
(IV-b)

wherein:
R¹ and R² are the same or different at each occurrence and are selected from the group consisting of alkyl, silyl, germyl, aryl, heteroaryl and deuterated analogs thereof;
R³ and R⁴ are the same or different at each occurrence and are selected from the group consisting of D, alkyl, alkoxy, silyl, siloxy, siloxane, germyl, aryl, alkenylaryl, aryloxy, heteroaryl, diarylamino, deuterated alkyl, deuterated alkoxy, deuterated silyl, deuterated siloxy, deuterated siloxane, deuterated germyl, deuterated aryl, deuterated alkenylaryl, deuterated aryloxy, deuterated heteroaryl, and deuterated diarylamino;
c and d are the same or different and are an integer from 0-3; and
* represents a point of attachment to a copolymer.

All of the above-described embodiments for R¹, R², R³, R⁴, c, and d in Formula IV, apply to R¹, R², R³, R⁴, c, and d in Formula IV-b.

In some embodiments, the electroactive compound is a copolymer having at least one unit of Formula V

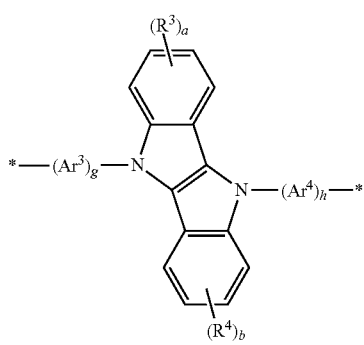
(V)

wherein:
Ar³ and Ar⁴ are the same or different and are selected from the group consisting of aryl groups, heteroaryl groups, substituted derivatives thereof, and deuterated analogs thereof;
R¹ and R² are the same or different at each occurrence and are selected from the group consisting of alkyl, silyl, germyl, aryl, heteroaryl and deuterated analogs thereof;
R³ and R⁴ are the same or different at each occurrence and are selected from the group consisting of D, alkyl, alkoxy, silyl, siloxy, siloxane, germyl, aryl, alkenylaryl, aryloxy, heteroaryl, diarylamino, deuterated alkyl, deuterated alkoxy, deuterated silyl, deuterated siloxy, deuterated siloxane, deuterated germyl, deuterated aryl, deuterated alkenylaryl, deuterated aryloxy, deuterated heteroaryl, and deuterated diarylamino;
a and b are the same or different and are an integer from 0-4;
g and h are the same or different and are 0 or 1, with the proviso that g+h>0; and
* represents a point of attachment to the copolymer.

In some embodiments of Formula V, a>0 and R³ is bonded to position 6 on the indoloindole core, as defined above.
In some embodiments of Formula V, a>0 and R³ is bonded to position 7 on the indoloindole core, as defined above.
In some embodiments of Formula V, a>0 and R³ is bonded to position 8 on the indoloindole core, as defined above.
In some embodiments of Formula V, a>0 and R³ is bonded to position 9 on the indoloindole core, as defined above.
In some embodiments of Formula V, b>0 and R⁴ is bonded to position 1 on the indoloindole core, as defined above.
In some embodiments of Formula V, b>0 and R⁴ is bonded to position 2 on the indoloindole core, as defined above.
In some embodiments of Formula V, b>0 and R⁴ is bonded to position 3 on the indoloindole core, as defined above.
In some embodiments of Formula V, b>0 and R⁴ is bonded to position 4 on the indoloindole core, as defined above.

All of the above-described embodiments for Ar³, Ar⁴, R³, R⁴, a, b, g, and h in Formula III, apply equally to Ar³, Ar⁴, R³, R⁴, a, b, g, and h in Formula V.

In some embodiments, the copolymer has Formula VI

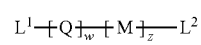
Formula VI wherein:
L¹ and L² are the same or different and are selected from the group consisting of H, D, halogen, aryl, arylamino, crosslinkable groups, deuterated aryl, deuterated arylamino, and deuterated crosslinkable groups;
M is a conjugated moiety;
Q is a monomeric unit having Formula IV; and
w and z represent non-zero mole fractions such that w+z=1.

In some embodiments of Formula VI, the "Q" and "M" units are ordered in a regular alternating pattern.
In some embodiments of Formula VI, the "Q" and "M" units are ordered in blocks of like monomers.
In some embodiments of Formula VI, the "Q" and "M" units are randomly arranged.
In some embodiments of Formula VI, L¹ is selected from aryl, arylamino, crosslinkable groups, and deuterated analogs thereof.
In some embodiments of Formula VI, L¹ is selected from phenyl, triphenylamino, and deuterated analogs thereof.
In some embodiments of Formula VI, L² is selected from aryl, arylamino, crosslinkable groups, and deuterated analogs thereof.
In some embodiments of Formula VI, L² is selected from phenyl, triphenylamino, and deuterated analogs thereof.
In some embodiments of Formula VI, at least one ## represents a point of attachment to L².
In some embodiments of Formula VI, M is a deuterated aromatic moiety.
In some embodiments of Formula VI, M is a monomeric unit derived from an olefin, an acetylenic compound, a styrene, a stilbene, a substituted derivative thereof, or a deuterated analog thereof.

In some embodiments of Formula VI, M has Formula d, as defined above.

In some embodiments of Formula VI, M has Formula e, as defined above.

In some embodiments of Formula VI, M is a monomeric unit derived from a hydrocarbon aryl having two or more fused rings or a deuterated analog thereof.

In some embodiments of Formula VI, M is a monomeric unit derived from the group consisting of naphthalene, anthracene, fluorene, phenanthrene, triphenylene, substituted derivatives thereof, and deuterated analogs thereof.

In some embodiments of Formula VI, M is a monomeric unit derived from a triarylamino group or deuterated analog thereof.

In some embodiments of Formula VI, M is a monomeric unit having two or more triarylamino groups.

In some embodiments of Formula VI, M is a monomeric unit derived from a heteroaromatic compound having at least one ring atom which is selected from the group consisting of N, O, and S.

In some embodiments of Formula VI, M is a monomeric unit derived from an N-heteroaryl, as described above.

In some embodiments of Formula VI, M is a monomeric unit derived from an S-heteroaryl, as described above.

In some embodiments of Formula VI, M is a monomeric unit derived from an O-heteroaryl, as described above.

In some embodiments of Formula VI, M is a monomeric unit derived from an N,O-heteroaryl as described above.

In some embodiments of Formula VI, M is a monomeric unit derived from an N,S-heteroaryl as described above.

In some embodiments of Formula VI, M has one of the formulae given below.

M1
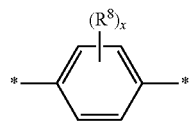

M2
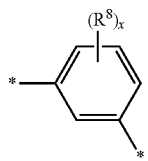

M3
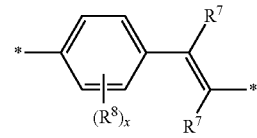

M4
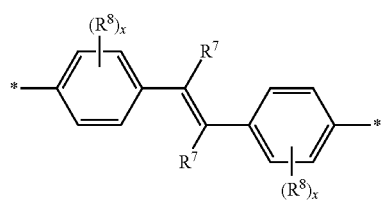

M5
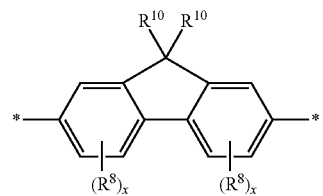

M6
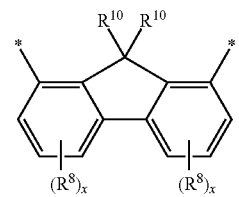

M7
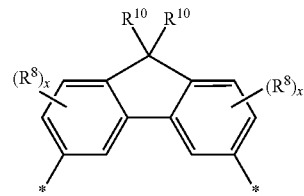

M8
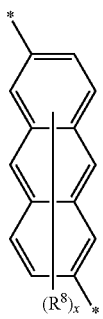

M9
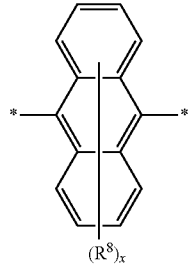

M10
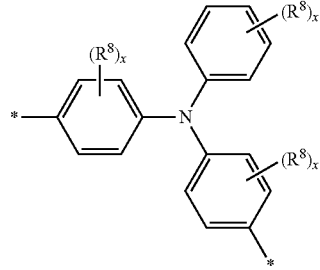

-continued

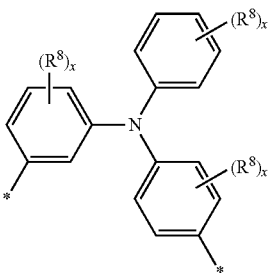
M11

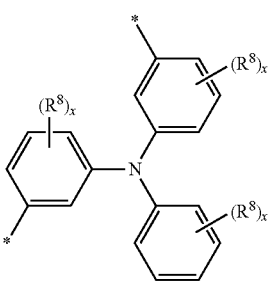
M12

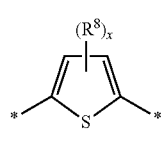
M13

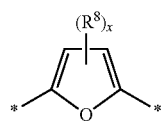
M14

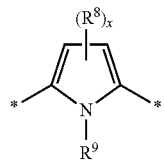
M15

In M1 through M15:
  $R^7$ is the same or different at each occurrence and is selected from the group consisting of H, D, alkyl, and deuterated alkyl;
  $R^8$ is the same or different at each occurrence and is selected from the group consisting of D, alkyl, silyl, germyl, aryl, deuterated alkyl, deuterated silyl, deuterated germyl, and deuterated aryl;
  $R^9$ is the same or different at each occurrence and is selected from the group consisting of aryl and deuterated aryl;
  $R^{10}$ is the same or different at each occurrence and is selected from the group consisting of alkyl, aryl, and deuterated analogs thereof;
  x is the same or different at each occurrence and is an integer from 0 to the maximum number of positions available for substituents; and
  * represents the point of attachment in the copolymer.

In some embodiments of M1 through M15, x is 0-2.
In some embodiments of Formula VI, w>z.
In some embodiments of Formula VI, w is in the range of 0.5-0.99; in some embodiments, 0.6-0.95; in some embodiments, 0.75-0.95.

Any of the above embodiments for Formula VI can be combined with one or more of the other embodiments, so long as they are not mutually exclusive. For example, the embodiment in which Q has Formula IV-a can be combined with the embodiment in which c>0 and $R^3$ is an N-heteroaryl and with the embodiment in which M has formula M1. The same is true for the other non-mutually-exclusive embodiments discussed above. The skilled person would understand which embodiments were mutually exclusive and would thus readily be able to determine the combinations of embodiments that are contemplated by the present application.

In some embodiments, the copolymer has Formula VII

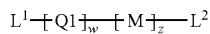

Formula VII where:
  $L^1$ and $L^2$ are the same or different and are selected from the group consisting of H, D, halogen, aryl, arylamino, crosslinkable groups, deuterated aryl, deuterated arylamino, and deuterated crosslinkable groups;
  M is a conjugated moiety;
  Q1 is a monomeric unit having Formula V; and
  w and z represent non-zero mole fractions such that w+z=1.

In some embodiments of Formula VII, the "Q1" and "M" units are ordered in a regular alternating pattern.

In some embodiments of Formula VII, the "Q1" and "M" units are ordered in blocks of like monomers.

In some embodiments of Formula VII, the "Q1" and "M" units are randomly arranged.

All of the above-described embodiments for $L^1$, $L^2$, M, and w in Formula VI apply equally to $L^1$, $L^2$, M, and w in Formula VII.

Any of the above embodiments for Formula VII can be combined with one or more of the other embodiments, so long as they are not mutually exclusive. For example, the embodiment in which g=1 and $Ar^3$ is a hydrocarbon aryl group having 6-36 ring carbons has can be combined with the embodiment in which b>0 and $R^4$ is a hydrocarbon aryl group having at least one substituent selected from the group consisting of D, alkyl, silyl, aryl, diarylamino, carbazolyl, deuterated alkyl, deuterated silyl, deuterated aryl, deuterated diarylamino, and deuterated carbazolyl and with the embodiment in which M has formula M4. The same is true for the other non-mutually-exclusive embodiments discussed above. The skilled person would understand which embodiments were mutually exclusive and would thus readily be able to determine the combinations of embodiments that are contemplated by the present application.

The copolymer having Formula VI or Formula VII can be made using known coupling techniques and polymerization techniques, as described above. Deuterated compounds can be prepared as described above.

Some non-limiting examples of copolymers having Formula VI are shown below.

Compound VI-1

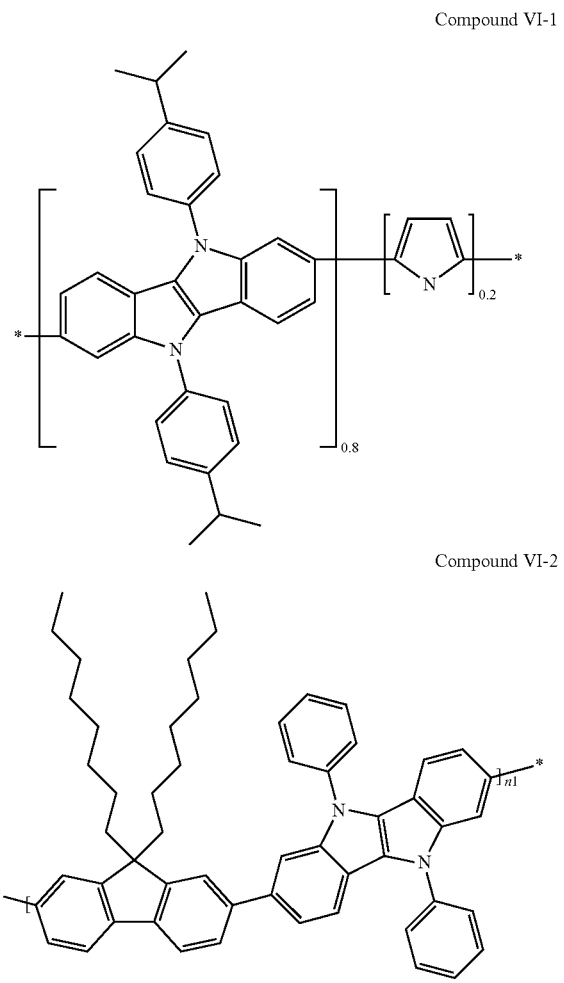

Compound VI-2 where * represents a point of attachment in the copolymer, n1 is an integer greater than 1, and the numbers represent mole fractions. In some embodiments of the above compounds, n1>10.

Some non-limiting examples of copolymers having Formula VII are shown below.

Compound VII-1

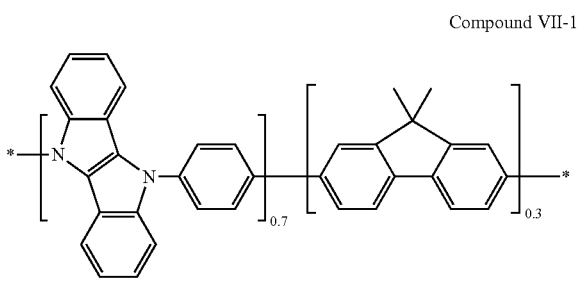

where * represents a point of attachment in the copolymer.

5. Compound Having Formula VIII

In some embodiments, the new compound is an electroactive compound having Formula VIII

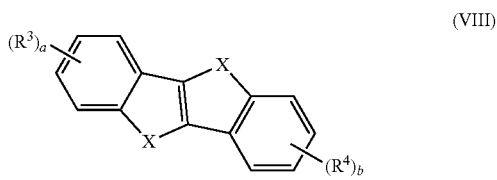

wherein:

$R^3$ and $R^4$ are the same or different at each occurrence and are selected from the group consisting of D, alkyl, alkoxy, silyl, siloxy, siloxane, germyl, aryl, alkenylaryl, aryloxy, heteroaryl, diarylamino, deuterated alkyl, deuterated alkoxy, deuterated silyl, deuterated siloxy, deuterated siloxane, deuterated germyl, deuterated aryl, deuterated alkenylaryl, deuterated aryloxy, deuterated heteroaryl, and deuterated diarylamino;

X is O, S, or Se; and a and b are the same or different and are an integer from 0-4.

In some embodiments of Formula VIII, X=O.

In some embodiments of Formula VIII, X=S.

In some embodiments of Formula VIII, X=Se.

In some embodiments of Formula VIII, $R^3$=$R^4$.

In some embodiments of Formula VIII, $R^3$≠$R^4$.

In some embodiments of Formula VIII, a=1-4.

In some embodiments of Formula VIII, a=1.

In some embodiments of Formula VIII, a=2.

In some embodiments of Formula VIII, a=3.

In some embodiments of Formula VIII, a=4.

In some embodiments of Formula VIII, b=1-4.

In some embodiments of Formula VIII, b=1.

In some embodiments of Formula VIII, b=2.

In some embodiments of Formula VIII, b=3.

In some embodiments of Formula VIII, b=4.

In some embodiments of Formula VIII, a>0 and b>0.

All of the above-described embodiments for $R^3$ and $R^4$ in Formula I apply equally to $R^3$, $R^4$, a and b in Formula VIII.

Any of the above embodiments for Formula VIII can be combined with one or more of the other embodiments, so long as they are not mutually exclusive. For example, the embodiment in which a=2 can be combined with the embodiment in which at least one $R^3$ is D and the embodiment in which at least one $R^3$ has formula a. The same is true for the other non-mutually-exclusive embodiments discussed above. The skilled person would understand which embodiments were mutually exclusive and would thus readily be able to determine the combinations of embodiments that are contemplated by the present application.

The compounds of Formula VIII can be made using known coupling techniques, as described above. Deuterated compounds can be prepared as described above. Exemplary preparations are given in the Examples.

Some non-limiting examples of compounds having Formula VIII are shown below.

Compound VIII-1
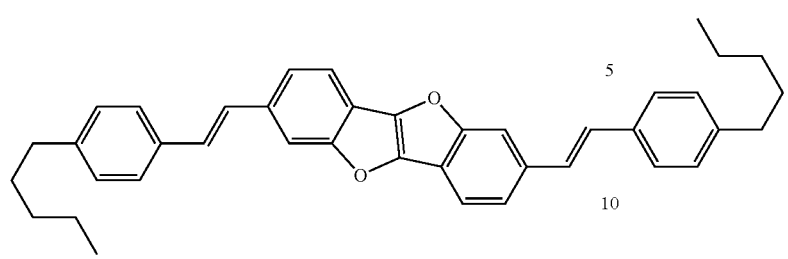
Compound VIII-2
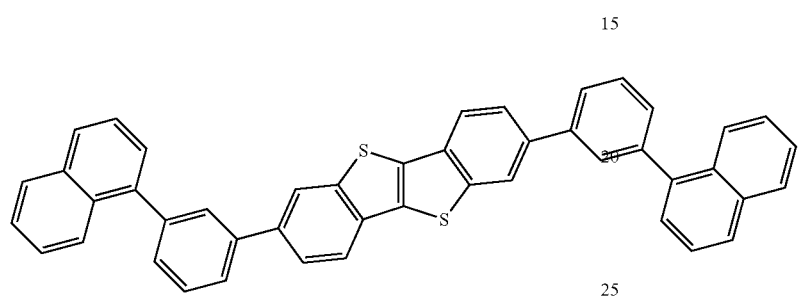
Compound VIII-3
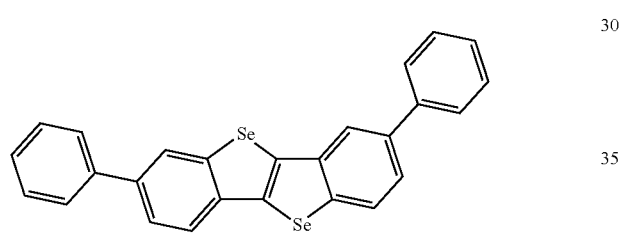
Compound VIII-4
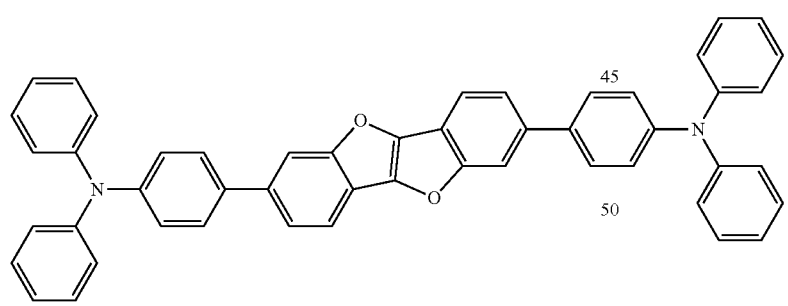
Compound VIII-5
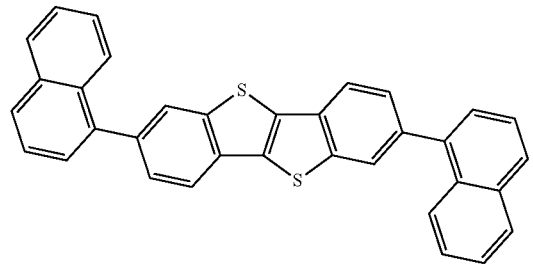
Compound VIII-6
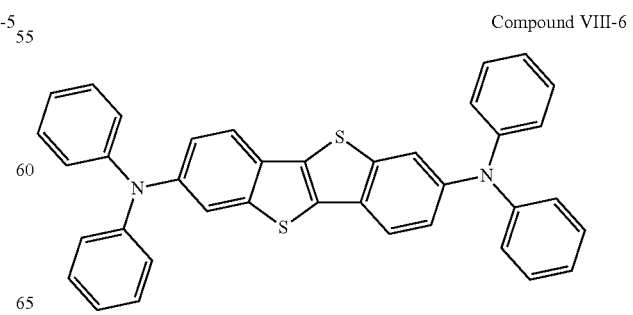

6. Compound Having Formula IX or Formula X

The compounds having Formula IX or Formula X have as fused ring core, as defined above.

In some embodiments, the new compound is an electroactive compound having Formula IX

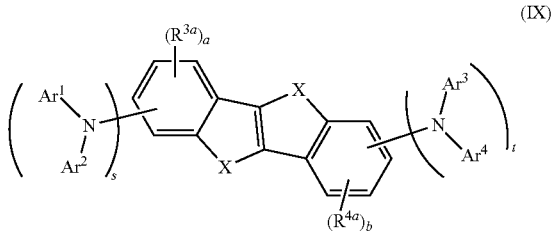

wherein:
X is O, S, or Se;
Ar$^1$-Ar$^4$ are the same or different and are selected from the group consisting of aryl groups, heteroaryl groups, substituted derivatives thereof, and deuterated analogs thereof;
R$^{3a}$ and R$^{4a}$ are the same or different at each occurrence and are selected from the group consisting of D, alkyl, alkoxy, silyl, siloxy, siloxane, germyl, aryl, alkenylaryl, aryloxy, heteroaryl, deuterated alkyl, deuterated alkoxy, deuterated silyl, deuterated siloxy, deuterated siloxane, deuterated germyl, deuterated aryl, deuterated alkenylaryl, deuterated aryloxy, and deuterated heteroaryl;
a and b are the same or different and are an integer from 0-4, with the proviso that when s=1, a is 0-3, and when t=1, b is 0-3; and
s and t are 0 or 1, with the proviso that s+t>0.

In some embodiments of Formula IX, X=O.
In some embodiments of Formula IX, X=S.
In some embodiments of Formula IX, X=Se.
In some embodiments of Formula IX, Ar$^1$=Ar$^2$.
In some embodiments of Formula IX, Ar$^1$≠Ar$^2$.
In some embodiments of Formula IX, Ar$^3$=Ar$^4$.
In some embodiments of Formula IX, Ar$^3$≠Ar$^4$.
In some embodiments of Formula IX, Ar$^1$=Ar$^3$.
In some embodiments of Formula IX, Ar$^2$=Ar$^4$.
In some embodiments of Formula IX, R$^1$=R$^2$.
In some embodiments of Formula IX, R$^1$≠R$^2$.
In some embodiments of Formula IX, s=1 and t=0.
In some embodiments of Formula IX, s=0 and t=1.
In some embodiments of Formula IX, s=t=1.
In some embodiments of Formula IX, s=1 and the amino nitrogen is bonded to position 6 on the fused ring core, as defined above.
In some embodiments of Formula IX, s=1 and the amino nitrogen is bonded to position 7 on the fused ring core, as defined above.
In some embodiments of Formula IX, s=1 and the amino nitrogen is bonded to position 8 on the fused ring core, as defined above.
In some embodiments of Formula IX, s=1 and the amino nitrogen is bonded to position 9 on the fused ring core, as defined above.
In some embodiments of Formula IX, t=1 and the amino nitrogen is bonded to position 1 on the fused ring core, as defined above.
In some embodiments of Formula IX, t=1 and the amino nitrogen is bonded to position 2 on the fused ring core, as defined above.
In some embodiments of Formula IX, t=1 and the amino nitrogen is bonded to position 3 on the fused ring core, as defined above.
In some embodiments of Formula IX, t=1 and the amino nitrogen is bonded to position 4 on the fused ring core, as defined above.
In some embodiments of Formula IX, Ar$^1$ is a hydrocarbon aryl group having 6-36 ring carbons. The hydrocarbon aryl group can include one or more single ring groups bonded together, one or more fused rings, or combinations thereof.
In some embodiments of Formula IX, Ar$^1$ has no heteroaromatic groups.
In some embodiments of Formula IX, Ar$^1$ has Formula a, as defined above.
In some embodiments of Formula IX, Ar$^1$ has Formula b, as defined above.
In some embodiments of Formula IX, Ar$^1$ is selected from the group consisting of phenyl, naphthyl, Formula a, substituted derivatives thereof, and deuterated analogs thereof.
In some embodiments of Formula IX, Ar$^1$ has substituents selected from the group consisting of D, alkyl, silyl, germyl, aryl, diarylamino, carbazolyl, deuterated alkyl, deuterated silyl, deuterated germyl, deuterated aryl, deuterated diarylamino, and deuterated carbazolyl.

All of the above-described embodiments for Ar$^1$ in Formula IX apply equally to Ar$^2$ in Formula IX.
All of the above-described embodiments for Ar$^1$ in Formula IX apply equally to Ar$^3$ in Formula IX.
All of the above-described embodiments for Ar$^1$ in Formula IX apply equally to Ar$^4$ in Formula IX.
All of the above-described embodiments for R$^3$ in Formula I apply equally to R$^{3a}$.
All of the above-described embodiments for R$^4$ in Formula I apply equally to R$^{4a}$ in Formula IX.
All of the above-described embodiments for a and b in Formula I apply equally to R$^3$, R$^4$, a and b in Formula IX, with the proviso that when s=1, a is 0-3, and when t=1, b is 0-3.

In some embodiments, the electroactive compound of Formula IX has Formula IX-a

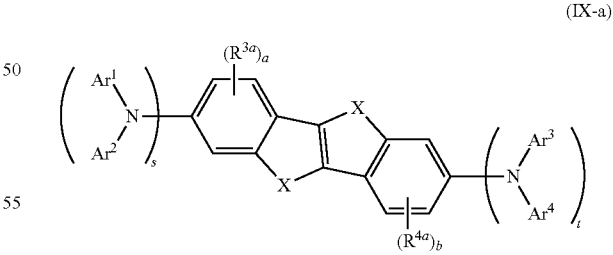

wherein:
X is O, S, or Se;
Ar$^1$-Ar$^4$ are the same or different and are selected from the group consisting of aryl groups, substituted derivatives thereof, and deuterated analogs thereof;
R$^{3a}$ and R$^{4a}$ are the same or different at each occurrence and are selected from the group consisting of D, alkyl, alkoxy, silyl, siloxy, siloxane, germyl, aryl, alkenylaryl, aryloxy, heteroaryl, deuterated alkyl, deuterated alkoxy, deuterated silyl, deuterated siloxy, deuterated siloxane, deuterated germyl, deuterated aryl, deuterated alkenylaryl, deuterated aryloxy, and deuterated heteroaryl;

a and b are the same or different and are an integer from 0-4, with the proviso that when s=1, a is 0-3, and when t=1, b is 0-3; and s and t are 0 or 1, with the proviso that s+t>0.

All the above-described embodiments for X, $Ar^1$, $Ar^2$, $Ar^3$, $Ar^4$, $R^{3a}$, $R^{4a}$, a, b, s, and t in Formula IX, apply equally to X, $Ar^1$, $Ar^2$, $Ar^3$, $Ar^4$, $R^{3a}$, $R^{4a}$, a, b, s, and t in Formula IX-a.

Any of the above embodiments for Formula IX can be combined with one or more of the other embodiments, so long as they are not mutually exclusive. For example, the embodiment in which a=2 can be combined with the embodiment in which at least one $R^3$ is naphthyl and the embodiment in which at least one $R^3$ has formula a. The same is true for the other non-mutually-exclusive embodiments discussed above. The skilled person would understand which embodiments were mutually exclusive and would thus readily be able to determine the combinations of embodiments that are contemplated by the present application.

In some embodiments, the new compound is an electroactive compound having Formula X

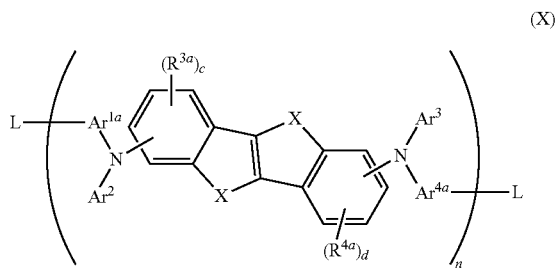

(X)

wherein:

X is O, S, or Se;

$Ar^{1a}$ and $Ar^{4a}$ are the same or different and are selected from the group consisting of aryl groups, heteroaryl groups, and deuterated analogs thereof;

$Ar^2$ and $Ar^3$ are the same or different and are selected from the group consisting of aryl groups, heteroaryl groups, substituted derivatives thereof, and deuterated analogs thereof;

$R^{3a}$ and $R^{4a}$ are the same or different at each occurrence and are selected from the group consisting of D, alkyl, alkoxy, silyl, siloxy, siloxane, germyl, aryl, alkenylaryl, aryloxy, heteroaryl, deuterated alkyl, deuterated alkoxy, deuterated silyl, deuterated siloxy, deuterated siloxane, deuterated germyl, deuterated aryl, deuterated alkenylaryl, deuterated aryloxy, and deuterated heteroaryl;

L is the same or different at each occurrence and is selected from the group consisting of H, D, halogen, aryl, arylamino, crosslinkable groups, deuterated aryl, deuterated arylamino, and deuterated crosslinkable groups;

c and d are the same or different and are an integer from 0-3; and n is an integer greater than 0.

The compound having Formula X can be a small molecule with n=1, an oligomer, or a polymer. As used herein, the term "compound having Formula X" is intended to include small molecules, oligomers and polymers.

In some embodiments of Formula X, n=1 and L is halogen. Such compounds can be useful as monomers for the formation of polymeric compounds. In some embodiments, the halogen is Cl or Br; in some embodiments, Br.

In some embodiments of Formula X, n=1 and L is a crosslinking group or deuterated crosslinking group.

In some embodiments of Formula X, n=1 and L is H or D.

In some embodiments of Formula X, n=2-10.

In some embodiments of Formula X, the compound is a polymer with n>10. In some embodiments, the compound is a polymer with $M_n$>20,000; in some embodiments, $M_n$>50,000.

In some embodiments of Formula X, n>10 and L is selected from aryl, arylamino, crosslinkable groups, and deuterated analogs thereof.

In some embodiments of Formula X, n>10 and L is selected from phenyl, triphenylamino, and deuterated analogs thereof.

In some embodiments of Formula X, $Ar^{1a}=Ar^2$.
In some embodiments of Formula X, $Ar^{1a} \neq Ar^2$.
In some embodiments of Formula X, $Ar^3=Ar^{4a}$.
In some embodiments of Formula X, $Ar^3 \neq Ar^{4a}$.
In some embodiments of Formula X, $Ar^{1a}=Ar^{4a}$.
In some embodiments of Formula X, $Ar^{1a} \neq Ar^{4a}$.
In some embodiments of Formula X, $Ar^2=Ar^3$.
In some embodiments of Formula X, $Ar^2 \neq Ar^3$.

In some embodiments of Formula X, an amino nitrogen is bonded to position 1 on the fused ring core, as defined above.

In some embodiments of Formula X, an amino nitrogen is bonded to position 2 on the fused ring core, as defined above.

In some embodiments of Formula X, an amino nitrogen is bonded to position 3 on the fused ring core, as defined above.

In some embodiments of Formula X, an amino nitrogen is bonded to position 4 on the fused ring core, as defined above.

In some embodiments of Formula X, an amino nitrogen is bonded to position 6 on the fused ring core, as defined above.

In some embodiments of Formula X, an amino nitrogen is bonded to position 7 on the fused ring core, as defined above.

In some embodiments of Formula X, an amino nitrogen is bonded to position 8 on the fused ring core, as defined above.

In some embodiments of Formula X, an amino nitrogen is bonded to position 9 on the fused ring core, as defined above.

In some embodiments of Formula X, $Ar^{1a}$ is a hydrocarbon aryl group having 6-36 ring carbons. The hydrocarbon aryl group can include one or more single ring groups bonded together, one or more fused rings, or combinations thereof.

In some embodiments of Formula X, $Ar^{1a}$ has no heteroaromatic groups.

In some embodiments of Formula X, $Ar^{1a}$ has Formula d, as defined above.

In some embodiments of Formula X, $Ar^{1a}$ has Formula e, as defined above.

In some embodiments of Formula X, $Ar^{1a}$ is selected from the group consisting of 1-naphthyl, 2-naphthyl, anthracenyl, fluorenyl, deuterated analogs thereof, and derivatives thereof having one or more substituents selected from the group consisting of fluoro, alkyl, alkoxy, silyl, siloxy, germyl, a substituent with a crosslinking group, and deuterated analogs thereof.

All of the above-described embodiments for $Ar^{1a}$ in Formula X apply equally to $Ar^{4a}$ in Formula X.

All the above-described embodiments for X, $Ar^2$, $Ar^3$, $R^{3a}$, $R^{4a}$, s, and t in Formula IX, apply equally to X, $Ar^2$, $Ar^3$, $R^{3a}$, $R^{4a}$, s, and t in Formula X.

All of the above-described embodiments for c and d in Formula II apply equally to c and d in Formula X.

In some embodiments, the compound of Formula II has Formula II-a (X-a)

$$L \left( \begin{array}{c} Ar^{1a} \\ N \\ Ar^2 \end{array} \begin{array}{c} (R^{3a})_c \\ X \\ (R^{4a})_d \end{array} \begin{array}{c} Ar^3 \\ N \\ Ar^{4a} \end{array} L \right)_n$$

wherein:

X is O, S, or Se;

$Ar^{1a}$ and $Ar^{4a}$ are the same or different and are selected from the group consisting of aryl groups, heteroaryl groups, substituted derivatives thereof, and deuterated analogs thereof;

$Ar^2$ and $Ar^3$ are the same or different and are selected from the group consisting of aryl groups, heteroaryl groups, and deuterated analogs thereof;

$R^{3a}$ and $R^{4a}$ are the same or different at each occurrence and are selected from the group consisting of D, alkyl, alkoxy, silyl, siloxy, siloxane, germyl, aryl, alkenylaryl, aryloxy, heteroaryl, deuterated alkyl, deuterated alkoxy, deuterated silyl, deuterated siloxy, deuterated siloxane, deuterated germyl, deuterated aryl, deuterated alkenylaryl, deuterated aryloxy, and deuterated heteroaryl;

L is the same or different at each occurrence and is selected from the group consisting of H, D, halogen, aryl, arylamino, crosslinkable groups, deuterated aryl, deuterated arylamino, and deuterated crosslinkable groups;

c and d are the same or different and are an integer from 0-3; and n is an integer greater than 0.

All of the above-described embodiments for X, $Ar^{1a}$, $Ar^2$, $Ar^3$, $Ar^{4a}$, $R^{3a}$, $R^{4a}$, c, d, and n in Formula X, apply equally to X, $Ar^{1a}$, $Ar^2$, $Ar^3$, $Ar^{4a}$, $R^{3a}$, $R^{4a}$, c, d, and n in Formula X-a.

Any of the above embodiments for Formula X can be combined with one or more of the other embodiments, so long as they are not mutually exclusive. For example, the embodiment in which n>10 can be combined with the embodiment in which X=S and the embodiment in which $Ar^{1a}$ has formula c. The same is true for the other non-mutually-exclusive embodiments discussed above. The skilled person would understand which embodiments were mutually exclusive and would thus readily be able to determine the combinations of embodiments that are contemplated by the present application.

The compounds having Formula IX or Formula X can be made using known coupling techniques, as described above.

Some non-limiting examples of compounds having Formula IX are shown below.

Compound IX-1

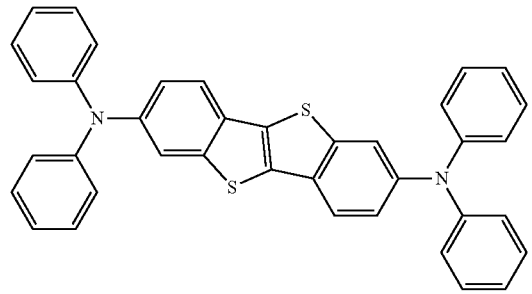

Compound IX-2

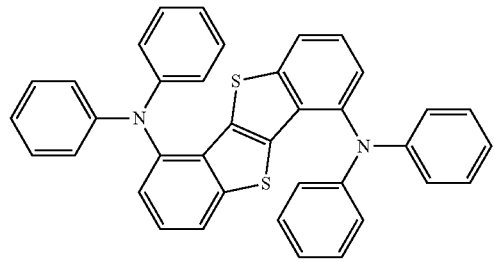

Compound IX-3

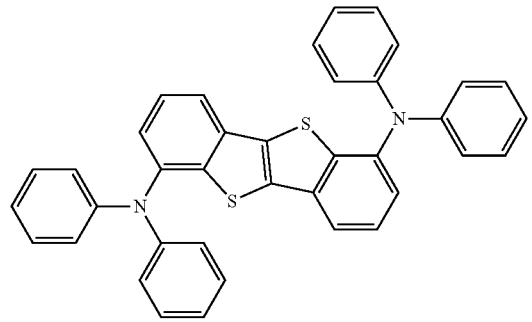

Compound IX-4

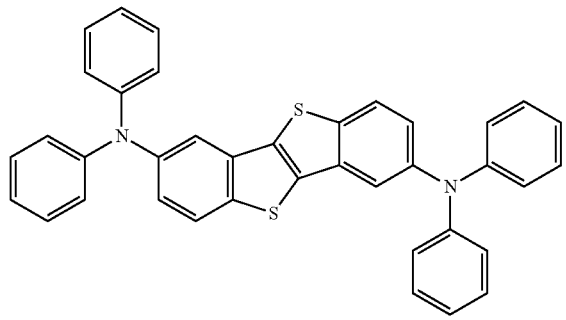

-continued
Compound IX-5
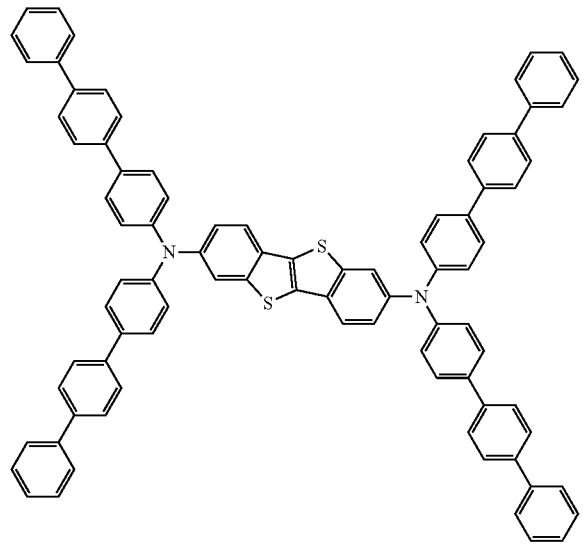
Compound IX-6
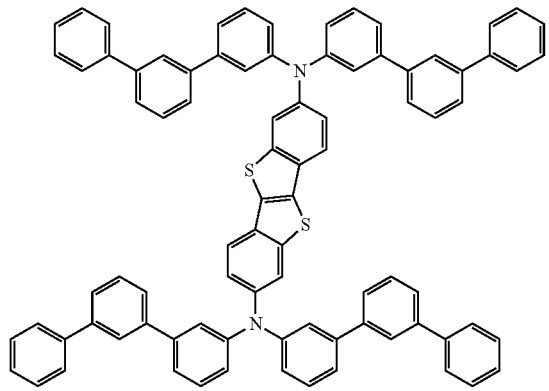
Compound IX-7
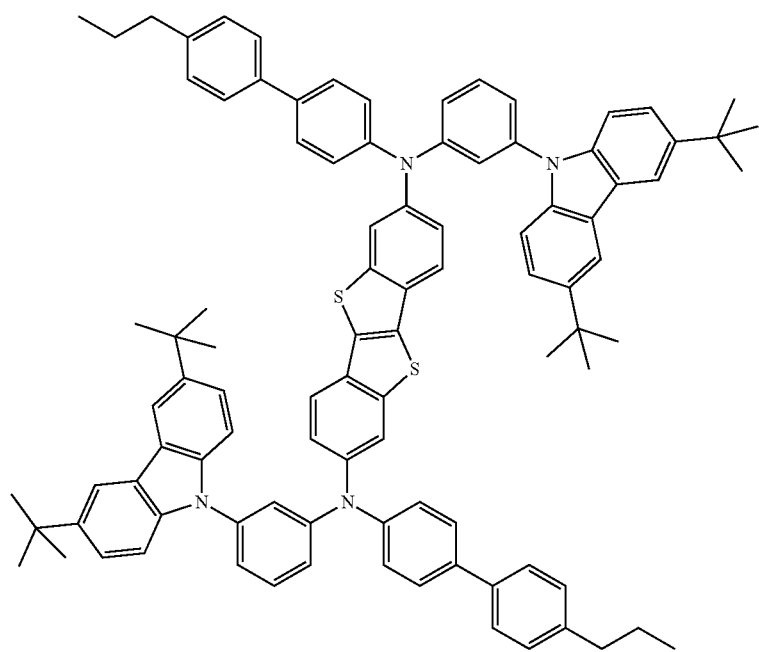

Compound IX-8
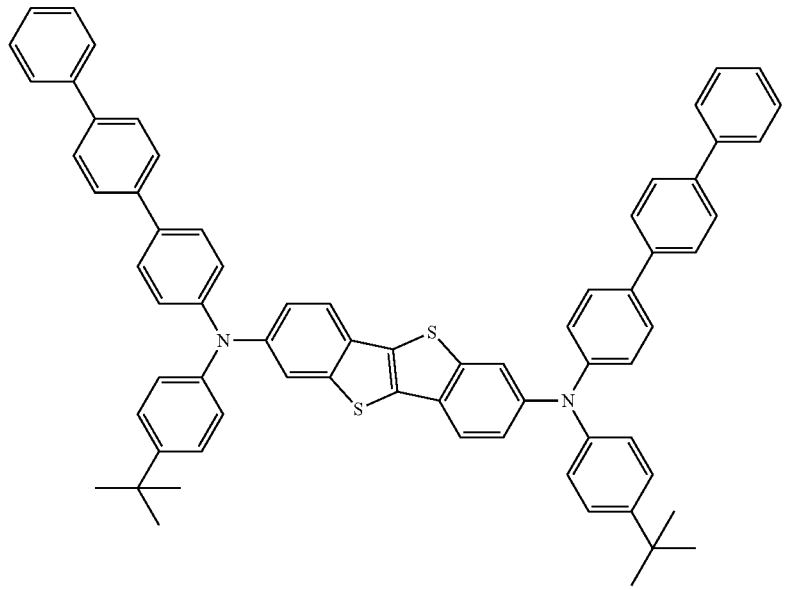
Compound IX-9
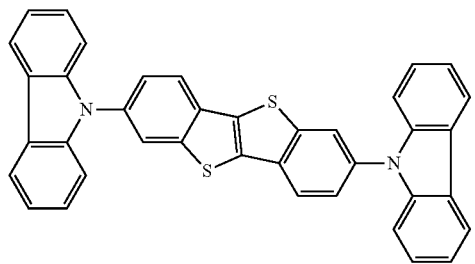
Compound IX-10
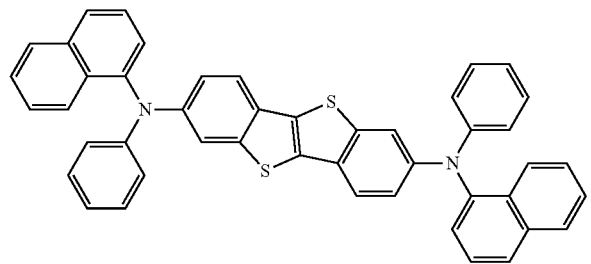
Compound IX-11
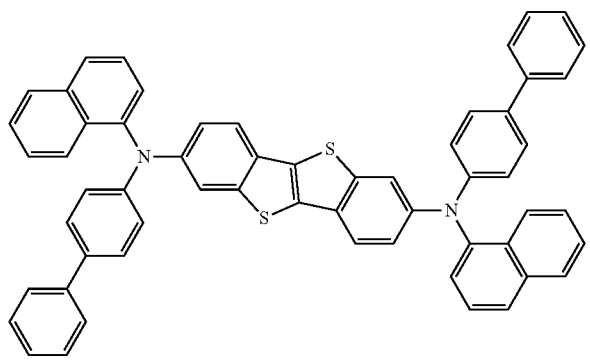
Compound IX-12
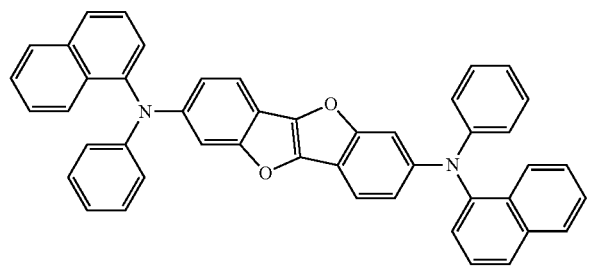

7. Copolymer Having at Least One Monomeric Unit of Formula XI and Copolymer Having Formula XII In some embodiments, the new compound is a copolymer having at least one monomeric unit of Formula XI

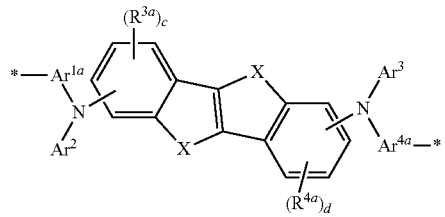
(XI)

wherein:
- X is O, S, or Se;
- $Ar^{1a}$ and $Ar^{4a}$ are the same or different and are selected from the group consisting of aryl groups, heteroaryl groups, substituted derivatives thereof, and deuterated analogs thereof;
- $Ar^2$ and $Ar^3$ are the same or different and are selected from the group consisting of aryl groups, heteroaryl groups, substituted derivatives thereof, and deuterated analogs thereof;
- $R^{3a}$ and $R^{4a}$ are the same or different at each occurrence and are selected from the group consisting of D, alkyl, alkoxy, silyl, siloxy, siloxane, germyl, aryl, alkenylaryl, aryloxy, heteroaryl, deuterated alkyl, deuterated alkoxy, deuterated silyl, deuterated siloxy, deuterated siloxane, deuterated germyl, deuterated aryl, deuterated alkenylaryl, deuterated aryloxy, and deuterated heteroaryl; and
- * represents a point of attachment in the copolymer.

In some embodiments of Formula XI, an amino nitrogen is bonded to position 1 on the fused ring core, as defined above.

In some embodiments of Formula XI, an amino nitrogen is bonded to position 2 on the fused ring core, as defined above.

In some embodiments of Formula XI, an amino nitrogen is bonded to position 3 on the fused ring core, as defined above.

In some embodiments of Formula XI, an amino nitrogen is bonded to position 4 on the fused ring core, as defined above.

In some embodiments of Formula XI, an amino nitrogen is bonded to position 6 on the fused ring core, as defined above.

In some embodiments of Formula XI, an amino nitrogen is bonded to position 7 on the fused ring core, as defined above.

In some embodiments of Formula XI, an amino nitrogen is bonded to position 8 on the fused ring core, as defined above.

In some embodiments of Formula XI, an amino nitrogen is bonded to position 9 on the fused ring core, as defined above.

All of the above-described embodiments for X, $Ar^{1a}$, $Ar^2$, $Ar^3$, $Ar^{4a}$, $R^{3a}$, $R^{4a}$, c, and d in Formula X, apply equally to X, $Ar^{1a}$, $Ar^2$, $Ar^3$, $Ar^{4a}$, $R^{3a}$, $R^{4a}$, c, and d in Formula XI.

In some embodiments, the copolymer has Formula XII

Formula XII where:
- L is the same or different at each occurrence and is selected from the group consisting of H, D, halogen, aryl, arylamino, crosslinkable groups, deuterated aryl, deuterated arylamino, and deuterated crosslinkable groups;
- M is a conjugated moiety;
- Q2 is a monomeric unit having Formula XI; and
- w and z represent non-zero mole fractions such that w+z=1.

In Formula XII, the "Q" and "M" units can be ordered in a regular alternating pattern, in blocks of like monomers, or randomly arranged.

All of the above-described embodiments for $L^1$ in Formula VI apply equally to L in Formula XII.

All of the above-described embodiments for M and w in Formula VI apply equally to M and w in Formula XII.

Any of the above embodiments for Formula XII can be combined with one or more of the other embodiments, so long as they are not mutually exclusive. For example, the embodiment in which $Ar^{1a}=Ar^{4a}$ in Q2 can be combined with the embodiment in which M has formula M1. The same is true for the other non-mutually-exclusive embodiments discussed above. The skilled person would understand which embodiments were mutually exclusive and would thus readily be able to determine the combinations of embodiments that are contemplated by the present application.

The copolymer having Formula XII can be made using known coupling techniques and polymerization techniques. The deuterated analog materials can be made as described above.

Some non-limiting examples of copolymers having Formula XII are shown below.

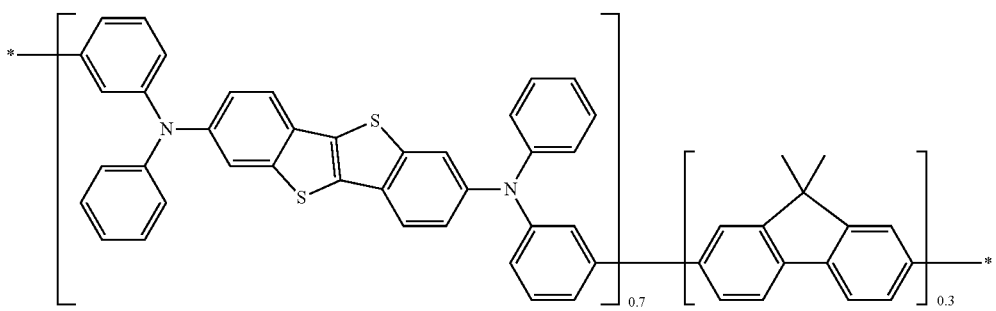

Compound XII-1

The * indicates a point of attachment in the copolymer.

8. Electronic Devices

Organic electronic devices that may benefit from having one or more layers including at least one compound as described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), (4) devices that convert light of one wavelength to light of a longer wavelength, (e.g., a down-converting phosphor device); and (5) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

One illustration of an organic electronic device structure including at least one of the new compounds, polymers or copolymers described herein is shown in FIG. 1. The device 100 has a first electrical contact layer, an anode layer 110 and a second electrical contact layer, a cathode layer 160, and a photoactive layer 140 between them. Additional layers may optionally be present. Adjacent to the anode may be a hole injection layer 120, sometimes referred to as a buffer layer. Adjacent to the hole injection layer may be a hole transport layer 130, including hole transport material. Adjacent to the cathode may be an electron transport layer 150, including an electron transport material. As an option, devices may use one or more additional hole injection or hole transport layers (not shown) next to the anode 110 and/or one or more additional electron injection or electron transport layers (not shown) next to the cathode 160. Layers 120 through 150 are individually and collectively referred to as the organic active layers.

Figure 2:
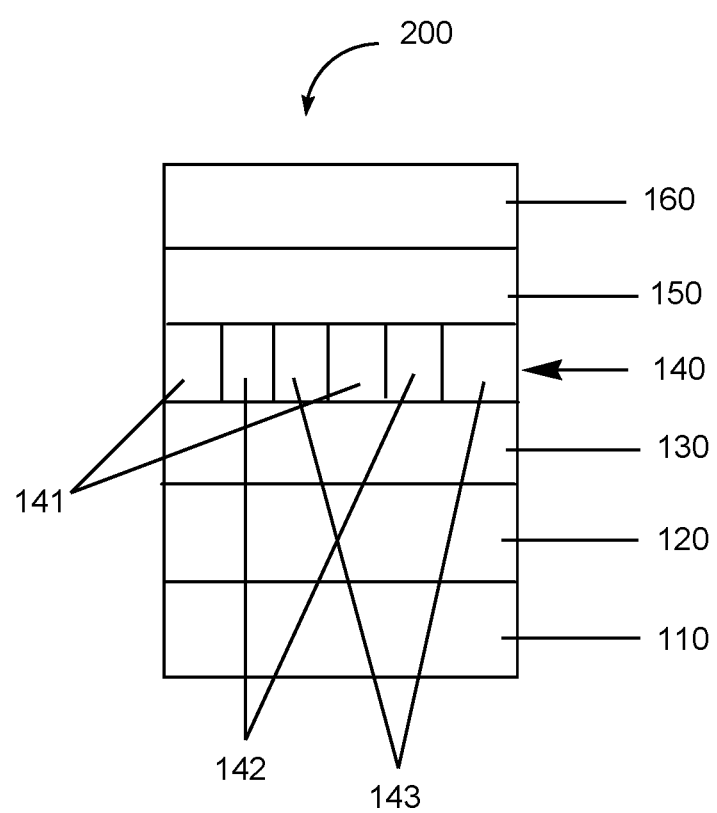
FIG. 2 includes an illustration of another example of an organic electronic device.

In some embodiments, in order to achieve full color, the light-emitting layer is pixellated, with subpixel units for each of the different colors. An illustration of a pixellated device including at least one of the new compounds, polymers or copolymers described herein is shown in FIG. 2. The device 200 has anode 110, hole injection layer 120, hole transport layer 130, photoactive layer 140, electron transport layer 150, and cathode 160. The photoactive layer is divided into subpixels 141, 142, 143, which are repeated across the layer. In some embodiments, the subpixels represent red, blue and green color emission. Although three different subpixel units are depicted in FIG. 2, two or more than three subpixel units may be used.

The different layers will be discussed further herein with reference to FIG. 1. However, the discussion applies to FIG. 2 and other configurations as well.

In some embodiments, the different layers have the following range of thicknesses: anode 110, 500-5000 Å, in some embodiments, 1000-2000 Å; hole injection layer 120, 50-2000 Å, in some embodiments, 200-1000 Å; hole transport layer 130, 50-3000 Å, in some embodiments, 200-2000 Å; photoactive layer 140, 10-2000 Å, in some embodiments, 100-1000 Å; electron transport layer 150, 50-2000 Å, in some embodiments, 100-1000 Å; cathode 160, 200-10000 Å, in some embodiments, 300-5000 Å. The desired ratio of layer thicknesses will depend on the exact nature of the materials used.

One or more of the new the compound having Formula I, Formula II, Formula III, Formula VIII, Formula IX, or Formula X, the copolymer having at least one monomeric unit of Formula IV, Formula V, or Formula XI, or the copolymer having Formula VI, Formula VII, or Formula XII described herein may be present in one or more of the electroactive layers of a device.

In some embodiments, the new compound having Formula I, Formula II, Formula III, Formula VIII, Formula IX, or Formula X, the copolymer having at least one monomeric unit of Formula IV, Formula V, or Formula XI, or the copolymer having Formula VI, Formula VII, or Formula XII are useful as photoactive materials in layer 140. In some embodiments, the new compounds, polymers and copolymers described herein are present as photoactive dopant materials in one or more host materials. The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material. The term "host material" is intended to mean a material to which a dopant is added. The host material may or may not have electronic characteristic(s) or the ability to emit, receive, or filter radiation. In some embodiments, the host material is present in higher concentration.

In some embodiments, the compound having Formula I, Formula II, Formula III, Formula VIII, Formula IX, or Formula X, the copolymer having at least one monomeric unit of Formula IV, Formula V, or Formula XI, or the copolymer having Formula VI, Formula VII, or Formula XII is useful as a host material for photoactive dopant materials in photoactive layer 140. The new compounds, polymers and copolymers described herein can be used alone or in combination with one or more additional host materials.

In some embodiments, the compound having Formula I, Formula II, Formula III, Formula VIII, Formula IX, or Formula X, the copolymer having at least one monomeric unit of Formula IV, Formula V, or Formula XI, or the copolymer having Formula VI, Formula VII, or Formula XII is useful as an electron transport material in layer 150.

In some embodiments, an organic electronic device includes an anode, a cathode, and at least one organic active layer therebetween, where the organic active layer includes a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII.

In some embodiments, an organic electronic device includes an anode, a cathode, and a photoactive layer therebetween, where the photoactive layer includes a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII.

In some embodiments, an organic electronic device includes an anode, a cathode, and a photoactive layer therebetween, and further includes an additional organic active layer including a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII. In some embodiments, the additional organic active layer is an electron transport layer.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also include an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

Optional hole injection layer 120 includes hole injection materials. The term "hole injection layer" or "hole injection material" is intended to mean electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules, and may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like. The hole injection layer 120 can include charge transfer compounds, and the like, such as copper phthalocyanine and the tetrathiafulvalene-tetracyanoquinodimethane system (TTF-TCNQ). In some embodiments, the hole injection layer 120 is made from a dispersion of a conducting polymer and a colloid-forming polymeric acid. Such materials have been described in, for example, published U.S. patent applications 2004-0102577, 2004-0127637, and 2005-0205860.

Layer 130 includes hole transport material.

In some embodiments, layer 130 includes a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII. In some embodiments, layer 130 includes only a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII, where additional materials that would materially alter the principle of operation or the distinguishing characteristics of the layer are not present.

In some embodiments, layer 130 includes other hole transport materials. Examples of hole transport materials for the hole transport layer have been summarized for example, in Kirk-Othmer Encyclopedia of Chemical Technology, Fourth Edition, Vol. 18, p. 837-860, 1996, by Y. Wang. Both hole transporting small molecules and polymers can be used. Commonly used hole transporting molecules include, but are not limited to: 4,4',4"-tris(N,N-diphenyl-amino)-triphenylamine (TDATA); 4,4',4"-tris(N-3-methylphenyl-N-phenyl-amino)-triphenylamine (MTDATA); N,N'-diphenyl-N,N'-bis(3-methylphenyl)-[1,1'-biphenyl]-4,4'-diamine (TPD); 4,4'-bis(carbazol-9-yl)biphenyl (CBP); 1,3-bis(carbazol-9-yl)benzene (mCP); 1,1-bis[(di-4-tolylamino) phenyl]cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (PDA); α-phenyl-4-N,N-diphenylaminostyrene (TPS); p-(diethylamino)benzaldehyde diphenylhydrazone (DEH); triphenylamine (TPA); bis[4-(N, N-diethylamino)-2-methylphenyl](4-methylphenyl)methane (MPMP); 1-phenyl-3-[p-(diethylamino)styryl]-5-[p-(diethylamino)phenyl]pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); N,N'-bis(naphthalen-1-yl)-N,N'-bis-(phenyl)benzidine (α-NPB); and porphyrinic compounds, such as copper phthalocyanine. Commonly used hole transporting polymers include, but are not limited to, polyvinylcarbazole, (phenylmethyl)polysilane, poly(dioxythiophenes), polyanilines, and polypyrroles. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

Depending upon the application of the device, the photoactive layer 140 can be a light-emitting layer that is activated by an applied voltage (such as in a light-emitting diode or light-emitting electrochemical cell), a layer of material that absorbs light and emits light having a longer wavelength (such as in a down-converting phosphor device), or a layer of material that responds to radiant energy and generates a signal with or without an applied bias voltage (such as in a photodetector or photovoltaic device).

In some embodiments, the photoactive layer includes a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII as a photoactive material. In some embodiments, the photoactive layer further comprises a host material. Examples of host materials include, but are not limited to, chrysenes, phenanthrenes, triphenylenes, phenanthrolines, naphthalenes, anthracenes, quinolines, isoquinolines, quinoxalines, phenylpyridines, indolocarbazoles, furans, benzofurans, dibenzofurans, benzodifurans, and metal quinolinate complexes. In some embodiments, the host materials are deuterated.

In some embodiments, the photoactive layer includes a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII as host material and additionally includes a photoactive dopant. The photoactive dopant can be an organic electroluminescent ("EL") material. Any EL material can be used in the devices, including, but not limited to, small molecule organic fluorescent compounds, fluorescent and phosphorescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. In some cases the small molecule fluorescent or organometallic materials are deposited as a dopant with a host material to improve processing and/or electronic properties. Examples of conjugated polymers include, but are not limited to poly(phenylenevinylenes), polyfluorenes, poly(spirobifluorenes), polythiophenes, poly (p-phenylenes), copolymers thereof, and mixtures thereof.

In some embodiments, the photoactive layer further includes a second host material. Examples of second host materials include, but are not limited to, chrysenes, phenanthrenes, triphenylenes, phenanthrolines, naphthalenes, anthracenes, quinolines, isoquinolines, quinoxalines, phenylpyridines, indolocarbazoles, furans, benzofurans, dibenzofurans, benzodifurans, and metal quinolinate complexes.

In some embodiments, photoactive layer 140 includes only a host which is a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII and a photoactive dopant, where additional materials that would materially alter the principle of operation or the distinguishing characteristics of the layer are not present.

In some embodiments, photoactive layer 140 includes a photoactive dopant, a host material which is a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII, and a second host material. In some embodiments, photoactive layer 140 includes only a photoactive dopant, a first host material which is a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII, and a second host material, where additional materials that would materially alter the principle of operation or the distinguishing characteristics of the layer are not present.

In some embodiments, the weight ratio of total host material to dopant is in the range of 99.5:0.5 to 25:75; in some embodiments, 99:1 to 30:70; in some embodiments, 95:5 to 60:40; in some embodiments, 90:10 to 70:30.

In some embodiments, the weight ratio of first host material to second host material is in the range of 10:90 to 90:10; in some embodiments, 75:25 to 25:75; in some embodiments, 60:40 to 40:60.

Optional layer 150 can function both to facilitate electron transport, and also serve as a confinement layer to prevent quenching of the exciton at layer interfaces. Preferably, this layer promotes electron mobility and reduces exciton quenching.

In some embodiments, layer 150 includes a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII. In some embodiments, layer 150 includes only a compound having Formula I, Formula II, Formula III, Formula VIII, Formula IX, or Formula X, a copolymer having at least one monomeric unit of Formula IV, Formula V, or Formula XI, or a copolymer having Formula VI, Formula VII, or Formula XII where additional materials that would materially alter the principle of operation or the distinguishing characteristics of the layer are not present.

In some embodiments, layer 150 includes other electron transport materials. Examples of electron transport materials which can be used in the optional electron transport layer 150, include metal chelated oxinoid compounds, including metal quinolate derivatives such as tris(8-hydroxyquinolato) aluminum (AlQ), bis(2-methyl-8-quinolinolato)(p-phenylphenolato) aluminum (BAlq), tetrakis-(8-hydroxyquinolato) hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); triazines; fullerenes; and mixtures thereof. In some embodiments, the electron transport material is selected from the group consisting of metal quinolates and phenanthroline derivatives. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

An optional electron injection layer may be deposited over the electron transport layer. Examples of electron injection materials include, but are not limited to, Li-containing organometallic compounds, LiF, $Li_2O$, Li quinolate, Cs-containing organometallic compounds, CsF, $Cs_2O$, and $Cs_2CO_3$. This layer may react with the underlying electron transport layer, the overlying cathode, or both. When an electron injection layer is present, the amount of material deposited is generally in the range of 1-100 Å, in some embodiments 1-10 Å.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device layers can be formed by any deposition technique, or combinations of techniques, including vapor deposition, liquid deposition, and thermal transfer. Substrates such as glass, plastics, and metals can be used. Conventional vapor deposition techniques can be used, such as thermal evaporation, chemical vapor deposition, and the like. The organic layers can be applied from solutions or dispersions in suitable solvents, using conventional coating or printing techniques, including but not limited to spin-coating, dip-coating, roll-to-roll techniques, ink-jet printing, continuous nozzle printing, screen-printing, gravure printing and the like.

For liquid deposition methods, a suitable solvent for a particular compound or related class of compounds can be readily determined by one skilled in the art. For some applications, it is desirable that the compounds be dissolved in non-aqueous solvents. Such non-aqueous solvents can be relatively polar, such as $C_1$ to $C_{20}$ alcohols, ethers, and acid esters, or can be relatively non-polar such as $C_1$ to $C_{12}$ alkanes or aromatics such as toluene, xylenes, trifluorotoluene and the like. Other suitable liquids for use in making the liquid composition, either as a solution or dispersion as described herein, including the new compounds, includes, but not limited to, chlorinated hydrocarbons (such as methylene chloride, chloroform, chlorobenzene), aromatic hydrocarbons (such as substituted and non-substituted toluenes and xylenes), including triflurotoluene), polar solvents (such as tetrahydrofuran (THP), N-methyl pyrrolidone) esters (such as ethylacetate) alcohols (isopropanol), ketones (cyclopentatone) and mixtures thereof. Suitable solvents for electroluminescent materials have been described in, for example, published PCT application WO 2007/145979.

In some embodiments, the device is fabricated by liquid deposition of the hole injection layer, the hole transport layer, and the photoactive layer, and by vapor deposition of the anode, the electron transport layer, an electron injection layer and the cathode.

It is understood that the efficiency of devices made with the new compositions described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

In some embodiments, the device has the following structure, in order: anode, hole injection layer, hole transport layer, photoactive layer, electron transport layer, electron injection layer, cathode.

Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further described in the following examples, which do not limit the scope of the invention described in the claims.

Synthesis Example 1

This example illustrates the preparation of the indoloindole core structure.

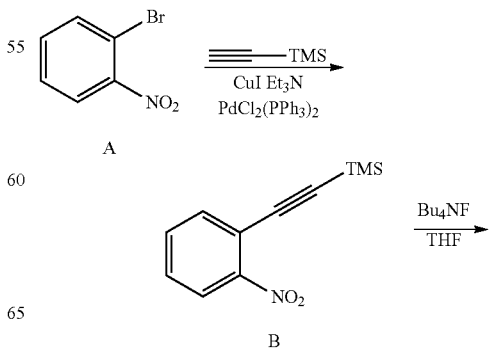

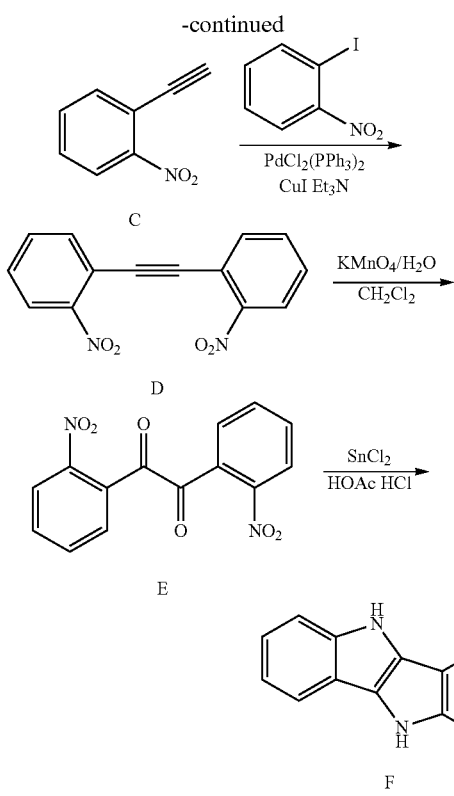

To a RBF (2000 mL) was added compound A (100 g, 0.495 mol), CuI (1 g) and Pd(PPh$_3$)$_2$Cl$_2$ (2.5 g), followed by the addition of Et$_3$N (1000 mL). The mixture was purged with N$_2$ for 10 min. Then Ethynyl-trimethyl-silane (58 g, 0.591 mol) was added dropwise. The mixture was stirred for 4 hours. The Et$_3$N was removed on vacuum. The residue diluted with water, Extracted with MTBE, washed with water, concentrated on vacuum to give the desired product which was used for next step. (108 g, 99%)

To a 3-neck RBF (2000 mL) was added compound B (108 g, 0.492 mol), followed by the addition of THF (500 mL). The mixture was cooled to −10° C. under N$_2$. The Bu$_4$NF in THF was added dropwise below 0° C. After addition the reaction mixture was warmed to ambient temperature and stirred for two hours. TLC checked the reaction was completed. The reaction mixture was poured into water while keeping the temperature below 30° C., extracted with MTBE, washed with water, dried with sulfate sodium. After filtration the filtrate was concentrated on vacuum to give the crude product. Purification by Silica gel column chromatography gave the product (48 g, yield: 66%).

To a RBF (1000 ml) was added compound C (25 g, 0.17 gmol), followed by the addition of Et$_3$N (600 ml). The mixture was purged with N$_2$ for 10 min. A catalyst amount of Pd (PPh$_3$)$_2$Cl$_2$ (200 mg) and CuI (35 mg) were added. The mixture was stirred for 6 hours, filtered and the solid was collected. The solid was reflux in ethanol (500 mL) for 2 hours and the solid was collected to give the crude product. The material was purified with crystallization from toluene to give the product (42 g, 92%).

Into a RBF (2000 ml) was added compound D (20 g, 55.2 mmol), TBAB (2 g), followed by the addition of CH$_2$Cl$_2$ (600 ml) and HOAc (30 ml). Then KMnO$_4$ (35.2 g, 223 mmole) in the water (600 mL) was added. The mixture was refluxed for 5 hours under N$_2$. An aqueous NaHSO$_3$ solution was added dropwise until the mixture became clear. The organic layer was separated and concentrated under vacuum to give the product as a yellow solid. (20 g, 89%)

Into a RBF (1000 mL) was added SnCl$_2$.2H$_2$O (63 g, 280 mmol), HOAc (300 ml), aqueous HCl (6N, 300 mL). The mixture was heated to reflux. The compound E was added slowly. The mixture was stirred for another one hour. After cooling to ambient temperature, the solid was collected by filtration, washed with MeOH and dried under vacuum to give the desired product F as a white solid. (4.2 g, 61%)

Synthesis Example 2

This example illustrates the synthesis of a compound having Formula I, Compound I-1.

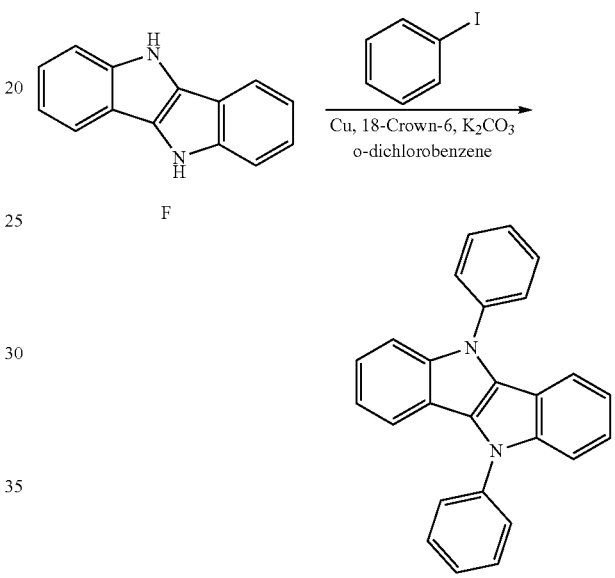

A mixture of compound F from Synthesis Example 1 (15 g, 72.7 mmo), iodobenzene (59 g, 289 mmol), Cu (3.7 g, 59 mmol), 18-crown-6 (7.5 g), K$_2$CO$_3$ (59 g, 0.43) in o-DCB was heated to reflux for 4 hours under N$_2$. The mixture was cooled to ambient temperature and diluted with THF. After filtration, the filtrate was concentrated to a final volume (50 ml), added slowly to 500 ml Methanol. The precipitate was collected by filtration to give the product (15 g, 57%).

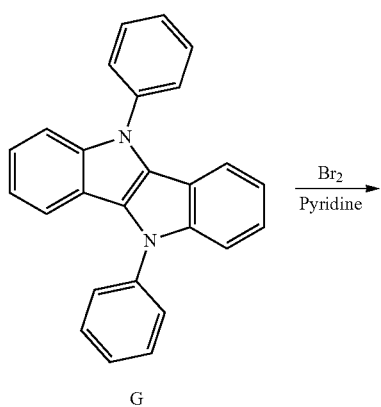

-continued

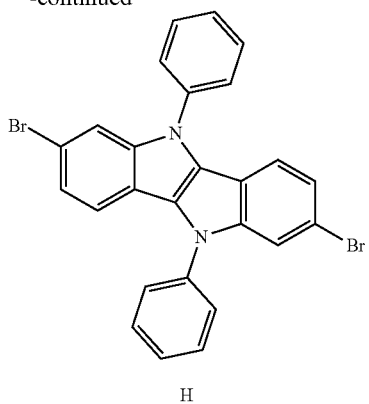

H

Into a RBF (500 mL) was added compound G (10 g, 28 mmol), followed by the addition of pyridine (130 mL) and $CCl_4$ (20 mL). The mixture was cooled to 0° C. and bromine in $CCl_4$ (1N) was dropwise added. The mixture was stirred overnight, added slowly to 500 ml Methanol with stirring. The precipitate was collected by filtration to give the product. (12 g, 84%)

To a mixture of H and (E)-4,4,5,5-tetramethyl-2-(4-pentylstyryl)-1,3,2-dioxaborolane (1.58 g) in toluene (50 mL) was added aqueous $Na_2CO_3$ (2M, 1.27 g, 6 mL of $H_2O$) followed by the addition of Aliquat 336 (0.49 g). The mixture was bubbled with nitrogen for 15 min, then $Pd(PPh_3)_4$ (55 mg) was added. The mixture was heated at 90° C. (oil bath) for 18 h under a nitrogen atmosphere. After cooling to ambient temperature, the mixture (green) was poured into MeOH. The solid was filtered off and purified by Silica gel column chromatography to give the product (0.6 g) as a bright yellow solid. The compound structure was confirmed by NMR analysis.

Synthesis Example 3

This example illustrates the synthesis of a compound having Formula I, Compound I-2.

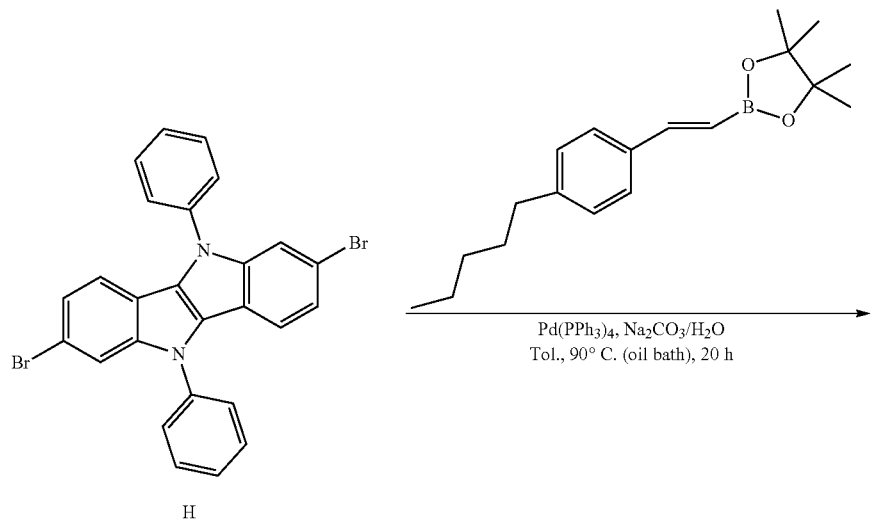

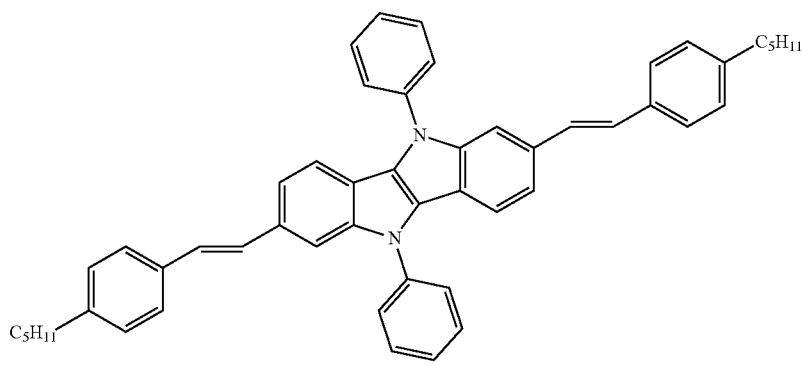

Compound I-1

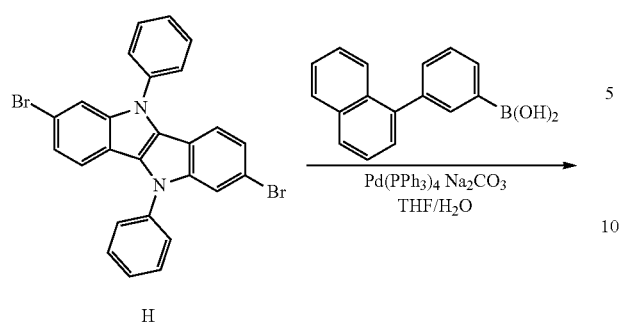

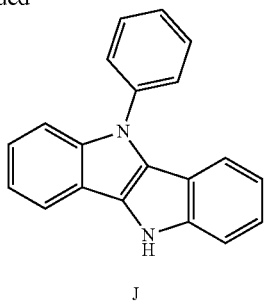

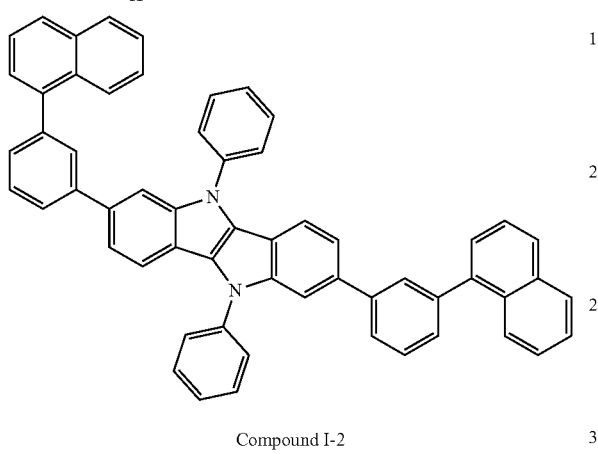

Compound I-2

A mixture of compound F (5 g, 24.27 mmol) from Example 1, iodobenzene (5 g, 24.51 mmol), Cu (1.24 g), 18-crown-6 (2.5 g), K₂CO₃ in o-DCB was heated to reflux for 4 hours under N₂. The mixture was cooled to ambient temperature and diluted with THF. This was filtered, concentrated, and purified by Silica column chromatography (CHCl3/Hexane (1/4~1/2)) to give the product (2 g, yield: 30%).

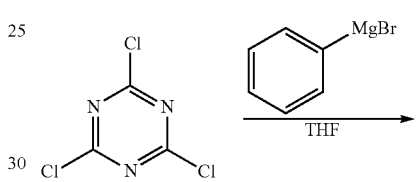

Into a RBF (500 ml) was added compound H (5 g, 9.7 mmol) from Example 2, (3-(naphthalen-1-yl)phenyl)boronic acid (7.25 g, 30 mmol), followed by the addition of toluene (150 mL). The mixture was purged with N₂ for 10 min. Then K₂CO₃ (6.9 g, 50 mmole) in the water (30 mL) was added. The mixture was purged with N₂ for 10 min. A catalytic amount of Pd(PPh₃)₄ (200 mg) was added. The mixture was refluxed overnight. After separation of the aqueous phase, THF layer was filtered through silica pad to remove the insoluble materials. The filtrate was concentrated to a final volume of (50 ml), added slowly to 500 ml methanol with stirring. The precipitate was collected by filtration to give the crude product, which was purified by Silica gel column chromatography (100% Hexane first, then the gradient of CHCl₃/Hexane (1/4~1/2) to give the product (6.2 g, yield: 85%). The compound structure was confirmed by NMR analysis.

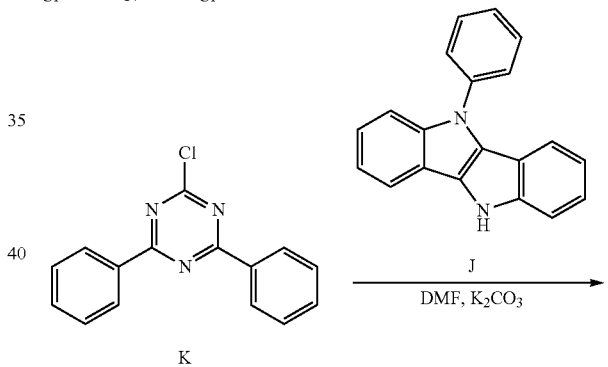

Synthesis Example 4

This example illustrates the synthesis of a compound having Formula I, Compound I-3.

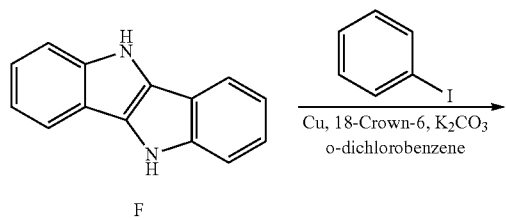

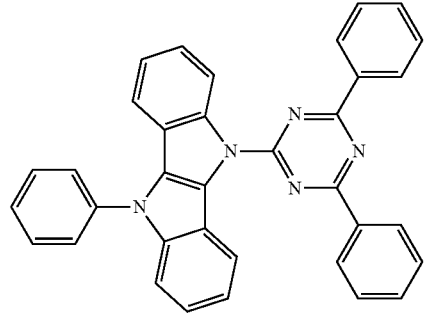

Compound I-3

A mixture of compound J (1 g, 24.27 mmol), compound K (1.14 g, 4.25 mmol), and K₂CO₃ in DMF was heated to 90° C. for 4 hours under N₂. The mixture was cooled to ambient temperature and diluted with water. This was filtered to give the crude product as a yellow solid. This was purified by Silica gel column chromatography (CHCl₃/Hexane (1/4~1/2)) to give the product (1.5 g, yield: 82%). The compound structure was confirmed by NMR analysis.

Synthesis Example 5

This example illustrates the synthesis of a compound having Formula I, Compound I-4.

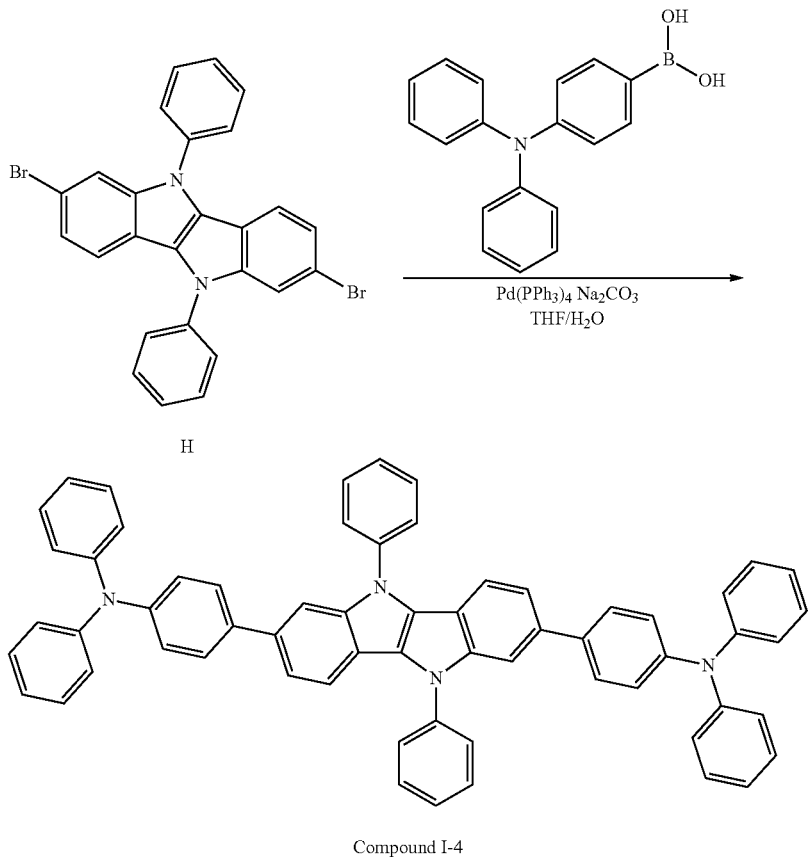

Compound I-4

Into a RBF (25 mL) was added compound H (0.2 g, 0.39 mmol), (4-(diphenylamino)phenyl)boronic acid (0.39 g, 1.36 mmol), followed by the addition of toluene (20 mL). The mixture was purged with N₂ for 10 min. Then Na₂CO₃ (0.16, 1.54 mmole) in water (30 mL) was added. The mixture was continued to purge with N₂ for 10 min. A catalyst amount of Pd(PPh₃)₄ (20 mg) was added. The mixture was refluxed overnight. After separation of the aqueous phase, the THF layer was filtered through Silica pad to remove the insoluble materials. The filtrate was concentrated to a final volume (50 ml), added slowly to methanol (500 mL). The precipitate was collected by filtration to give the crude product, which was purified by Silica gel column chromatography (100% Hexane to CHCl3/Hexane (1/4~1/2)) to give the product (0.2 g, yield: 80%) The compound structure was confirmed by NMR analysis.

Synthesis Example 6

This example illustrates the synthesis of a compound having Formula I, Compound I-18.

a. Synthesis of N-(3,5-dimethylphenyl)-[1,1':3',1"-terphenyl]-3-amine

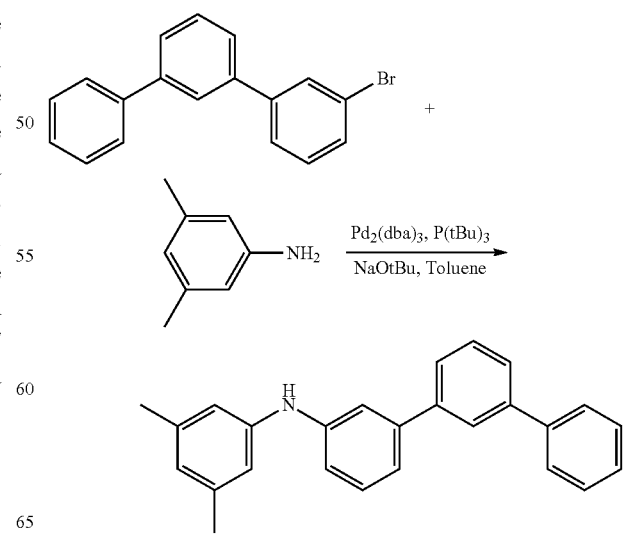

3-bromo-3'-phenylbiphenyl (10 g, 31.53 mmol), 3,5-dimethylaniline (4.09 g, 33.10 mmol), tris (dibenzylideneacetone) dipalladium (577 mg, 0.63 mmol), tri-tert-butylphosphine (255 mg, 1.26 mmol) and anhydrous toluene (250 mL) were taken in a 500 mL flask under nitrogen and stirred for 5 min. To this solution sodium t-butoxide (3.33 g, 34.68 mmol) was added in small portions with stirring at room temperature and the resulting solution allowed to stir at 80° C. for 1 hour. Reaction was shown complete by UPLC analysis. After cooling, the mixture was filtered and passed through a layer of Silica gel eluted with toluene. The solvent was removed and the residue was dissolved in chloroform and hexane (1/2) and separated on a Silica gel column eluted with chloroform/hexane gradient. Fractions were identified by UPLC and collected. The solvent was evaporated to give 7.19 g product as colorless thick oil in 97% purity; 4.23 g material was recovered with about 80% purity. The structure of the product was confirmed by NMR analysis.

b. Synthesis of N2,N7-di([1,1':3',1"-terphenyl]-3-yl)-N2,N7-bis(3,5-dimethylphenyl)-5,10-diphenyl-5,10-dihydroindolo[3,2-b]indole-2,7-diamine, Compound I-18

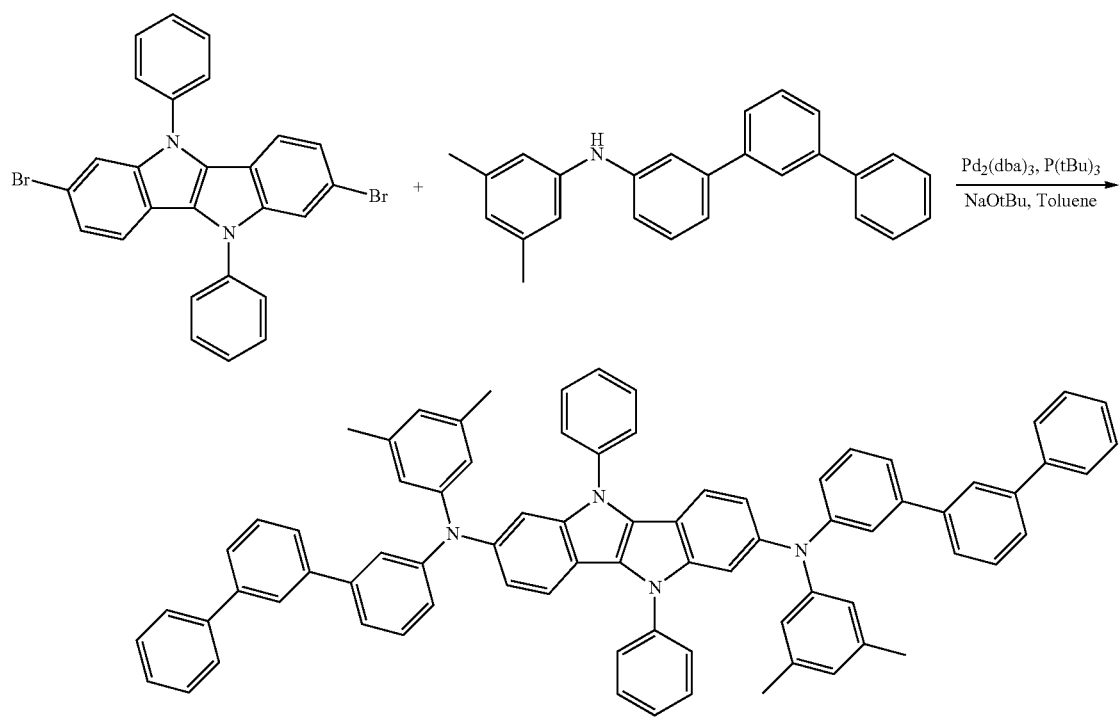

2,7-dibromo-5,10-diphenyl-5,10-dihydroindolo[3,2-b]indole (1.60 g, 3.04 mmol), N-(3,5-dimethylphenyl)-[1,1':3',1"-terphenyl]-3-amine (2.98 g, 6.22 mmol), tris (dibenzylideneacetone) dipalladium (56 mg, 0.06 mmol), tri-tert-butylphosphine (25 mg, 0.12 mmol) and anhydrous toluene (62 ml) were taken in a 200 mL flask under nitrogen and stirred for 5 min. To this solution sodium t-butoxide (0.64 g, 6.68 mmol) was added in small portions with stirring at room temperature and the resulting solution allowed to stir at 90° C. overnight. Reaction was shown complete by UPLC analysis. After cooling the crude product was filtered off, this was dissolved in hot toluene and passed through a layer of silica gel eluted with toluene. Filtrate was reduced in volume whereupon product recrystallized. Crystals were collected and rinsed with toluene (20 mL) and methanol (20 mL). Recrystallized again from toluene under heating gave 576 mg product in 99.1% purity by UPLC analysis. The product structure was confirmed by NMR analysis.

Synthesis Example 7

This example illustrates the synthesis of a compound having Formula I, Compound I-17.

Step 1: 1-chloro-3-[2-(3-chloro-2-nitro-phenyl)ethynyl]-2-nitrobenzene (J)

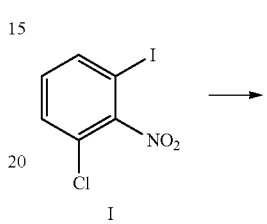

-continued

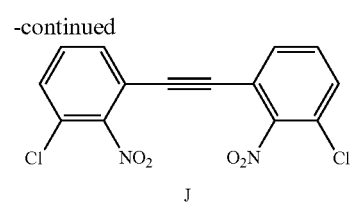

To a stirred solution of 1-chloro-3-iodo-2-nitrobenzene (I; 25 g, 88.2 mmol) in triethylamine (250 mL) was added pyridine (29 mL, 352.8 mmol). The reaction mixture was purged with argon gas for 20 minutes. Tetrakis(triphenylphosphine)palladium(0) (4.00 g, 3.46 mmol), copper (I) iodide (1.34 g, 7.04 mmol) and N, N-dimethylaminopyridine (1.07 g, 8.76 mmol) were added and the reaction mixture was purged with argon gas for another 15 minutes. Acetylene gas was bubbled through the reaction mixture with stirring at room temperature for 7 hours. After removal of volatiles by rotary evaporation, the reaction mixture was diluted with ethyl acetate (500 mL) and filtered. The filtrate was washed with water (500 mL) and brine (500 mL). The organic layer was dried over anhydrous sodium sulfate, filtered and concentrated under reduced pressure. The crude compound was purified by column chromatography using silica gel (60-120 mesh), eluting with 0-10% ethyl acetate in petroleum ether. The product isolated from the chromatography was washed with ethanol (40 mL) to afford the desired product (10.8 g, 73% yield) as brown solid that was determined to be 99.4% pure by UPLC analysis.

Step 2: 1,2-bis(3-chloro-2-nitro-phenyl)ethane-1,2-dione (K)

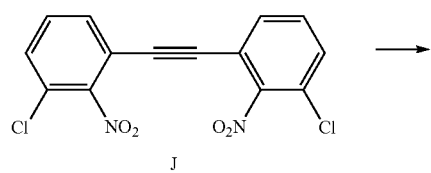

J

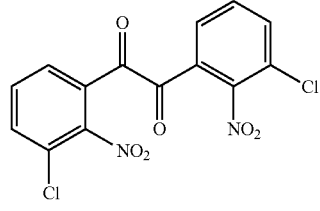

K

To a stirred solution of 1-chloro-3-[2-(3-chloro-2-nitrophenyl)ethynyl]-2-nitrobenzene (12.5 g, 37.21 mmol) in dichloromethane (375 mL) was added a solution of potassium permanganate (23.5 g, 148.7 mmol) in water (375 mL), tetrabutylammonium bromide (1.2 g, 3.72 mmol) and acetic acid (19 mL). The reaction mixture was heated at reflux for 5 hours, cooled to room temperature, poured in to saturated sodium bisulfite solution (400 mL) and stirred with dichloromethane (500 mL) for 30 minutes. The organic layer was separated, washed with water (400 mL), brine (400 mL) and concentrated under reduced pressure. The crude product was washed with ethanol (40 mL) to afford the desired product (8.5 g, 62% yield) as pale yellow solid that was determined to be 91.8% pure by UPLC analysis.

Step 3: 1,6-dichloro-5,10-dihydroindolo[3,2-b]indole (L)

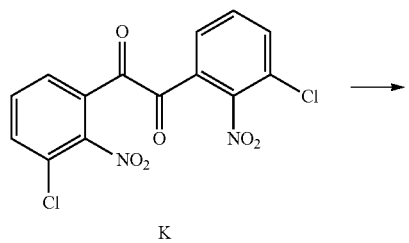

K

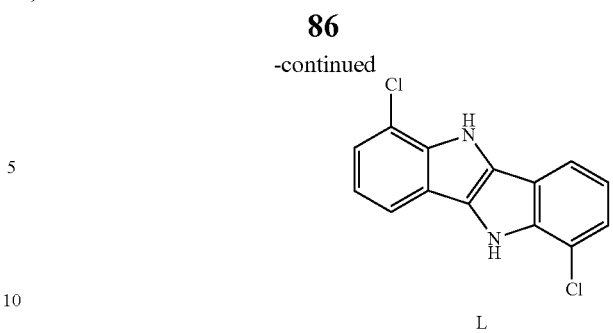

L

A mixture of tin(II) chloride dihydrate (52.1 g, 231 mmol) in acetic acid (300 mL) and aqueous 6N hydrochloric acid (300 mL) was heated to 120° C. for 1 h with stirring. The mixture turned to clear solution. 1,2-bis(3-chloro-2-nitrophenyl)ethane-1,2-dione (10.0 g, 27.18 mmol) was added portion wise over a period of 30 minutes at 120° C. The reaction mixture was heated at reflux for 1 h. The reaction mixture was cooled to room temperature and the resulting precipitate was filtered, washed with water (200 mL) and dried to get crude compound that was washed with ethanol (25 mL) and dried under vacuum to afford the desired product (4.6 g, 62% yield) as a pale yellow solid that was determined to be 98.6% pure by UPLC analysis.

Step 4: 1,6-dichloro-5,10-diphenyl-indolo[3,2-b]indole (M)

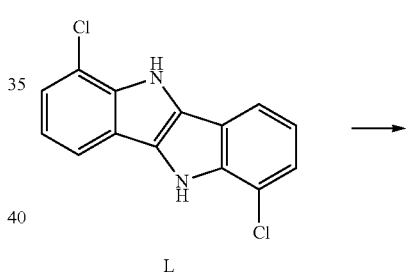

L

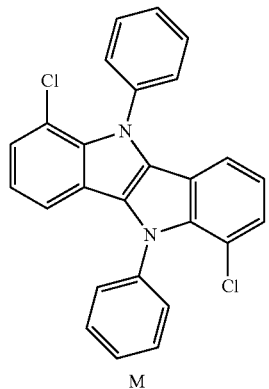

M

To a stirred solution of 1,6-dichloro-5,10-dihydroindolo[3,2-b]indole (100 mg, 0.364 mmol) in 1,2-dichlorobenzene (2 mL) were added bromobenzene (343 mg, 2.19 mmol) and potassium carbonate (302 mg, 2.18 mmol). The reaction mixture was purged with argon gas for 30 minutes, then copper powder (20 mg, 0.298 mmol), and 1,4,7,10,13,16-hexaoxacyclooctadecane (18-crown-6; 36 mg, 0.134 mmol) were added and the reaction mixture was again purged with argon for 15 minutes. The reaction mixture was then heated under reflux for 40 hours, cooled to room temperature, and filtered. The filtrate was diluted with ethyl acetate (10 mL), washed with water (5 mL) and brine (5 mL), dried over anhydrous sodium sulfate and concentrated under reduced pressure. The crude product was purified by washing with 50% ethanol in n-pentane (2 mL) to afford the desired product (0.09 g, 58% yield) as a brown solid that was determined to be 95.0% pure by UPLC analysis. The structure was confirmed by NMR spectrometry and mass spectroscopy.

Step 5

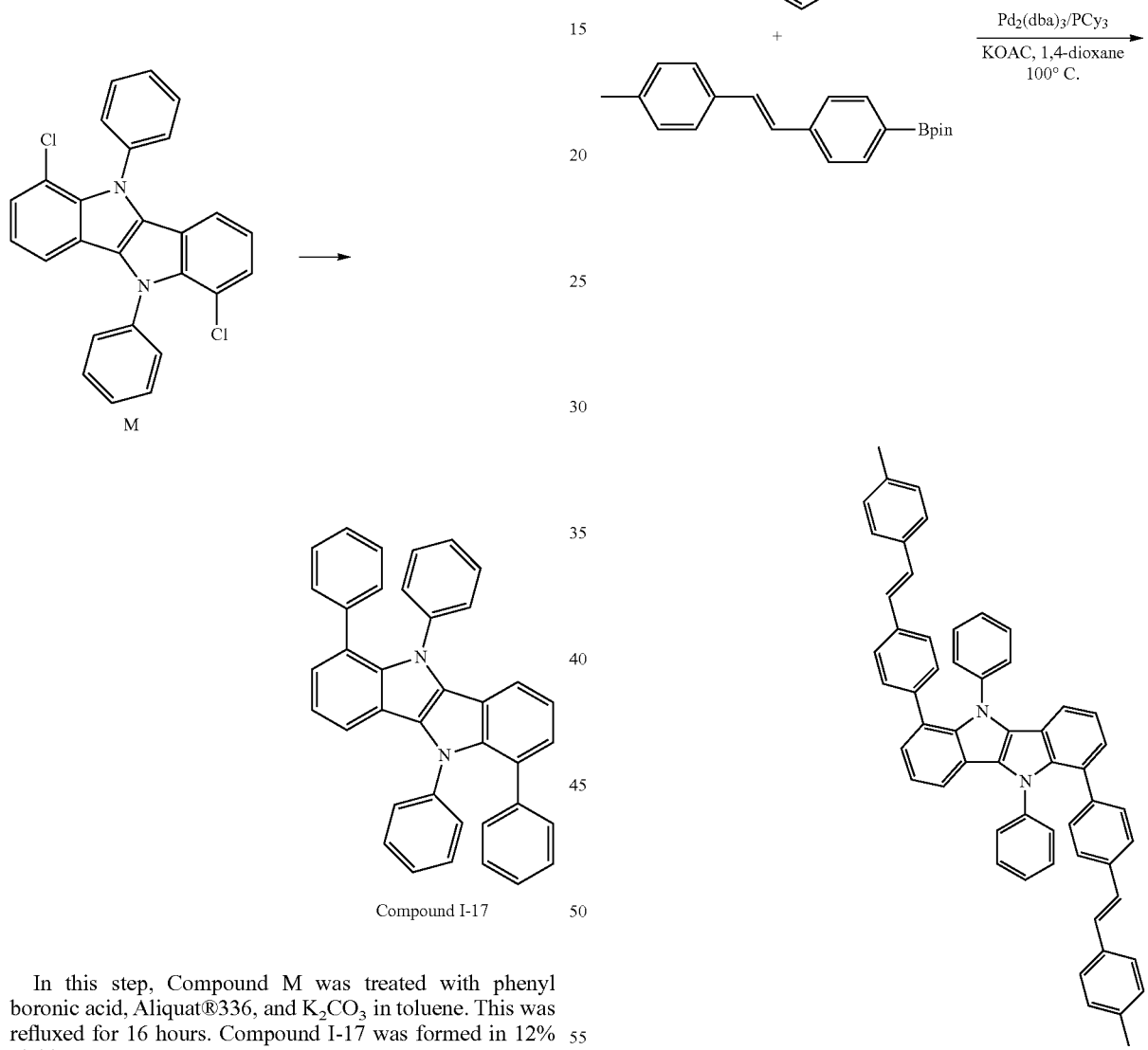

Compound I-17

In this step, Compound M was treated with phenyl boronic acid, Aliquat®336, and K₂CO₃ in toluene. This was refluxed for 16 hours. Compound I-17 was formed in 12% yield.

Synthesis Example 8

This example illustrates how the preparation of a compound having Formula I, Compound I-28, could be carried out.

The compound will be made starting with Compound M from Synthesis Example 7, and treating with the pinacol ester of the appropriate boronic acid, as shown in the scheme below.

I-28

In the above scheme, "Bpin" indicates the pinacol ester of the boronic acid; "dba" is dibenzylideneacetone; "Cy" is cyclohexyl; and "KOAc" is potassium acetate.

Synthesis Example 9

This example illustrates the preparation of a compound having Formula I, bis-(2-napthyl)-indoloindole, I-26.

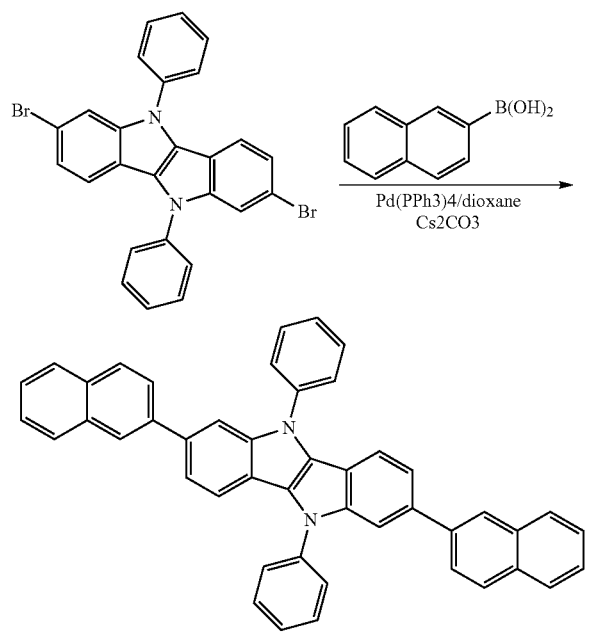

A mixture of 2,7-dibromo-5,10-diphenyl-5,10-dihydro-indolo[3,2-b]indole (0.3 g, 0.58 mmole), 2-naphthylboronic acid (0.25 g, 1.45 mmole), cesium carbonate (1.51 g, 4.64 mmole), and Pd(PPh$_3$)$_4$ (13 mg, 0.012 mmole) in 1,4-dioxane was heated at 100 C for 22 hours under nitrogen atmosphere. After that reaction mixture cooled down, solids filtered and washed with water and dried. Resulting solids were dissolved in dichloromethane (350 ml) and passed through a plug of silica gel washing with dichloromethane. Solvent was evaporated to volume 100 ml and precipitated product collected by filtration to give 0.151 g of 2,7-bis-(2-naphthyl)-5,10-diphenyl-5,10H-indolo[3,2-b]indole with purity 99.8% by UPLC. MS: MH+=612. UV-VIS: $\lambda_{max}$=387 nm in toluene. Photoluminescence (toluene): $\lambda_{max}$: 437 nm.

Synthesis Example 10

This example illustrates the preparation of a compound having Formula VIII, Compound VIII-2.
Step a.

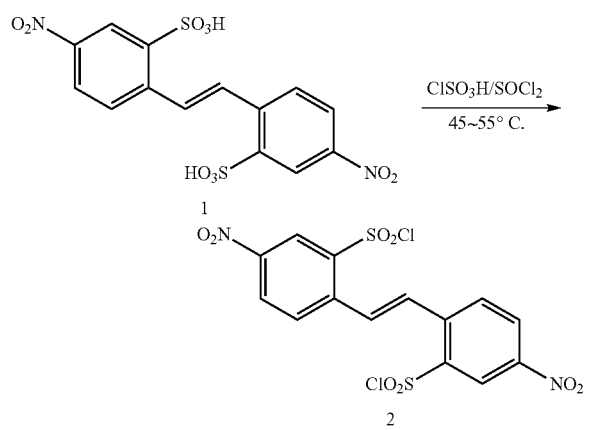

260 g of 4,4'-dinitro-2,2'-stilbenedisulfonic acid was added in portionwise to 1408 g of ClSO$_3$H at <20° C. After stirring for 1 h at 45~55° C., Thionyl chloride (352.7 ml) was added dropwise. The resulting mixture was stirred for 12 hrs at 45~55° C. Quenched to 15 kg crush ice. Filtered and washed with H2O and ethanol. Slurry with refluxing THF and dried. Resulted in yellow solid (188 g, yield: 66.6%).
Step b.

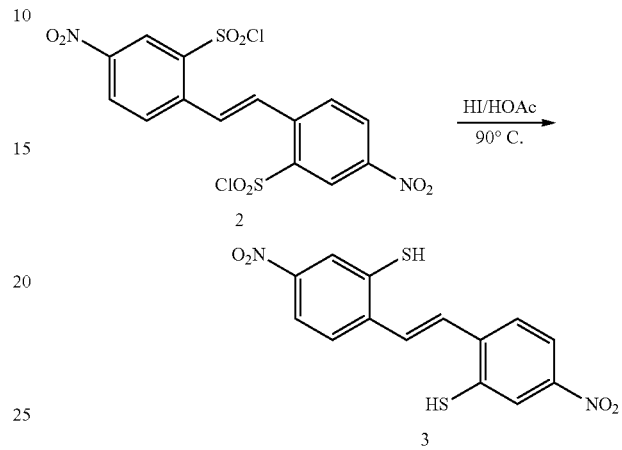

1535 ml of 45% hydroiodic acid were added into the suspension of 84 g of 4,4'-dinitrostilben-2,2'-disulfochloride in 2000 nl of acetic acid at 80-100° C. The resulting reaction mixture was kept at this temperature for extra 9 hours and was allowed to stand at 20° C. for 12 hours. Then the precipitated from the reaction was filtered, and treated with water solution of sodium hydrosulfite, washed and dried (no amounts are indicated for water or sodium hydrosulfite). The yield of 4,4'-dinitrostilben-2,2'-dithiol was 51 g (85%).
Step c.

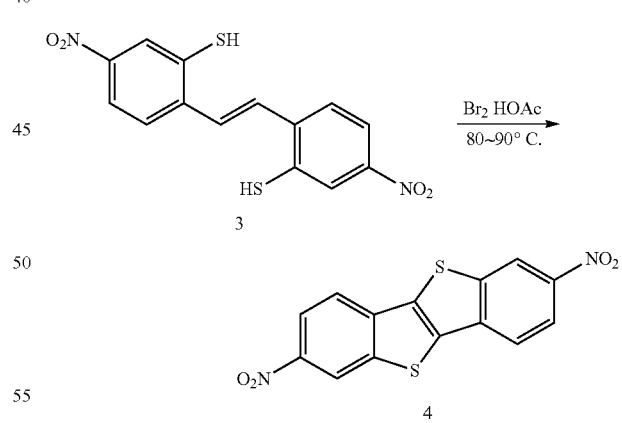

364 g of Bromine was added into the suspension of 4,4'-dinitrostilben-2,2'-dithiol (114 g) in 2250 ml of acetic acid at 80-100° C. The resulting reaction mixture was kept at this temperature for extra 48 hours. Then the precipitated from the reaction was filtered, and treated with water solution of sodium hydrosulfite, washed with acetone and 5% NaHCO$_3$, slurried with THF and dried (no amounts are indicated for water or sodium hydrosulfite). Afford 98 g of product.

Step d.

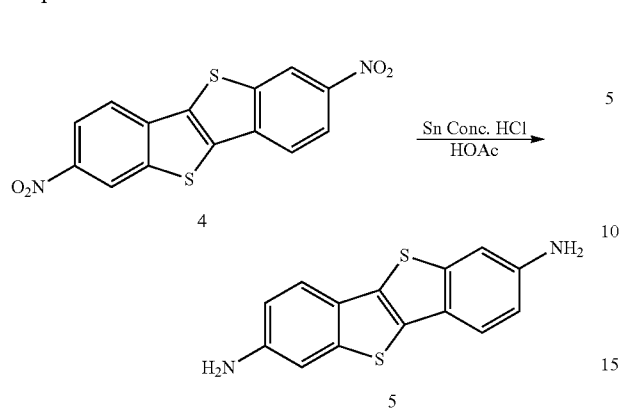

1500 ml of Conc. HCl was added dropwise into the suspension of 4,4'-dinitrobenzothieno(3,2-b)benzothiophene (98 g) and Tin (285 g) in 1750 ml of acetic acid at 80-100° C. The resulting reaction mixture was kept at this temperature for extra 12 hours. After adding 1000 ml 6N HCl, the precipitated from the reaction was filtered, and treated with water and 10% K$_2$CO$_3$. Extracted with refluxing THF twice. recrystallized in THF to get 43 g of 2,7-diaminobenzothieno(3,2-b)benzothiophene (yield: 53%).

Step e.

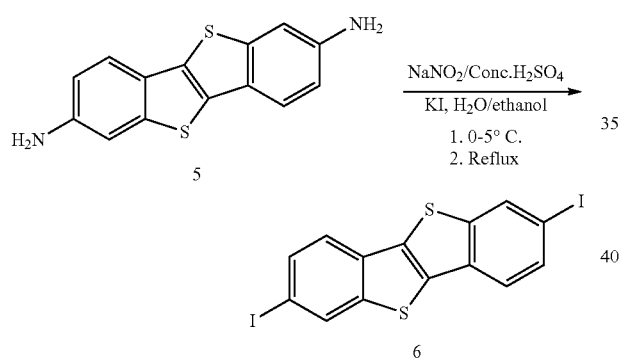

To an ice-cold mixture of 2,7-diaminobenzothieno(3,2-b)benzothiophene (1 g), ethanol (30 ml) and sulfuric acid (4 ml) was added sodium nitrate solution (1.3 g of in 10 ml H$_2$O) below 5° C. After the mixture was stirred for 3 hours, Aqueous potassium Iodide (6.2 g) in 40 ml H$_2$O was added at 0-25° C., stirred for 6 hrs at 25° C., the resulting mixture was refluxed for 5 hrs.

Sodium hydrogen sulfite was added to reduce liberated iodine. The resulting precipitate was collected by filtration, washed with methanol and refluxing THF. The yield was 1.3 g (71%)

Step e.

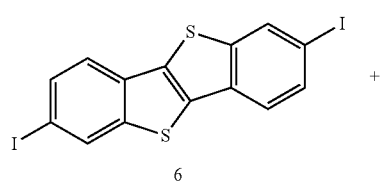 +

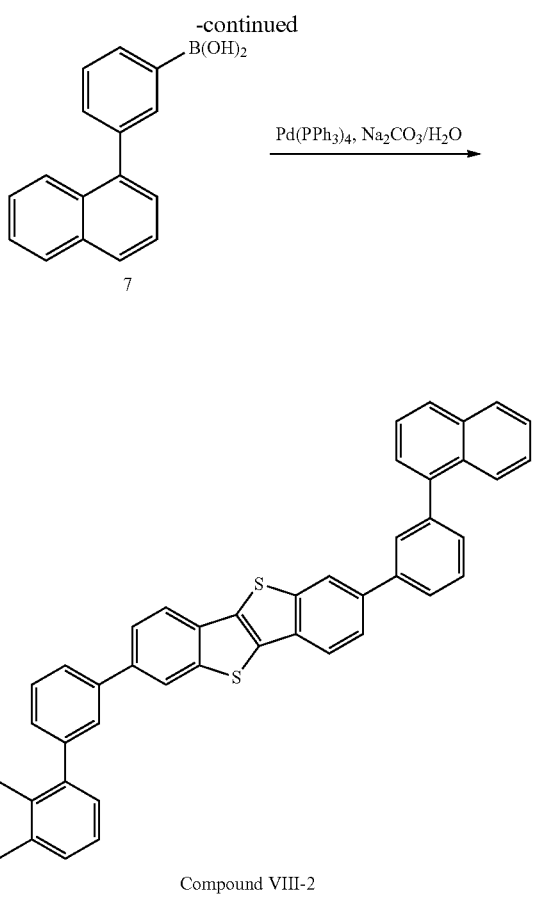

Compound VIII-2

To a mixture of intermediate 6 (1.0 g, 2.03 mmol) and boronic acid 7 (2.02 g, 8.13 mmol) in toluene (~30 mL) was added 2M Na$_2$CO$_3$ (1.1 g, 10 mmol, 5 mL of H$_2$O) followed by the addition of phase-transfer agent Aliquat336 (0.41 g, 1.0 mmol). The mixture was bubbled with nitrogen for 15 min. Then Pd(PPh$_3$)$_4$ (47 mg, 0.04 mmol) was added. The mixture was heated at 90° C. (oil bath) for 3 days under a nitrogen atmosphere. After cooling down the mixture was poured into MeOH. The solid was filtered off and washed with diluted HCl, H$_2$O, MeOH to give a crude: 0.82 g, brown solid. The crude was re-dissolved in CHCl$_3$ (not completely dissolved), passed through a Florisil column, rinsed with Hex/CHCl$_3$ 5:1, 4:1, 3:1, 2:1, 1:1 to CHCl$_3$. The pure fractions were collected and concentrated, hexane was added. The solid was filtered and rinsed with hexane to give Compound VIII-2, 0.42 g, 32%, as a pale yellow solid. The structure was confirmed by NMR.

Synthesis Example 11

This example illustrates the preparation of a compound having Formula I, Compound I-19, and the corresponding polymer having Formula II, Compound II-1.

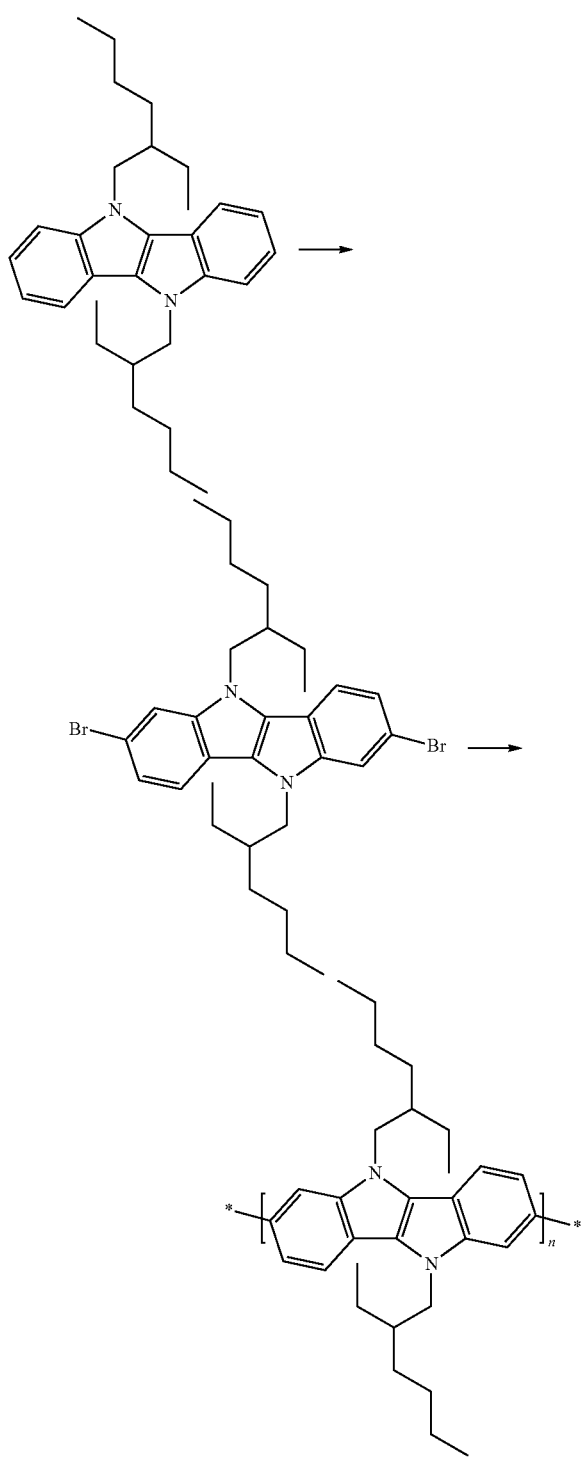

a. Synthesis of 5,10-bis(2-ethylhexyl)-5,10-dihydroindolo[3,2-b]indole, Compound I-19

Sodium hydride (60% dispersion in mineral oil, 4 g, 0.1 mole) was stirred in octane under nitrogen for 5 minutes and then sodium hydride allowed to precipitate. Octane decanted and activated sodium hydride was transferred to a suspension of 5,10-dihydro-indolo[3,2-b]indole (7.5 g, 36.4 mmole) in dry DMF (100 ml) followed by addition of 2-ethylhexylbromide (17.6 g, 91 mmole). The mixture was stirred for 10 hours under nitrogen atmosphere at ambient temperature, after that the product was precipitated by adding 100 ml of methanol, product collected by filtration, washed with methanol and dried. Yield 12 g (27.9 mmole, 77%). $^1$H-NMR (CDCl$_3$, 500 MHz): 0.84 (t, J=7 Hz, 6H), 0.90 (t, J=7 Hz, 6H), 1.18-1.51 (m, 16H), 2.12-2.24 (m, 2H) 4.26-4.46 (m, 4H), 7.16 (t, J=7 Hz, 2H), 7.24-7.34 (m, 2H), 7.44 (d, J=8 Hz, 2H), 7.84 (d, J=8 Hz, 2H). MS: 431 (MH+). UV-VIS: $\lambda_{max}$=371, 356, 327, 262, 204 nm in acetonitrile-water 1:1.

b. Synthesis of monomer-2,7-dibromo-5,10-bis-(2-ethylhexyl)-5,10-dihydroindolo[3,2-b]indole To a stirred solution of 5,10-bis-(2-ethylhexyl)-5,10-dihydroindolo[3,2-b]indole (9.0 g, 20.9 mmole) in dichloromethane (100 ml) N-bromosuccinimide (7.81 g, 43.9 mmole, 2.1 equiv.) was added at once and the reaction mixture stirred for 20 minutes at room temperature. After that the reaction mixture was quenched with acetone (10 ml), passed through a plug of silica washing with dichloromethane. Solvent evaporated using rotary evaporator, the residue redissolved in toluene and precipitated by addition of methanol. The product was collected by filtration. Yield 10 g (17 mmole, 81%). $^1$H-NMR (CDCl$_3$, 500 MHz): 0.83 (t, J=7 Hz, 6H), 0.89 (t, J=7 Hz, 6H), 1.15-1.48 (m, 16H) 2.02-2.17 (m, 2H) 4.25 (m, 4H) 7.25-7.27 (m, 2H) 7.55 (d, J=2 Hz, 2H) 7.63 (d, J=8 Hz, 2H). MS: 589 (MH+). UV-VIS: $\lambda_{max}$=381, 365, 339, 276 nm in acetonitrile-water 1:1.

c. Synthesis of poly(5,10-bis(2-ethylhexyl)-5,10-dihydroindolo[3,2-b]indole), Compound II-1

A mixture of bis(1,5-cyclooctadiene)nickel (0.55 g, 2 mmole), 2,2'-dipyridyl (0.312 g, 2 mmole) and 1,5-cyclooctadiene (0.216 g, 2 mmole) in toluene (20 ml) and dimethylformamide (10 ml) was stirred at 60° C. for 45 minutes under nitrogen atmosphere. After that a solution of 2,7-dibromo-5,10-bis(2-ethylhexyl)-5,10-dihydroindolo[3,2-b]indole (0.563 g, 0.96 mmole) and 4-bromobiphenyl (11 mg) in 10 ml of toluene was added at once and the reaction mixture was stirred at 60° C. for 3 hours. After that reaction cooled to room temperature and poured into methanol (200 ml) and conc. hydrochloric acid (15 ml) with rapid stirring. Stirred for 30 min. Crude polymer was filtered and washed with methanol and toluene. Solids dissolved in dichloromethane and filtered through a plug of silica washing with dichloromethane. Solvents evaporated to give the product with bright blue luminescence in toluene solution. Gel permeation chromatography in tetrahydrofuran, Mw=4400. Polydispersity 1.3. UV-VIS: $\lambda_{max}$=435, 367, 296 nm in toluene.

Synthesis Example 12

This example illustrates the preparation of a polymer having Formula II, Compound II-3.

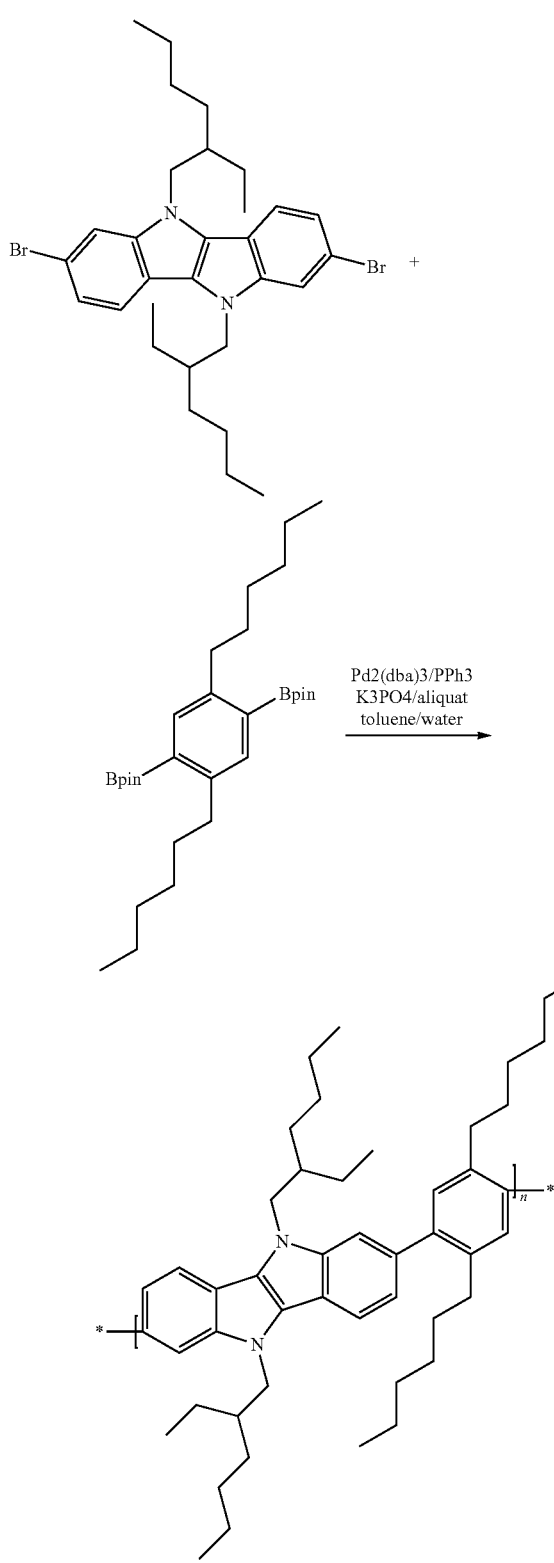

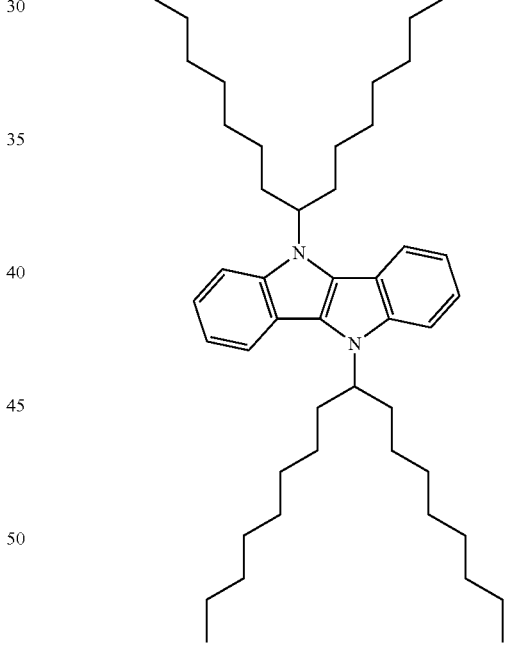

A mixture of 2,7-dibromo-5,10-bis-(2-ethylhexyl)-5,10-dihydroindolo[3,2-b]indole (0.546 g, 0.93 mmole), (4,4,5,5-tetramethyl-1,2,3-dioxaborolane-1,4-diyl)-2,5-dihexylphenylene (0.462 g, 0.93 mmole), Pd$_2$(dba)$_3$ (0.045 g, 0.037 mmole), triphenylphosphine (0.037 g, 0.093 mmole), potassium phosphate (0.591 g, 2.79 mmole), aliquat 336 (0.2 g) in water (2 ml) and toluene (20 ml) was purged with nitrogen for 30 min and then heated to 100 C overnight. Reaction mixture was cooled down, diluted with 100 ml of toluene and organic phase separated. Sodium diethyldithiocarbamate (10 equivalents, 2 g) was added to toluene solution, the resulting mixture stirred for an hour and passed through filter filled with silica gel washing with toluene and dichloromethane. Toluene was evaporated on rotary evaporator to give 225 mg of crude polymer. Additional purification on column filled with basic alumina and silica gel followed by evaporation of solvents, redissolving polymer in 15 ml of toluene and precipitation into methanol afforded 20 mg of Compound II-3. Molecular weight by GPC—13.2 KDa. UV-vis (toluene), $\lambda_{max}$: 348 nm. Photoluminescence (toluene): $\lambda_{max}$: 424 nm.

Synthesis Example 13

This example illustrates the preparation of a compound having Formula I, Compound I-20, and the corresponding polymer, a. Synthesis of 5,10-bis-(9-heptadecyl)-5,10-dihydroindolo[3,2-b]indole, Compound I-20

Sodium hydride (60% dispersion in mineral oil, 0.57 g, 14 mmole) was stirred in octane under nitrogen and then allowed to precipitate. Octane decanted and activated sodium hydride was transferred to a suspension of 5,10-dihydro-indolo[3,2-b]indole (0.89 g, 4.3 mmole) in dry DMF (18 ml) and 52% purity 9-heptadecyl tosylate (10 g). The mixture was stirred overnight under nitrogen atmosphere. After that the mixture was diluted with methanol (20 ml), solvent decanted and the residue subjected to short column filled with silica gel washing with toluene. Solvent was distilled off using rotary evaporator and the residue was subjected to the second column filled with silica gel using hexanes as eluent. Solvent was distilled off using rotary evaporator to give 2.7 g of the product as white solids. UV-VIS: $\lambda_{max}$=374 nm in toluene. Photoluminescence (toluene): $\lambda_{max}$: 404 nm.

b. Synthesis of Polymer, Compound II-5

A mixture of bis-(1,5-cyclooctadiene)nickel (0.396 g, 1.44 mmole), 2,2'-dipyridyl (0.225 g, 1.44 mmole) and 1,5-cyclooctadiene (0.156 g, 1.44 mmole) in toluene (15 ml) and dimethylformamide (15 ml) was stirred at 60° C. for 45 minutes under nitrogen atmosphere. After that a solution of 2,7-dibromo-5,10-bis-(9-heptadecyl)-5,10-dihydroindolo[3,2-b]indole (0.600 g, 0.713 mmole) in 15 ml of toluene was added at once and the reaction mixture was stirred at 60° C. for 3 hours. After that reaction cooled to room temperature and poured into methanol (300 ml) and conc. hydrochloric acid (15 ml) with rapid stirring and stirred for 1 hour. Precipitate filtered, dissolved in toluene and passed through a column filled with layers of silica gel and basic alumina washing with toluene. Solvent evaporated on rotary evaporator, the residue redissolved in toluene and precipitated by addition of acetone. Solvent decanted, solids were redissolved in toluene and precipitated into methanol. Yield—270 mg (56%). Gel permeation chromatography in tetrahydrofuran, Mw=482 KDa. Polydispersity 3.04. UV-VIS: $\lambda_{max}$=442 nm in toluene. Photoluminescence (toluene): $\lambda_{max}$: 471 nm.

Synthesis Example 14

This example illustrates the preparation of a polymer having Formula II, Compound II-6.

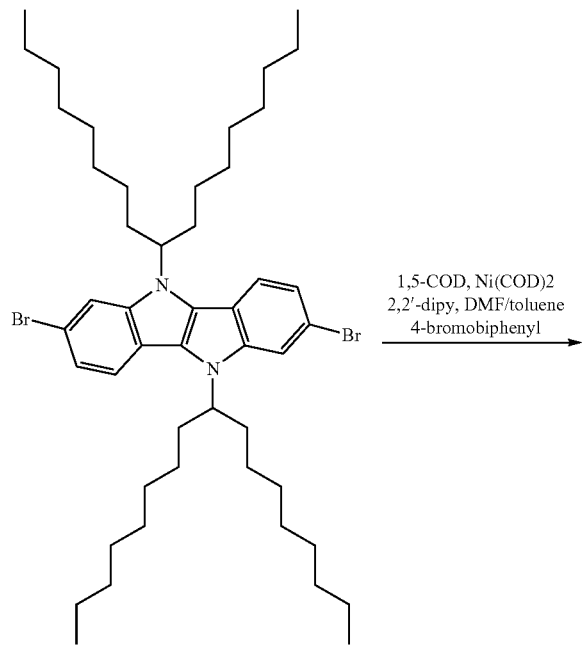

A mixture of bis-(1,5-cyclooctadiene)nickel (0.231 g, 0.84 mmole), 2,2'-dipyridyl (0.131 g, 0.84 mmole) and 1,5-cyclooctadiene (0.091 g, 0.84 mmole) in toluene (8 ml) and dimethylformamide (5 ml) was stirred at 60° C. for 45 minutes under nitrogen atmosphere. After that a solution of 2,7-dibromo-5,10-bis-(9-heptadecyl)-5,10-dihydroindolo[3,2-b]indole (0.35 g, 0.416 mmole) and 4-bromobiphenyl (9.5 mg, 0.041 mmole) in 8 ml of toluene was added at once and the reaction mixture was stirred at 60° C. for 3 hours. After that reaction cooled to room temperature and poured into methanol (300 ml) and conc. hydrochloric acid (15 ml) with rapid stirring and stirred for 1 hour. Precipitate filtered, dissolved in toluene and passed through a column filled with layers of silica gel and basic alumina washing with toluene. Solvent evaporated on rotary evaporator till volume 20 ml and 20 ml of acetone added to the solution to precipitate the product. Solids were collected by filtration, redissolved in toluene and precipitated into methanol to give 140 mg of Compound II-6. Gel permeation chromatography in tetrahydrofuran, Mw=73 KDa. Polydispersity 2.12. UV-VIS: $\lambda_{max}$=443 nm in toluene. Photoluminescence (toluene): $\lambda_{max}$: 472 nm.

Synthesis Example 15

This example illustrates the preparation of a polymer having Formula II, Compound II-7.

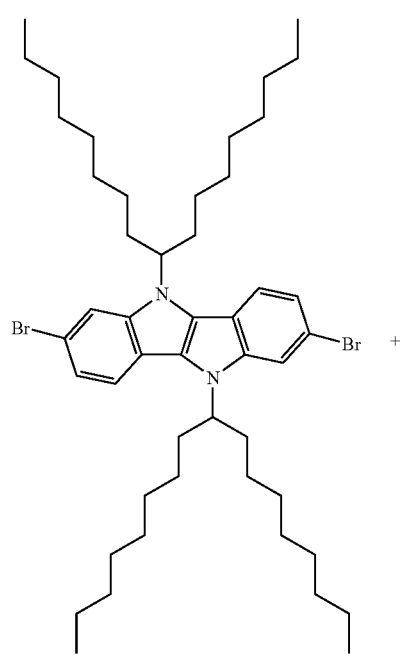

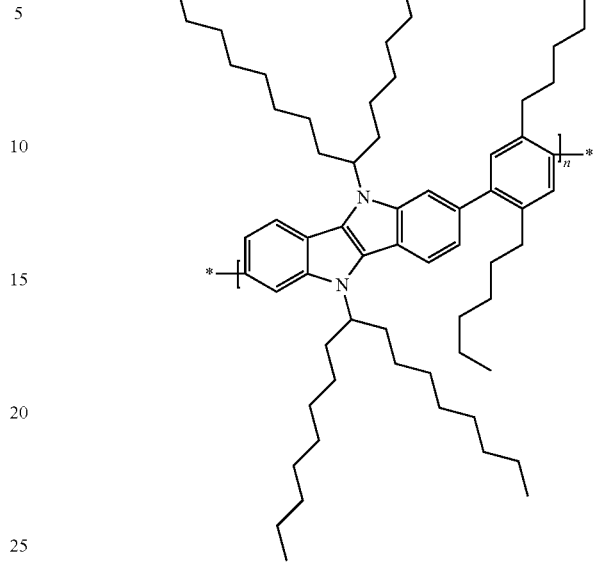

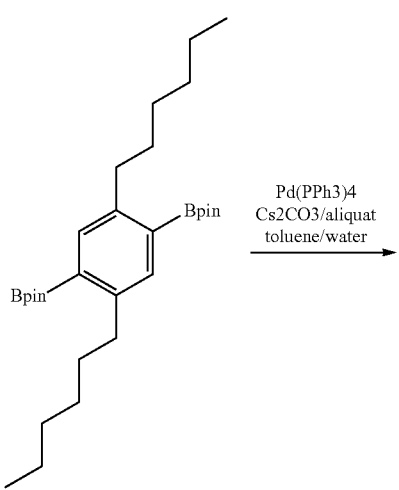

A mixture of 2,7-dibromo-5,10-bis-(9-heptadecyl)-5,10-dihydroindolo[3,2-b]indole (0.45 g, 0.535 mmole), (4,4,5,5-tetramethyl-1,2,3-dioxaborolane-1,4-diyl)-2,5-dihexyl-phenylene (0.267 g, 0.535 mmole), Pd(PPh$_3$)$_4$ (0.031 g, 0.0268 mmole), cesium carbonate (0.538 g, 1.605 mmole), aliquat 336 (0.2 g) in water (2 ml) and toluene (20 ml) was purged with nitrogen for 30 min and then heated to 100 C for 10 hours. After that the reaction mixture was cooled to room temperature, diluted with toluene (100 ml), washed with water. Organic phase separated and passed through filter filled with silica gel washing with toluene. The residue after evaporation of toluene was subjected to an additional column purification using basic alumina and silica gel washing with toluene. Toluene distilled off and dried in vacuum to give 370 mg of amorphous Compound II-7. Gel permeation chromatography in tetrahydrofuran, Mw=16 KDa. UV-VIS: $\lambda_{max}$=348 nm in toluene. Photoluminescence (toluene): $\lambda_{max}$: 421 nm.

Synthesis Example 16

This example illustrates the preparation of a copolymer having Formula VI, Compound VI-2.

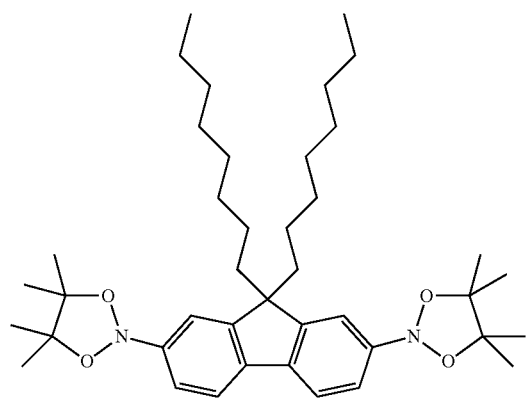 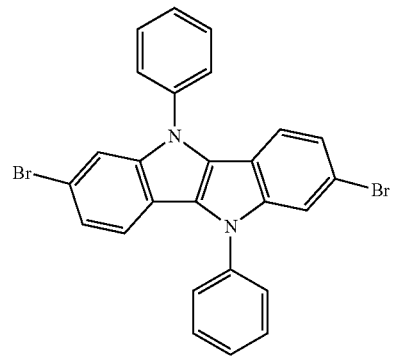

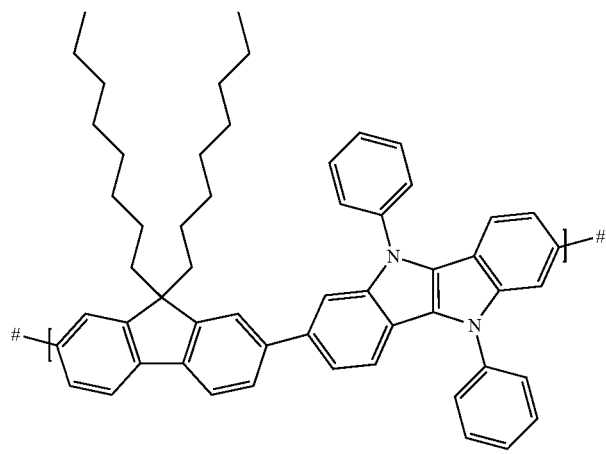

A mixture of 2,7-dibromo-5,10-diphenyl-5,10-dihydroindolo[3,2-b]indole (0.5 g, 0.969 mmole), 2,7-bis(4,4,5,5-tetramethyl-1,3,2-dioxaborolan-2-yl)-9,9-di-n-octylfluorene (0.623 g, 0.969 mmole), cesium carbonate (0.944 g, 2.907 mmole), aliquat 336 (0.2 g) in water (5 ml) and toluene (50 ml) was purged with nitrogen for 5 min then solution of Pd(PPh$_3$)$_4$ (6 mg, 0.0048 mmole) in toluene (5 ml) was added and the mixture was purged with nitrogen for additional 30 min and then heated at 100 C for 6 hours. After that reaction mixture was cooled down to room temperature and additional amount of Pd(PPh$_3$)$_4$ (6 mg, 0.0048 mmole) in toluene (5 ml) added, reaction mixture purged with nitrogen and heated for an additional 8 hours at 100 C. Reaction mixture cooled down to room temperature, diluted with 100 ml of toluene, organic phase separated and passed through filter filled with silica gel washing with toluene and dichloromethane. The residue after evaporation of solvents was subjected to purification on column filled with basic alumina and silica gel washing with toluene. Crude product after distillation of eluent was fractionated by dissolving in toluene (20 ml) and addition of acetone (20 ml). Higher molecular weight polymeric fraction was collected by decanting solution, redissolving solids in toluene (20 ml) and precipitation into methanol (200 ml) to give 80 mg of polymeric fraction having higher molecular weight. Gel permeation chromatography in tetrahydrofuran, Mw=67 KDa. Polydispersity=2. UV-VIS: $\lambda_{max}$=421 nm in toluene. Photoluminescence (toluene): $\lambda_{max}$: 453 nm.

Supernatant was collected, solvent evaporated, the residue redissolved in toluene and precipitated into methanol to give 50 mg of lower molecular weight fraction. Gel permeation chromatography in tetrahydrofuran, Mw=18 KDa. Polydispersity=1,9. UV-VIS: $\lambda_{max}$=420 nm in toluene. Photoluminescence (toluene): $\lambda_{max}$: 452 nm.

Synthesis Example 17

This example illustrates the preparation of a compound having Formula I, Compound I-21.

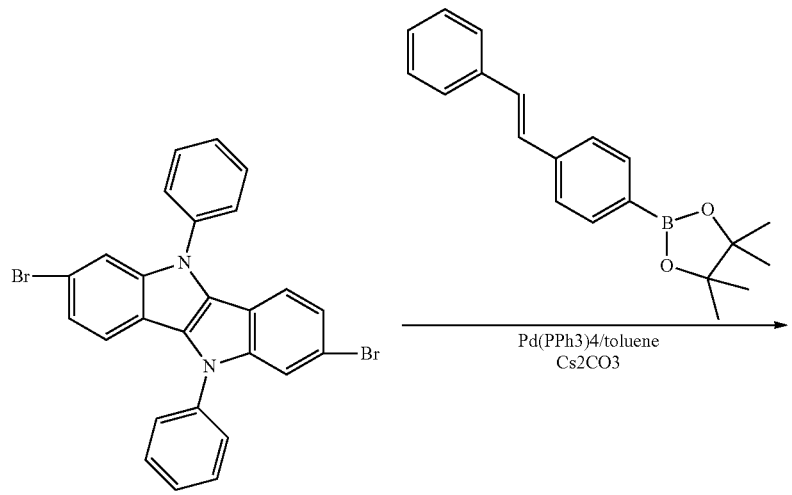

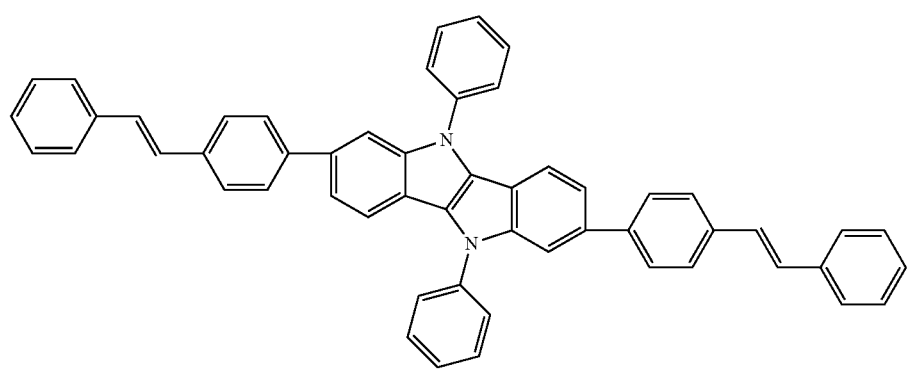

A mixture of 2,7-dibromo-5,10-diphenyl-5,10-dihydro-indolo[3,2-b]indole (3.15 g, 6.1 mmole), 4,4,5,5-tetramethyl-2-[4-[(1E)-2-phenylethenyl]phenyl]-1,3,2-dioxaborolane (4.1 g, 13.4 mmole), cesium carbonate (15.6 g, 48 mmole), and Pd(PPh$_3$)$_4$ (0.69 g, 0.60 mmole) in 1,4-dioxane (160 ml) was heated at 94 C for 18 hours under nitrogen atmosphere. After that reaction mixture was cooled down, solids were filtered, washed with water and dried to give crude product. This crude material was suspended in hot nitrobenzene, solids filtered and washed with acetone and dried to give 1.67 g of crude material. This material was sublimed in high vacuum to give 1.06 g of Compound I-21 with purity 97% by UPLC. Product is not sufficiently soluble for NMR analysis.

Compound I-11 can be made in an analogous way using

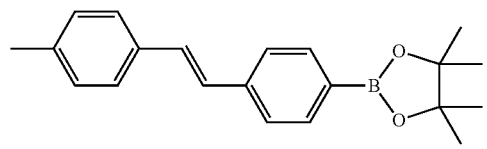

Synthesis Example 18

This example illustrates the preparation of a compound having Formula I, Compound I-12.

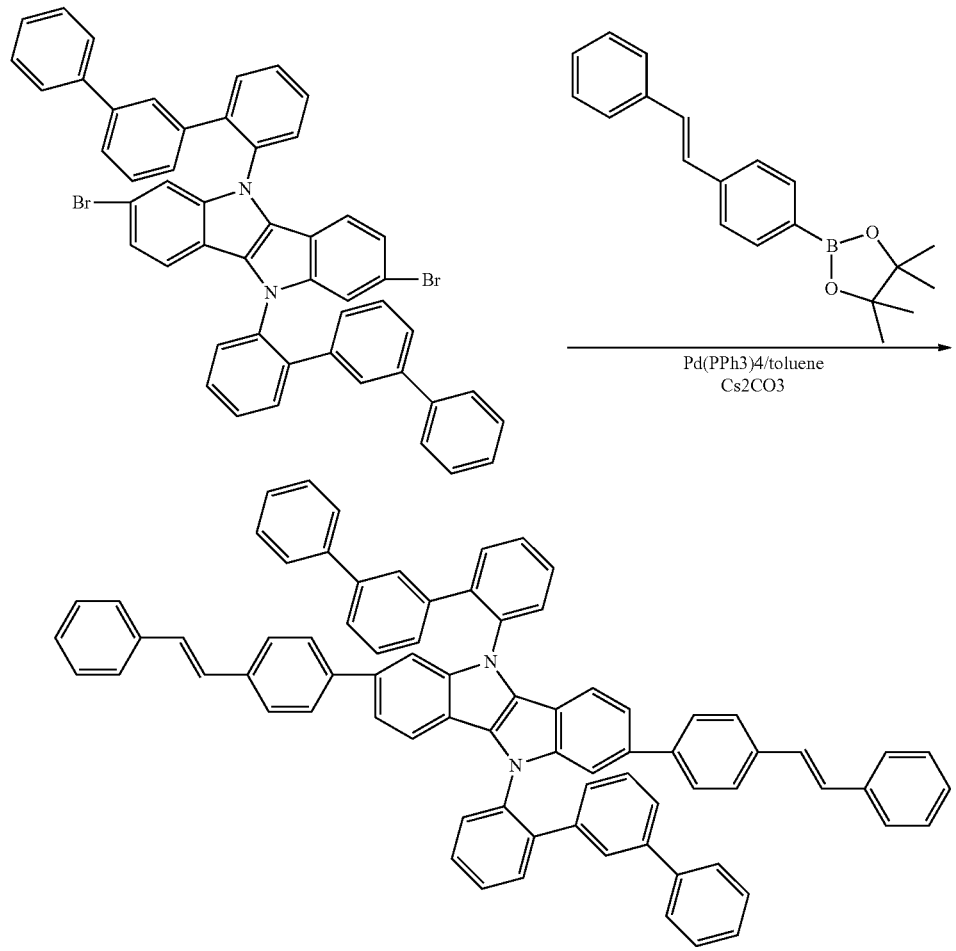

A mixture of 2,7-dibromo-5,10-bis-(ortho-terphenyl-yl)-5,10-dihydro-indolo[3,2-b]indole (0.458 g, 0.691 mmole), 4,4,5,5-tetramethyl-2-[4-[(1E)-2-phenylethenyl]phenyl]-1,3,2-dioxaborolane (0.779 g, 2.072 mmole), cesium carbonate (1.117 g, 3.455 mmole), and Pd(PPh$_3$)$_4$ (46 mg, 0.023 mmole) in 1,4-dioxane (100 ml) was heated at 100 C for 1 day under nitrogen atmosphere. After that reaction mixture was cooled down, solids were filtered, washed with water and methanol to give crude product. This crude material was dissolved in a mixture of hot chlorobenzene and 1,2-dichlorobenzene under nitrogen atmosphere, filtration of hot solution through 0.2 micron filter and collecting precipitate formed upon cooling to ambient temperature. Yield—50 mg. UV-VIS: $\lambda_{max}$=406 nm in toluene. Photoluminescence (toluene): $\lambda_{max}$: 495 nm.

Synthesis Example 19

This example illustrates the preparation of a compound having Formula I, bis-dibenzofuranyl indoloindole, Compound I-22.

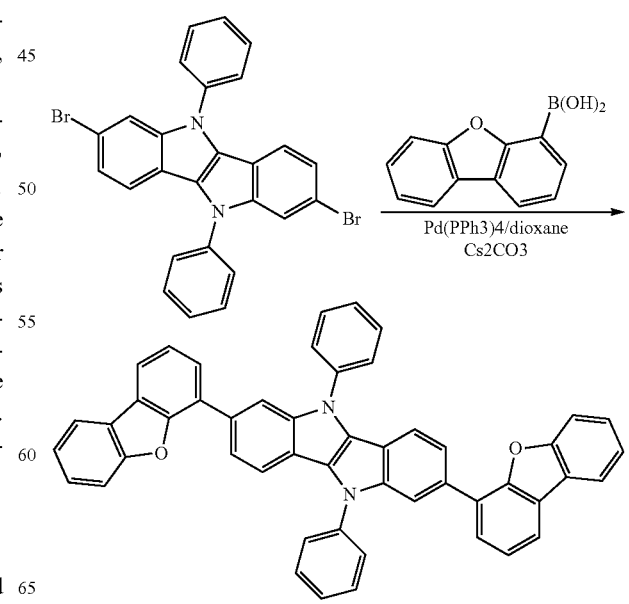

A mixture of 2,7-dibromo-5,10-diphenyl-5,10-dihydro-indolo[3,2-b]indole (1 g, 1.937 mmole), 4-(dibenzofuranyl) boronic acid (1.23 g, 5.811 mmole), cesium carbonate (3.16 g, 9.69 mmole), and Pd(PPh$_3$)$_4$ (132 mg, 0.11 mmole) in 1,4-dioxane (100 ml) was heated at 100 C overnight under nitrogen atmosphere. After that reaction mixture cooled down, solids filtered and washed with water and methanol. The resulting solid material was placed into 250 ml flask and dissolved in 1,2-dichlorobenzene heated to 180 C. Crystalline product formed upon cooling the resulting solution to ambient temperature was collected by filtration, washed with dichloromethane and dried in vacuum to give 420 mg of the product with purity >99.9% by UPLC. Product is not sufficiently soluble for NMR. UV-VIS: $\lambda_{max}$=388 nm in toluene. Photoluminescence (toluene): $\lambda_{max}$: 436 nm.

Synthesis Example 20

This example illustrates the preparation of a compound having Formula I, bis-benzocarbazolyl indoloindole, Compound I-23.

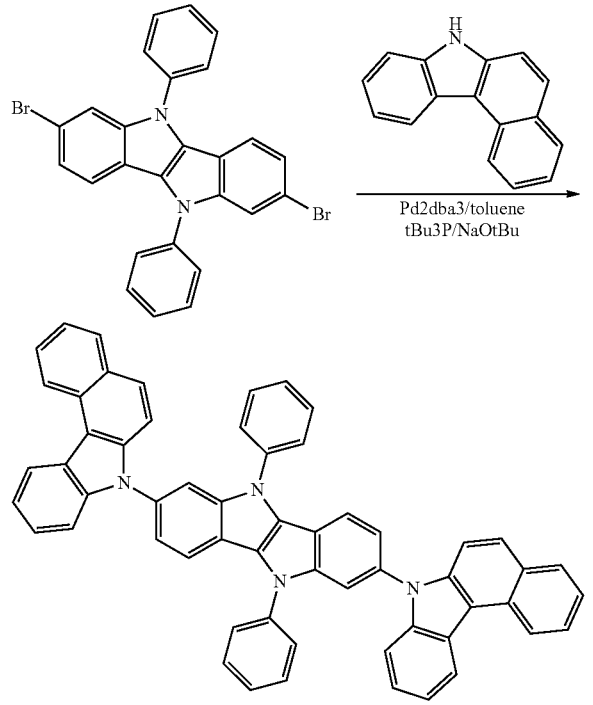

A mixture of 2,7-dibromo-5,10-diphenyl-5,10-dihydro-indolo[3,2-b]indole (0.95 g, 1.84 mmole), 7H-benzo[c]carbazole (1 g, 4.6 mmole), Pd$_2$(dba)$_3$ (0.084 g, 0.092 mmole), and tri-tert-butyl phosphine (0.037 g, 0.184 mmole) in toluene (150 ml) was stirred under nitrogen atmosphere for approximately 1 min followed by addition of sodium tert-butoxide (0.6 g, 6.25 mmol). Reaction mixture was heated at 100 C overnight. After that additional amount of Pd$_2$(dba)$_3$ (0.084 g, 0.092 mmole), tri-tert-butyl phosphine (0.037 g, 0.184 mmole) and sodium tert-butoxide (0.6 g, 6.25 mmol) added and the mixture was heated at 100 C for 1 day. Mixture was cooled down to ambient temperature, precipitate filtered, washed with water and methanol. This crude product was dissolved in minimal amount of dichloromethane (400 ml) and passed through a filter filled with silica gel and basic alumina washing with dichloromethane. The residue after evaporation of dichloromethane was recrystallized from a mixture of hot chlorobenzene and 1,2-dichlorobenzene under nitrogen atmosphere to give 370 mg of the product after filtration and drying in vacuum. $^1$H-NMR (CDCl$_3$, 500 MHz): 7.24-8.05 (broadened signals due to aggregation, 32H), 8.66 (d, 2H, J=9.5 Hz), 8.86 (d, 2H, J=8.5 Hz). UV-VIS: $\lambda_{max}$=366 nm in toluene. Photoluminescence (toluene): $\lambda_{max}$: 391 nm.

Synthesis Example 21

This example illustrates the preparation of a compound having Formula I, bis-(10H-phenoxazin-10-yl)-indoloindole, Compound I-24.

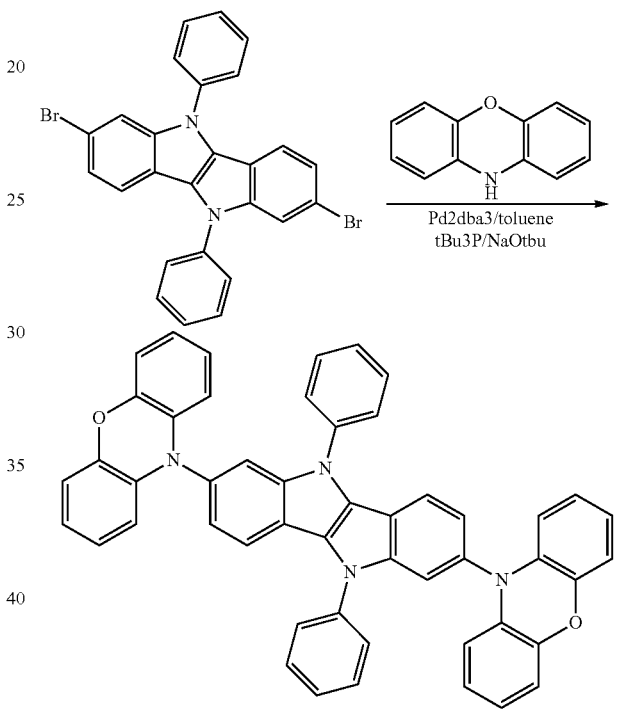

A mixture of 2,7-dibromo-5,10-diphenyl-5,10-dihydro-indolo[3,2-b]indole (1 g, 1.94 mmole), phenoxazine (0.87 g, 4.84 mmole), Pd$_2$(dba)$_3$ (0.089 g, 0.097 mmole), and tri-tert-butyl phosphine (0.039 g, 0.194 mmole) in toluene (150 ml) was stirred under nitrogen atmosphere for approximately 1 min followed by addition of sodium tert-butoxide (0.558 g, 5.82 mmol). Reaction mixture was heated at 100 C overnight. Mixture was cooled down to ambient temperature, precipitate filtered, washed with water and methanol. Crude product was not sufficiently soluble for column chromatography purification. Solids were gradually dissolved within 1 hour in 1,2-dichlorobenzene (200 ml) at 180 C under nitrogen atmosphere. Product precipitated upon cooling of 1,2-dichloromethane solution to ambient temperature (0.8 g after drying in vacuum). Crystallization was repeated one time more using equal amount of 1,2-dichlorobenzene (200 ml). Product collected by filtration and dried in vacuum to yield 0.6 g (purity by UPLC 99.63%) of the desired material. Product is not sufficiently soluble for NMR. UV-VIS: $\lambda_{max}$=356, 324 nm in toluene. Photoluminescence (toluene): $\lambda_{max}$: 433 nm.

Synthesis Example 22

This example illustrates the preparation of a compound having Formula I, bis-(9,9-dimethylfluorenyl)-indoloindole, Compound I-25.

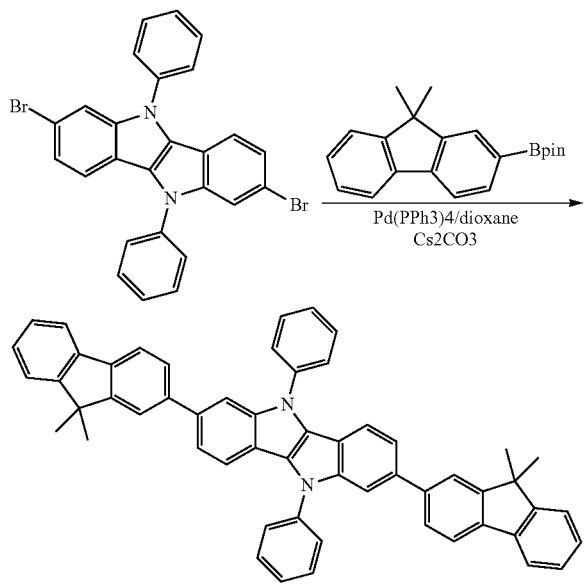

A mixture of 2,7-dibromo-5,10-diphenyl-5,10-dihydro-indolo[3,2-b]indole (1 g, 1.94 mmole), 9,9-dimethylfluorene-2-pinacolboronate (1.56 g, 4.87 mmole), cesium carbonate (5.1 g, 15.7 mmole), and Pd(PPh$_3$)$_4$ (45 mg, 0.039 mmole) in 1,4-dioxane (50 ml) was heated at 100 C for 20 hours under nitrogen atmosphere. After that reaction mixture cooled down, solids filtered and washed with water and dried. Resulting solids were dissolved in dichloromethane (900 ml) and passed through a plug of silica gel washing with dichloromethane. Solvent was evaporated to volume 250 ml and precipitated product collected by filtration to give 0.95 g of crude material that was additionally recrystallized from hot toluene (300 ml) to give 0.68 g of Compound I-25 with purity 99.82% by UPLC. MS: MH+=743. UV-VIS: $\lambda_{max}$=391 nm in toluene. Photoluminescence (toluene): $\lambda_{max}$: 438 nm.

Synthesis Example 23

This example illustrates the preparation of a compound having Formula I, 2-(N-benzocarbazolyl)-7-(N-phenyl-N-1-napthyl)-indoloindole, Compound I-27.

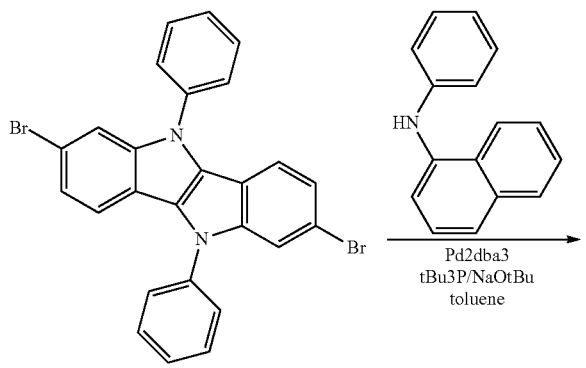

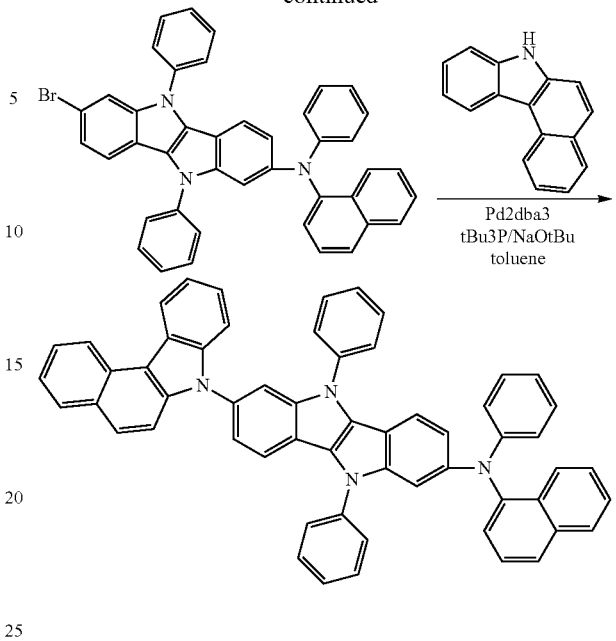

a. Synthesis of 2-bromo-7-(N-phenyl-N-1-napthyl)-5,10-diphenyl-indolo[3,2-b]indole A mixture of 2,7-dibromo-5,10-diphenyl-5,10-dihydro-indolo[3,2-b]indole (1.3 g, 2.519 mmole), N-phenyl-N-1-napthylamine (0.69 g, 3.15 mmole), Pd$_2$(dba)$_3$ (0.056 g, 0.061 mmole), and 1,1'-bis(diphenylphosphino)ferrocene (0.062 g, 0.011 mmole) in toluene (100 ml) was stirred under nitrogen atmosphere for approximately 1 min followed by addition of sodium tert-butoxide (0.362 g, 3.78 mmol). Reaction mixture was heated at 100 C overnight. After that reaction mixture cooled down, water (100 ml) added and the reaction mixture was stirred in the air for 30 min. Toluene layer separated and passed through a layer of celite, florisil and silica gel washing with toluene (300 mL). Solvent was removed by using rotary evaporator, the residue was redissolved in dichloromethane and evaporated onto celite and purified on silica gel column using hexanes-dichloromethane mixtures as eluent. All fractions containing product combined, eluent evaporated by using rotary evaporator. The residue after evaporation of eluent—430 mg (purity 90% by UPLC) was used for the next step without further purification. MS: MH+=656. UV-VIS: $\lambda_{max}$=393 nm in water-acetonitrile.

b. Synthesis of 2-(N-benzocarbazolyl)-7-(N-phenyl-N-1-napthyl)-5,10-diphenyl-indolo[3,2-b]indole, Compound I-27

A mixture of 2-bromo-7-(N-phenyl-N-1-napthyl)-5,10-diphenyl-indolo[3,2-b]indole (0.43 g, 0.66 mmole), benzocarbazole (0.158 g, 0.73 mmole), Pd$_2$(dba)$_3$ (0.012 g, 0.013 mmole), and tri-tert-butylphosphine (0.062 g, 0.011 mmole) in toluene (50 ml) was stirred under nitrogen atmosphere for approximately 1 min followed by addition of sodium tert-butoxide (0.095 g, 0.99 mmol). Reaction mixture was heated at 100 C overnight. After that reaction mixture cooled down, water (50 ml) added and the reaction mixture was stirred in the air for 30 min. Toluene layer separated and passed through layers of celite, florisil and silica gel washing with toluene. Solvent was removed by using rotary evaporator, the residue was redissolved in dichloromethane and evaporated onto celite and purified on silica gel column using hexanes-dichloromethane mixtures as eluent to give 180 mg of the product. This product was subjected to the second column chromatography purification on silica gel using hexanes-dichloromethane mixtures as eluent to give 55 mg of the product with purity 99.13% by UPLC. $^1$H-NMR (CDCl$_3$, 500 MHz): 6.83 (dd, 1H, J=2; 8.5 Hz), 6.90-6.95 (m, 3H), 7.19-7.23 (m, 3H), 7.35-7.76 (m, 21H), 7.83 (d, 2H, J=7.5 Hz), 7.87 (d, 1H, J=9 Hz), 7.90 (t, 2H, J=9 Hz), 7.99 (d, 1H, J=8.5 Hz), 8.06 (d, 1H, J=8 Hz), 7.69 (d, 1H, J=7.5 Hz), 8.86 (d, 1H, J=8.5 Hz). MS: MH+=791. UV-VIS: $\lambda_{max}$=373 nm in toluene. Photoluminescence (toluene): $\lambda_{max}$: 466 nm.

Synthesis Example 24

This example illustrates the preparation of a compound having Formula VIII, Compound VIII-6.
Step a.

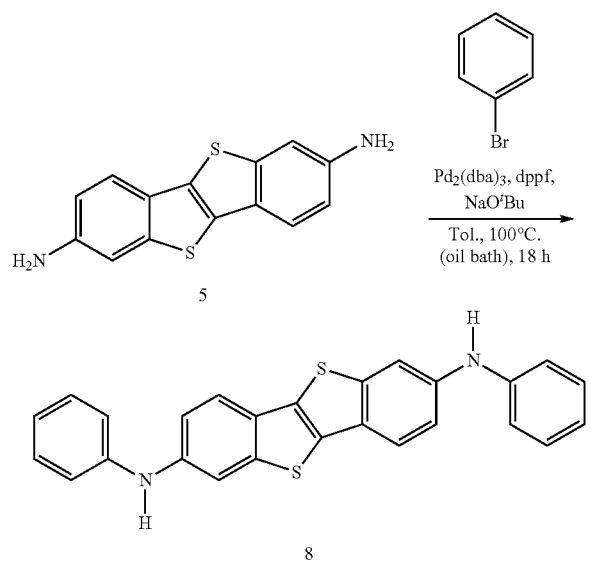

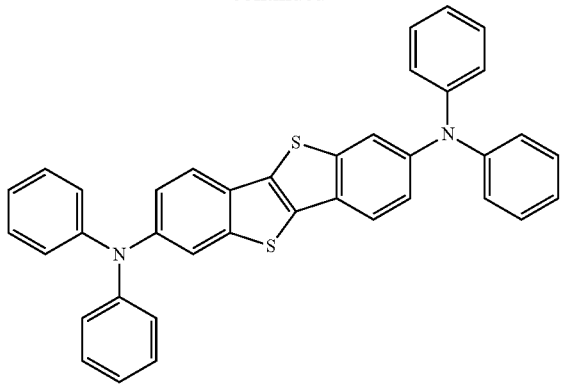

Compound VIII-6

Tris(dibenzylidene-acetone)-dipalladium(0) (0.72 g, 0.78 mmol) and 1,1'-Bis(diphenylphosphino)-ferrocene (0.87 g, 1.57 mmol) were dissolved in toluene under N$_2$. The mixture (purple-red) was stirred at RT for 10 min. Then intermediate 8 (10.0 g, 0.024 mmol), bromobenzene (11.15 g, 0.071 mol) and sodium tert-butoxide (5.46 g, 0.057 mol) were added. The mixture was bubbled with N$_2$ for 15 min. and then heated at 110° C. (oil bath) for 20 h. TLC checked product formed. The reaction mixture (brown with solids) was cooled down and poured into MeOH. The solid was filtered off and washed with diluted HCl, H$_2$O, MeOH (2×) to give 72P-C, 7.23 g, yellow solid. 72P-C was re-dissolved in CHCl$_3$ (not completely dissolved), poured into a short column of silica gel (pre-rinsed with CHCl$_3$ with 1% Et$_3$N), rinsed with CHCl$_3$ (difficulty to dissolve, stirred on the top, ~1.5 L). The fractions were collected and concentrated, MeOH was added, the solid was filtered to give 72P-1, 5.2 g, yellow solid. 72P-1 was purified further by 3-zone sublimation to give 72P-2, 4.1 g, yellow solid, HPLC>99%. The structure was confirmed by NMR analysis.

Tris(dibenzylidene-acetone)-dipalladium(0) (0.72 g, 0.78 mmol) and 1,1'-Bis(diphenylphosphino)-ferrocene (0.87 g, 1.57 mmol) were dissolved in toluene under N$_2$. The mixture (brown) was stirred at RT for 10 min. Then intermediate 5 from Synthesis Example 10 (15.07 g, 0.056 mmol), bromobenzene (21.88 g, 0.14 mol) and sodium tert-butoxide (12.92 g, 0.13 mol) were added. The mixture was bubbled with N$_2$ for 15 min., and heated at 100° C. (oil bath) for 20 h. The reaction mixture (brown with solids) was filtered and rinsed with toluene to give D100675-72D-C, 35.12 g, 149%, brown solid, MS contains product and byproducts.
Step b.

Synthesis Example 25

This example illustrates the preparation of a compound having Formula I, Compound I-29.

Step a. 2-bromo-7-(3-(naphthalen-1-yl)phenyl)-5,10-diphenyl-4b,5,9b,10-tetrahydroindolo[3,2-b]indole

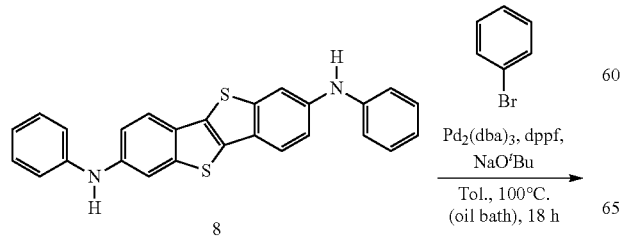

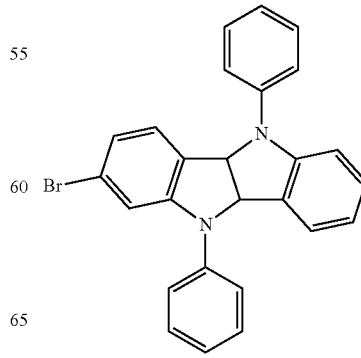

-continued

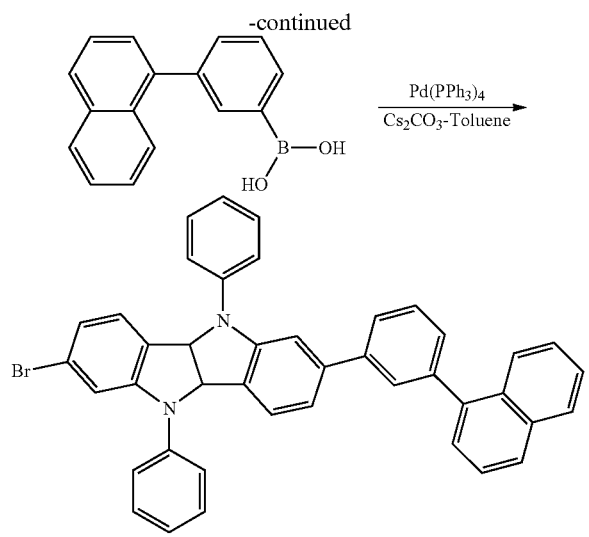

2,7-Dibromo-5,10-diphenyl-4b,5,9b,10-tetrahydroindolo[3,2-b]indole (5.18 g, 10 mmol), (3-(naphthalen-1-yl)phenyl)boronic acid (2.60 g, 10.50 mmol), $Cs_2CO_3$ (13.03 g, 40 mmol), and anhydrous toluene (160 ml) were taken in a 500 mL flask under nitrogen and stirred for 5 min. With stirring, the system was purged with nitrogen for 20 min. $Pd(PPh_3)_4$ (231 mg, 0.20 mmol) was added and the system was purged for another 15 min. The reaction was stirred and refluxed under nitrogen for 16 hours. UPLC analysis indicated that the reaction is a mixture of starting 2,7-dibromo-5,10-diphenyl-4b,5,9b,10-tetrahydroindolo[3,2-b]indole, the mono-coupled 2-bromo-7-(3-(naphthalen-1-yl)phenyl)-5,10-diphenyl-4b,5,9b,10-tetrahydroindolo[3,2-b]indole and the disubstituted 2,7-bis(3-(naphthalen-1-yl)phenyl)-5,10-diphenyl-5,10-dihydroindolo[3,2-b]indole, in a ratio of about 25:50:25. The reaction mixture was passed through a layer of Celit to remove the insoluble material eluted with toluene. The solution was washed with water, aq. HCl (10%, 100 mL), saturated brine and dride with $MgSO_4$. After filtering, the solvent was removed by rotary evaporation and the residue was separated on a Silica gel column eluted with chloroform/hexane gradient. The product containing fractions were identified by UPLC and collected. The product was obtained as a pale yellow amorphous solid, 4.06 g in 99.1% purity by UPLC analysis.

Step b. (E)-2-(4-(4-(tert-butyl)styryl)phenyl)-7-(3-(naphthalen-1-yl)phenyl)-5,10-diphenyl-5,10-dihydroindolo[3,2-b]indole, Compound I-29

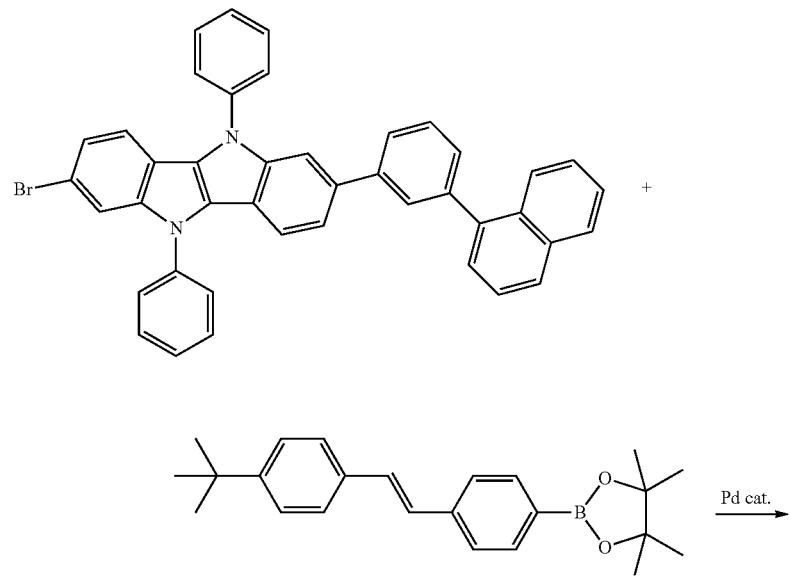

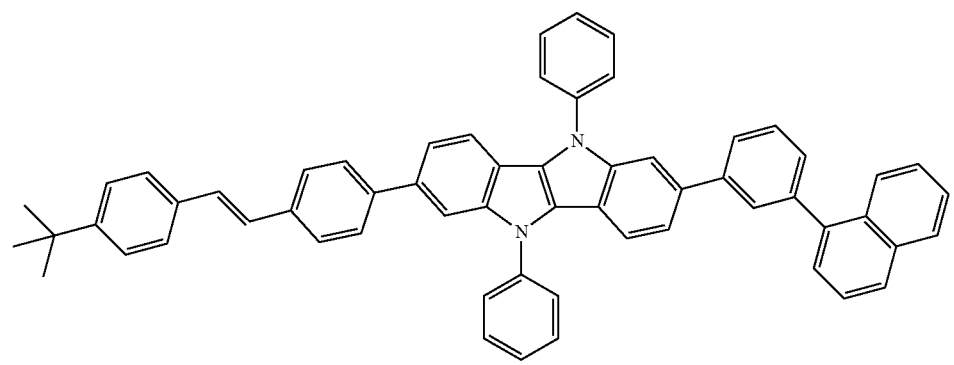

2-Bromo-7-(3-(naphthalen-1-yl)phenyl)-5,10-diphenyl-4b,5,9b,10-tetrahydroindolo[3,2-b]indole (2.00 g, 3.12 mmol), E)-2-(4-(4-(tert-butyl)styryl)phenyl)-4,4,5,5-tetramethyl-1,3,2-dioxaborolane (1.19 g, 3.28 mmol), $Cs_2CO_3$ (4.07 g, 12.51 mmol), and anhydrous toluene (80 mL) were taken in a 200 mL flask under nitrogen and stirred for 5 min. With stirring, the system was purged with nitrogen for 20 min. $Pd(PPh_3)_4$ (72 mg, 0.06 mmol) was added and the system was purged for another 15 min. The reaction was stirred and refluxed under nitrogen for 16 hours. The reaction mixture was passed through a layer of Celit to remove the insoluble material eluted with toluene. The solvent was removed by rotary evaporation and the residue was separated on a Silica gel column eluted with chloroform/hexane gradient. The product containing fractions were identified by UPLC and collected. The solvent was removed and the residue was crystallized from toluene/acetonitrile to give 1.7 g of yellow crystalline solid in 99.9% purity by UPLC analysis.

Synthesis Example 26

This example illustrates the preparation of a compound having Formula I, Compound I-30.

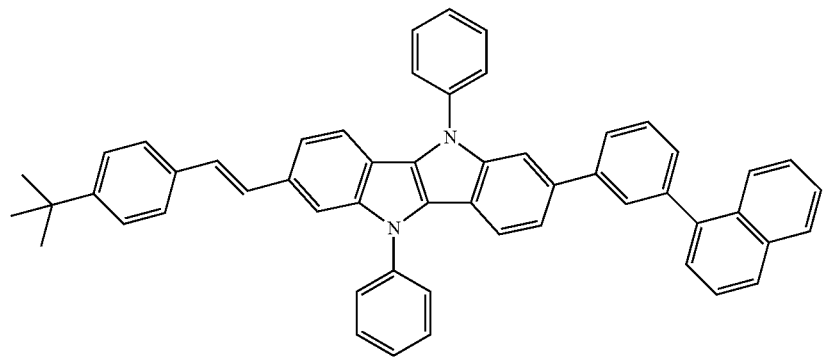

Step a. (E)-2-(4-(tert-butyl)styryl)-4,4,5,5-tetramethyl-1,3,2-dioxaborolane

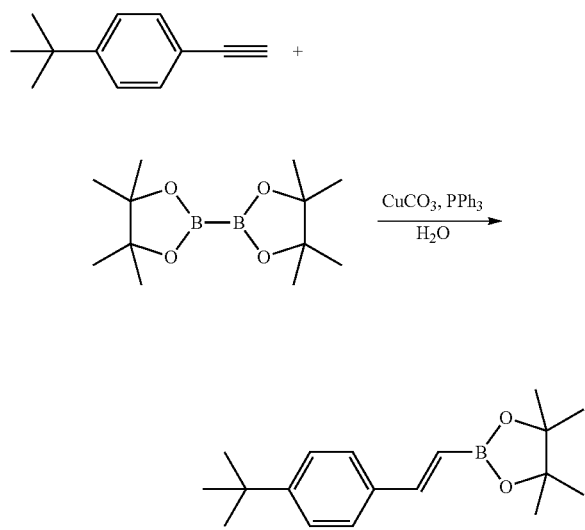

In a dry two-necked round bottom flask were placed catalyst $CuCO_3$ basic (29.36 g, 100 mmol) and triphenyl phosphin (1.70 g, 6.50 mmol) under the nitrogen atmosphere. Afterwards, 250 mL of deionized water was added and reaction mixture was vigorously (800-900 rpm) stirred at ambient temperature for 15 min. The β-borylating reagent 4,4,4',4',5,5,5',5'-octamethyl-2,2'-bi(1,3,2-dioxaborolane) (18.50 g, 110 mmol) was added in one portion and such reaction mixture was stirred at ambient temperature for another 30 min. Starting material 1-(tert-butyl)-4-ethynyl-benzene (15.82 g, 100 mmol) was slowly added into the reaction and the mixture was intensively stirred at 27° C. overnight. The reaction mixture was diluted with brine (350 mL) and extracted with EtOAc (3×200 mL). Combined organic layers were again washed with saturated brine (200 mL), dried over $Na_2SO_4$ and organic solvent was removed under the reduced pressure. The crude product was purified with column chromatography ($SiO_2$; n-hexane/DCM) and crystallized from hexane to give 19 g of white crystalline solid 98% purity by UPLC analysis. The structure was determined with 1H and 13C NMR analysis.

Step b. (E)-2-(4-(tert-butyl)styryl)-7-(3-(naphthalen-1-yl)phenyl)-5,10-diphenyl-5,10-dihydroindolo[3,2-b]indole

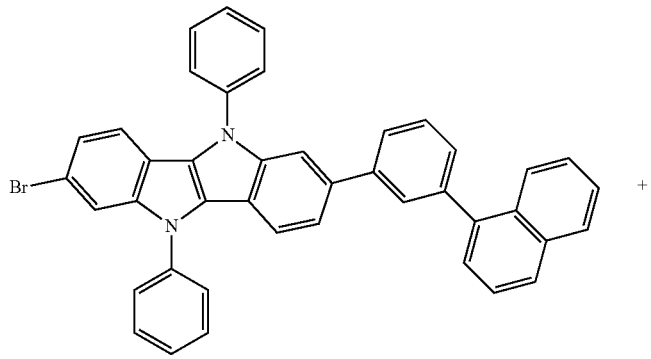

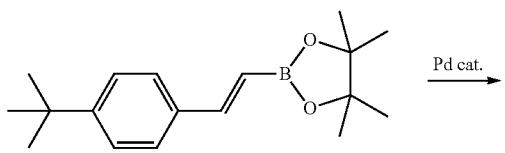

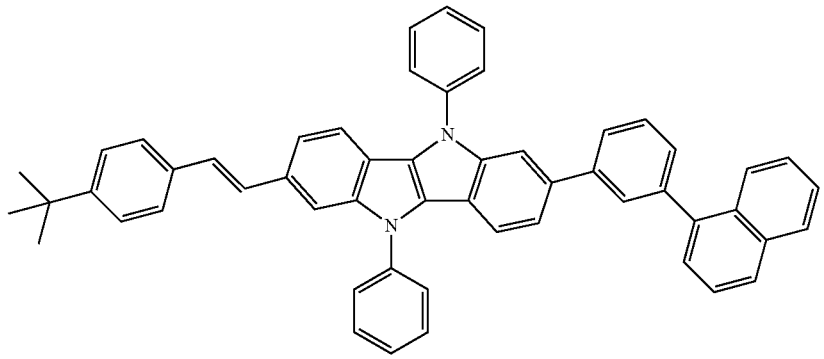 [SMILES: CC(C)(C)c1ccc(/C=C/c2ccc3c(c2)n(-c2ccccc2)c2c4ccc(-c5cccc(-c6cccc7ccccc67)c5)cc4n(-c4ccccc4)c32)cc1]

2-Bromo-7-(3-(naphthalen-1-yl)phenyl)-5,10-diphenyl-4b,5,9b,10-tetrahydroindolo[3,2-b]indole (2.00 g, 3.12 mmol), (E)-2-(4-(tert-butyl)styryl)-4,4,5,5-tetramethyl-1,3,2-dioxaborolane (0.94 g, 3.28 mmol), $Cs_2CO_3$ (4.07 g, 12.51 mmol), and anhydrous toluene (80 mL) were taken in a 200 mL flask under nitrogen and stirred for 5 min. With stirring, the system was purged with nitrogen for 20 min. $Pd(PPh_3)_4$ (72 mg, 0.06 mmol) was added and the system was purged for another 15 min. The reaction was stirred and refluxed under nitrogen for 16 hours. The reaction mixture was passed through a layer of Celit to remove the insoluble material eluted with toluene. The solvent was removed by rotary evaporation and the residue was separated twice on Silica gel column eluted with chloroform/hexane gradient. The product containing fractions were identified by UPLC and collected. The solvent was removed and the product was precipitated from toluene (5 mL) into acetonitrile to give 1.8 g of yellow amorphous solid in 99.9% purity by UPLC analysis.

Synthesis Example 27

This example illustrates the preparation of a compound having Formula I, Compound I-31.

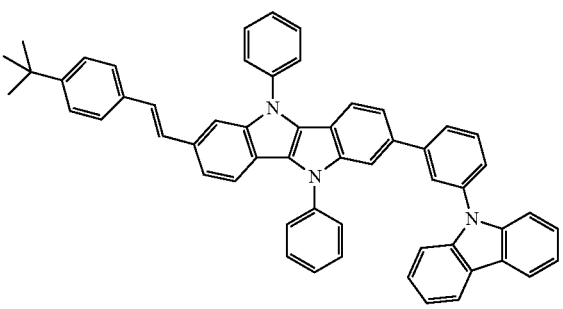 [SMILES: CC(C)(C)c1ccc(/C=C/c2ccc3c(c2)n(-c2ccccc2)c2c4ccc(-c5cccc(-n6c7ccccc7c7ccccc76)c5)cc4n(-c4ccccc4)c32)cc1]

119

Step a. (E)-2-bromo-7-(4-(tert-butyl)styryl)-5,10-diphenyl-5,10-dihydroindolo[3,2-b]indole

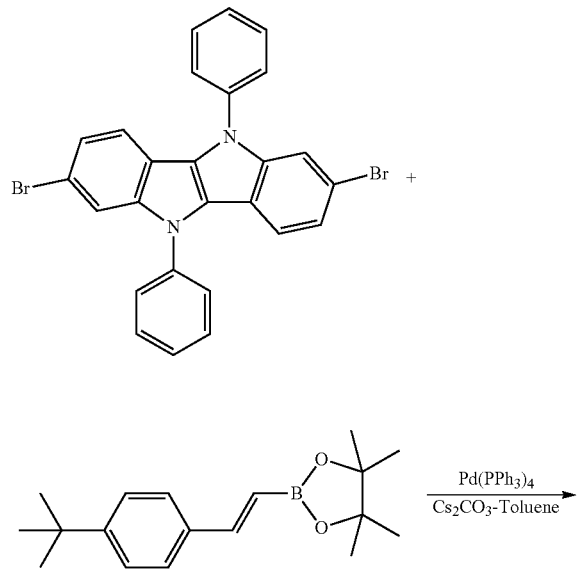

120

Step b. ((E)-2-(3-(9H-carbazol-9-yl)phenyl)-7-(4-(tert-butyl)styryl)-5,10-diphenyl-5,10-dihydroindolo[3,2-b]indole

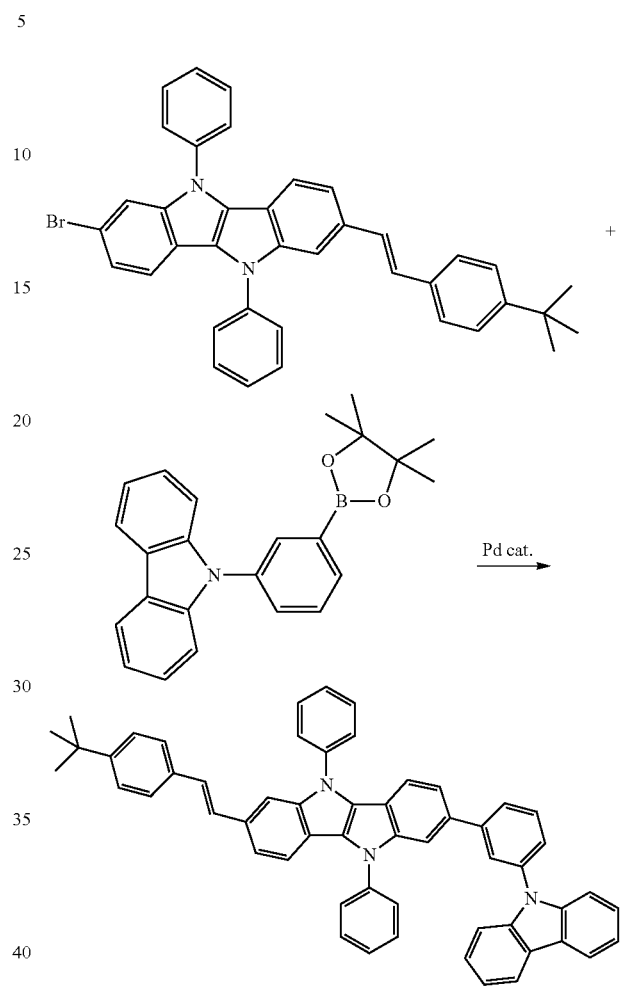

In dry box, 2,7-dibromo-5,10-diphenyl-5,10-dihydroindolo[3,2-b]indole (7.74 g, 15 mmol), (E)-2-(4-(tert-butyl)styryl)-4,4,5,5-tetramethyl-1,3,2-dioxaborolane (4.51 g, 15 mmol), $Cs_2CO_3$ (19.55 g, 60 mmol), $Pd(PPh_3)_4$ (347 mg, 0.30 mmol) and anhydrous toluene (225 mL) were taken in a 500 mL flask. The reaction was stirred and refluxed under nitrogen for 16 hours. UPLC analysis indicated that the product was formed in about 60% together with unreacted starting dibromide and the disubstituted byproduct in about 20% respectively. The reaction mixture was passed through a layer of Celit to remove the insoluble material eluted with toluene. The solvent was removed by rotary evaporation and 5.2 g of the crude product was used to be separated on Silica gel column eluted with DCM/hexane gradient. The product containing fractions were identified by UPLC and collected. The solvent was removed and the product was crystallized from toluene/ethanol to give 2.8 g of yellow crystalline solid in 99.5% purity by UPLC analysis.

In dry box, (E)-2-bromo-7-(4-(tert-butyl)styryl)-5,10-diphenyl-5,10-dihydroindolo[3,2-b]indole (1.37 g, 2.30 mmol), 9-(3-(4,4,5,5-tetramethyl-1,3,2-dioxaborolan-2-yl)phenyl)-9H-carbazole (0.89 g, 2.41 mmol), $Cs_2CO_3$ (2.99 g, 12.51 mmol), $Pd(PPh_3)_4$ (53 mg, 0.05 mmol) and anhydrous toluene (100 mL) were taken in a 250 mL flask. The reaction was stirred and refluxed under nitrogen for 16 hours. The reaction mixture was passed through a layer of Celit to remove the insoluble material eluted with toluene. The solvent was removed by rotary evaporation and the residue was separated twice on Silica gel column eluted with DCM/hexane gradient. The product containing fractions were identified by UPLC and collected. The solvent was removed and the product was crystallized from toluene/acetonitrile to give 0.5 g of yellow crystalline solid in 99.9% purity by UPLC analysis.

Synthesis Example 28

This example illustrates the preparation of a compound having Formula I, Compound I-32.

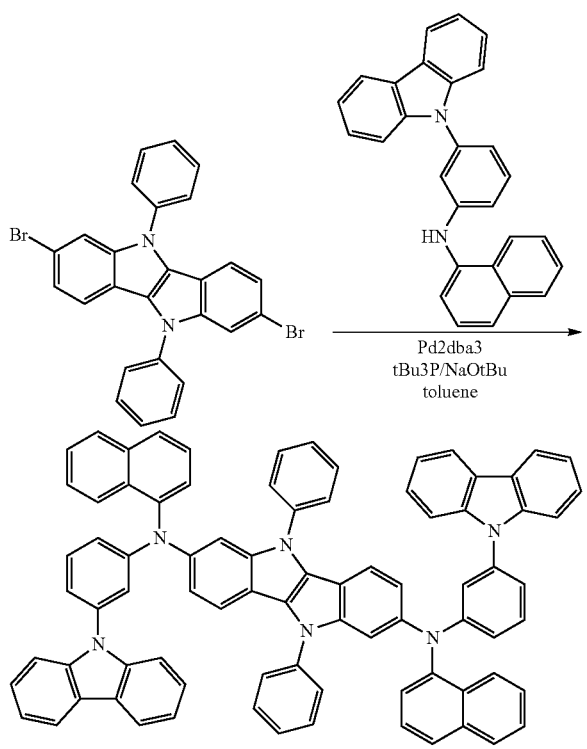

To a mixture of 2,7-dibromo-5,10-diphenyl-5,10-dihydro-indolo[3,2-b]indole (1.5 g, 2.91 mmole), N-(3-carazolyl)-phenyl-N-1-napthylamine (1.40 g, 3.64 mmole) and sodium tert-butoxide (0.42 g, 4.37 mmol) in toluene (80 ml) was added a mixture of $Pd_2(dba)_3$ (0.055 g, 0.060 mmole) and 1,1'-bis(diphenylphosphino)ferrocene (0.067 g, 0.12 mmole) in toluene (20 ml) with stirring under nitrogen atmosphere. Reaction mixture was heated at 106 C overnight. After that reaction mixture cooled down, water (60 ml) added and the reaction mixture was stirred in the air for 1 hour. Toluene layer separated, water phase extracted with toluene, combined toluene solution dried over sodium sulfate and passed through layers of celite, florisil and basic alumina washing with toluene. Solvent was removed by using rotary evaporator, the residue was redissolved in dichloromethane and evaporated onto celite and purified on silica gel column using hexanes-dichloromethane mixtures as eluent. Fractions containing product combined, eluent evaporated by using rotary evaporator. The residue after evaporation of eluent was redissolved in hot toluene and precipitate formed upon cooling to ambient temperature was filtered, washed with toluene and hexanes and dried in vacuum to give 0.52 g of the product with purity 99.17% by UPLC. MS: MH+=1123. UV-VIS: $\lambda_{max}$=393 nm in toluene. Photoluminescence (toluene): $\lambda_{max}$: 485 nm.

Example 1

This example illustrates the photoluminescence of compounds having Formula I.

The compounds were individually dissolved in toluene. The concentration was adjusted such that the optical density of the solution in a 1-cm quartz cell was preferably in the 0.2-0.4 range, at the excitation wavelengths between 300 and 360 nm. The photoluminescence spectrum was measured with a Spex Fluorolog spectrometer. The results are given in Table 1 below, where "PL" indicates photoluminescence.

TABLE 1

| Compound | PL peak, nm | PL FWHM, nm |
|---|---|---|
| I-12 | 495 | 93 |
| I-18 | 425 | 41 |
| I-19 | 407 | 56 |
| I-22 | 436 | 62 |
| I-23 | 391 | 43 |
| I-24 | 433 | 58 |
| I-25 | 438 | 57 |
| I-26 | 437 | 63 |
| I-27 | 466 | 78 |
| I-29 | 446 | 65 |
| I-30 | 445 | 68 |
| I-31 | 446 | 69 |
| I-32 | 485 | 93 |
| II-3 | 424 | 64 |
| II-5 | 471 | 29 |
| II-6 | 472 | 33 |
| VI-2* | 451 | 46 |
| VI-2** | 452 | 47 |

*indicates the higher molecular weight polymer from Synthesis Ex. 16.
**indicates the lower molecular weight polymer from Synthesis Ex. 16.

DEVICE EXAMPLES (1) Materials
Dopant D1 is shown below

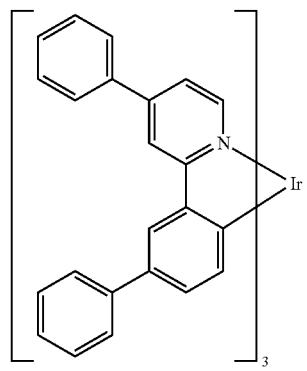

ET-1 is shown below

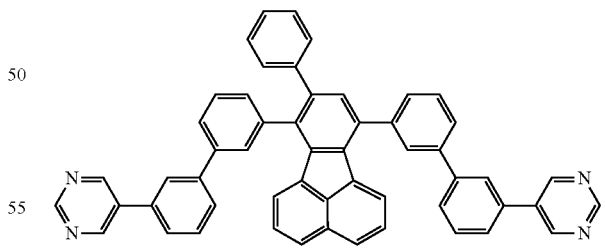

ET-2 is lithium quinolate.
ET-3 is a metal quinolate complex.
ET-4 is CsF.
ET-5 is an aryl phosphine oxide.
HIJ-1 and HIJ-2 are hole injection materials which are made from an aqueous dispersion of an electrically conductive polymer and a polymeric fluorinated sulfonic acid. Such materials have been described in, for example, published U.S. patent applications US 2004/0102577, US 2004/

0127637, and US 2005/0205860, and published PCT application WO 2009/018009.

Host H1 is a diarylanthracene compound

Host H2 is a deuterated diarylanthracene compound

Host H3 is a deuterated indolocarbazole

HTM-1 is a hole transport material which is a fluorene-triarylamine copolymer

HTM-2 is a hole transport material which is a binaphthyl-triarylamine polymer

HTM-3 is a hole transport material which is a triarylamine polymer. Such materials have been described in, for example, published US Application 2013-0082251.

HTM-4 is an aromatic compound having multiple phenyl groups. The compound can be made using known C—C coupling techniques. Such materials have been described in, for example, published PCT Application WO 2015089304.

(2) Device Fabrication

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Device Type 1: Immediately before device fabrication the cleaned, patterned ITO substrates were treated with UV ozone for 10 minutes. Immediately after cooling, an aqueous dispersion of hole injection material was spin-coated over the ITO surface and heated to remove solvent. After cooling, the substrates were then spin-coated with a toluene solution of hole transport material, and then heated to remove solvent. After cooling the substrates were spin-coated with a methyl benzoate solution of the host and dopant, and heated to remove solvent. The substrates were masked and placed in a vacuum chamber. A layer of electron transport material was deposited by thermal evaporation, followed by a layer of electron injection material. Masks were then changed in vacuo and a layer of Al was deposited by thermal evaporation. The chamber was vented, and the devices were encapsulated using a glass lid, dessicant, and UV curable epoxy.

Device Type 2: Immediately before device fabrication the cleaned, patterned ITO substrates were treated with UV ozone for 10 minutes. Immediately after cooling, an aqueous dispersion of hole injection material was spin-coated over the ITO surface and heated to remove solvent. After cooling, the substrates were then spin-coated with a toluene solution of hole transport material, and then heated to remove solvent. After cooling, the workpieces were placed in a vacuum chamber. Layers of the photoactive and host materials, electron transport materials, and the Al cathode were then deposited sequentially by thermal evaporation using the appropriate masks. The chamber was vented, and the devices were encapsulated using a glass lid, desiccant, and UV curable epoxy.

(3) Device Characterization

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W. The color coordinates were determined using either a Minolta CS-100 meter or a Photoresearch PR-705 meter.

Device Example 1

This example demonstrates the fabrication and performance of a device including a photoactive layer with a compound of Formula I having green emission. The device was made as described above for Device Type 1.

Device structure, in order (all percentages are by weight, based on the total weight of the layer):

Glass Substrate

Anode: indium tin oxide ("ITO") (50 nm)

Hole injection layer: HIJ-1 (50 nm)

Hole transport layer: HTM-2 (20 nm)

Photoactive layer: host H1 and Compound I-1 (60 nm) with a host/dopant ratio of 13:1

Electron transport layer: ET-3 (10 nm)

Electron injection layer: ET-4 (0.7 nm)

Cathode: Al (100 nm)

The device results are as follows:

Current efficiency=15.2 cd/A

Quantum efficiency=6.6%

Power efficiency=10.5 lm/W

Voltage @ 300 A/m$^2$=5.6

Color coordinates according to the C.I.E. chromaticity scale (Commission Internationale de L'Eclairage, 1931):

x=0.160, y=0.411

Time to reach ½ initial luminance=96,791 h @1000 nits, 20° C.

Device Examples 2-4

These examples demonstrate the fabrication and performance of a device including a photoactive layer with a compound of Formula I having green emission. The devices were made as described above for Device Type 1.

Device structure, in order (all percentages are by weight, based on the total weight of the layer):

Glass Substrate

Anode: ITO (180 nm)

Hole injection layer: HIJ-2 (100 nm)

First hole transport layer: HTM-1 (3-5 nm)

Second hole transport layer: HTM-3 (100 nm)

Photoactive layer: host H2 and photoactive dopant (40 nm), the dopant and host/dopant ratio are given below in Table 2

Electron transport layer: ET-1 (20 nm)

Electron injection layer: ET-2 (3.5 nm)

Cathode: Al (100 nm)

The device results are given below in Table 2

TABLE 2

Device results

| Ex | Dopant | Ratio | CE Cd/A | EQE % | CIEx | CIEy | PE Lm/W | T80 (h) | T70 (h) | Curr. Dens. |
|---|---|---|---|---|---|---|---|---|---|---|
| 2 | Comp. I-1 | 99:1 | 8.2 | 6.0 | 0.14 | 0.19 | 5.1 | 1000 | | 33.8 |
| 3 | Comp. I-2 | 93:7 | 3.5 | 3.6 | 0.143 | 0.117 | 2.0 | | 590 | 25.2 |
| 4 | Comp. I-2 | 98:2 | 2.6 | 3.6 | 0.146 | 0.080 | 1.4 | | 280 | 35.4 |

Ratio is the weight ratio of host:dopant;
CE is the current efficiency;
EQE = external quantum efficiency;
CIEx and CIEy are the x and y color coordinates according to the C.I.E. chromaticity scale (Commission Internationale de L'Eclairage, 1931);
PE is the power efficiency.
T80 is the time in hours for a device to reach 80% of the initial luminance at the current density (mA/cm2) given and temperature = 50° C.
T70 is the time in hours for a device to reach 70% of the initial luminance at the current density given(mA/cm2) and temperature = 50° C.

Device Example 5

This example demonstrates the fabrication and performance of a device including a photoactive layer with a compound of Formula I as a host material. The device was made as described above for Device Type 1.

Device structure, in order (all percentages are by weight, based on the total weight of the layer):
Glass Substrate
Anode: ITO (50 nm)
Hole injection layer: HIJ-2 (51.5 n m)
Hole transport layer: HTM-2 (21.5 nm)
Photoactive layer: Compound I-3, Host H3 and dopant D1 in the weight ratio 17:67:16 (61 nm)
Electron transport layer: ET-3 (10 nm)
Electron injection layer: ET-4 (0.7 nm)
Cathode: Al (100 nm)
The device results are given below in Table 3

TABLE 3

Device results

| Ex. | CE Cd/A | QE % | CIEx | CIEy | PE Lm/W | T70 (h) |
|---|---|---|---|---|---|---|
| 5 | 56.1 | 17.4 | 0.468 | 0.524 | 50.5 | 219.0 |

CE is the current efficiency;
EQE = external quantum efficiency;
CIEx and CIEy are the x and y color coordinates according to the C.I.E. chromaticity scale (Commission Internationale de L'Eclairage, 1931);
PE is the power efficiency.
T70 is the time in hours for a device to reach 70% of the initial luminance at current density (mA/cm2) = 37.8 and temperature = 20° C.

Device Examples 6-11

These examples demonstrate the fabrication and performance of devices including a photoactive layer with a compound having Formula I, Compound I-29.

In Device Examples 6-8, the devices were made as described above for Device Type 1. The device structure was, in order (all percentages are by weight, based on the total weight of the layer):
Glass Substrate
Anode: ITO (50 nm)
Hole injection layer: HIJ-2 (100 nm)
Hole transport layer: 8:2 (by weight) HTM-3:HTM-4 (100 nm)
Photoactive layer: Host H2: dopant Compound I-29 in the weight ratios given below (38 nm)
Electron transport layer: ET-1 (20 nm)
Electron injection layer: ET-2 (3.8 nm)
Cathode: Al (100 nm)

In Device Examples 9-11, the devices were made as described above for Device Type 2. The device structure was, in order (all percentages are by weight, based on the total weight of the layer):
Glass Substrate
Anode: ITO (50 nm)
Hole injection layer: HIJ-2 (60 nm)
Hole transport layer: HTM-3 (18 nm)
Photoactive layer: Host H2: dopant Compound I-29 in the weight ratios given below (20 nm)
Electron transport layer: 3:2 (by weight) ET-5:ET-2 (20 nm)
Electron injection layer: ET-2 (3.8 nm)
Cathode: Al (100 nm)
The device results are given below in Table 4.

TABLE 4

Device results

| Ex. | Ratio | CE (cd/A) | EQE (%) | CIEx | CIEy | V | Lifetest luminance (nits) | T95 (h) |
|---|---|---|---|---|---|---|---|---|
| 6 | 93:7 | 6.4 | 6.2 | 0.142 | 0.123 | 5.0 | 1401 | 500 |
| 7 | 99:1 | 4.7 | 5.4 | 0.144 | 0.099 | 4.9 | 1039 | 225 |
| 8 | 96:4 | 6.2 | 6.2 | 0.142 | 0.117 | 5.0 | 1353 | 422 |
| 9 | 20:1 | 10.2 | 8.2 | 0.143 | 0.159 | 3.9 | 1678 | 418 |
| 10 | 13:1 | 10.6 | 8.2 | 0.143 | 0.167 | 3.8 | 1757 | 570 |
| 11 | 32:1 | 9.1 | 7.7 | 0.143 | 0.146 | 4.0 | 1503 | 350 |

All data at 1000 nits except for lifetest.
Ratio is the weight ratio of host:dopant;
CE is the current efficiency;
EQE = external quantum efficiency;
CIEx and CIEy are the x and y color coordinates according to the C.I.E. chromaticity scale (Commission Internationale de L'Eclairage, 1931);
V is the voltage at 15 mA/cm2;
T95 is the time in hours for a device to reach 95% of the initial luminance at temperature = 50° C. and current density of 22 mA/cm2 for Ex. 6-8 and 16.5 mA/cm2 for Ex. 9-11.

Device Examples 12-17

These examples demonstrate the fabrication and performance of devices including a photoactive layer with a compound having Formula I, Compound I-30.

Device Examples 12-14 were carried out the same as Device Examples 6-8, except that Compound I-30 was used as the dopant.

Device Examples 15-17 were carried out the same as Device Examples 9-11, except that Compound I-30 was used as the dopant.

The results are given in Table 5.

TABLE 5

Device results

| Ex. | Ratio | CE (cd/A) | EQE (%) | CIEx | CIEy | V | Lifetest luminance (nits) | T95 (h) |
|---|---|---|---|---|---|---|---|---|
| 12 | 93:7 | 7.0 | 6.0 | 0.139 | 0.148 | 5.2 | 1549 | 340 |
| 13 | 99:1 | 6.2 | 6.0 | 0.140 | 0.123 | 5.1 | 1365 | 350 |
| 14 | 96.5:3.5 | 7.0 | 6.4 | 0.139 | 0.136 | 5.2 | 1540 | 370 |
| 15 | 20:1 | 11.7 | 8.3 | 0.142 | 0.195 | 4.1 | 1929 | 620 |
| 16 | 32:1 | 10.2 | 7.9 | 0.142 | 0.174 | 4.2 | 1690 | 460 |
| 17 | 13:1 | 11.7 | 8.0 | 0.143 | 0.207 | 4.0 | 1936 | 800 |

All data at 1000 nits except for lifetest.
Ratio is the weight ratio of host:dopant;
CE is the current efficiency;
EQE = external quantum efficiency;
CIEx and CIEy are the x and y color coordinates according to the C.I.E. chromaticity scale (Commission Internationale de L'Eclairage, 1931);
V is the voltage at 15 mA/cm2;
T95 is the time in hours for a device to reach 95% of the initial luminance at temperature = 50° C. and current density of 22 mA/cm2 for Ex. 12-14 and 16.5 mA/cm2 for Ex. 15-17.

Device Examples 18-27

These examples demonstrate the fabrication and performance of devices including a photoactive layer with a compound having Formula I.

The devices were made as described above for Device Type 1. The device structure was, in order (all percentages are by weight, based on the total weight of the layer):

Glass Substrate

Anode: ITO (50 nm)

Hole injection layer: HIJ-2 (40 nm)

Hole transport layer: 6:4 (by weight) HTM-3:HTM-4 (19 nm)

Photoactive layer: Host H2: dopant in the weight ratios given below (38 nm)

Electron transport layer: 3:2 (by weight) ET-5:ET-2 (20 nm)

Cathode: Al (100 nm)

The dopant, host:dopant ratios, and device results are given in Table 6.

TABLE 6

Device results

| Ex. | Dopant Compound | Ratio | CE (cd/A) | EQE (%) | CIEx | CIEy | V | Lifetest lum. (nits) | T95 (h) |
|---|---|---|---|---|---|---|---|---|---|
| 18 | I-31 | 93:7 | 7.7 | 5.6 | 0.143 | 0.181 | 4.1 | 1691 | 300 |
| 19 | I-31 | 96.5:3.5 | 7.7 | 5.9 | 0.143 | 0.169 | 4.2 | 1690 | 320 |
| 20 | I-22 | 96.5:3.5 | 4.6 | 4.4 | 0.147 | 0.118 | 4.6 | 1003 | 5 |
| 21 | I-23 | 96:4 | 1.6 | 2.2 | 0.153 | 0.076 | 4.1 | 347 | 233 |
| 22 | I-25 | 96:4 | 5.9 | 5.2 | 0.145 | 0.138 | 4.6 | 1295 | 70 |
| 23 | I-25 | 98:2 | 5.3 | 4.9 | 0.146 | 0.130 | 4.6 | 1171 | 140 |
| 24 | I-25 | 99:1 | 4.2 | 4.1 | 0.147 | 0.119 | 4.6 | 934 | 350 |
| 25 | I-27 | 93:7 | 5.2 | 2.3 | 0.186 | 0.344 | 5.3 | — | — |
| 26 | I-27 | 96:4 | 5.5 | 2.5 | 0.178 | 0.300 | 5.3 | — | — |
| 27 | I-27 | 91:9 | 4.7 | 2.4 | 0.191 | 0.361 | 5.3 | — | — |

All data at 1000 nits except for lifetest.
Ratio is the weight ratio of host:dopant;
CE is the current efficiency;
EQE = external quantum efficiency;
CIEx and CIEy are the x and y color coordinates according to the C.I.E. chromaticity scale (Commission Internationale de L'Eclairage, 1931);
V is the voltage at 15 mA/cm2;
T95 is the time in hours for a device to reach 95% of the initial luminance at temperature = 50° C. and current density of 22 mA/cm2.

Device Examples 28-30

These examples demonstrate the fabrication and performance of devices including a photoactive layer with a compound having Formula I, Compound I-21.

The devices were made as described above for Device Type 2. The device structure was, in order (all percentages are by weight, based on the total weight of the layer):

Glass Substrate

Anode: ITO (50 nm)

Hole injection layer: HIJ-2 (100 nm)

Hole transport layer: 8:2 (by weight) HTM-3:HTM-4 (105 nm)

Photoactive layer: Host H2: dopant Compound I-21 in the weight ratios given below (33 nm)

Electron transport layer: ET-1 (20 nm)

Electron injection layer: ET-2 (3.8 nm)

Cathode: Al (100 nm)

The host:dopant ratio and the device results are given in Table 7.

TABLE 7

Device results

| Ex. | Ratio | CE (cd/A) | EQE (%) | CIEx | CIEy | V | Lifetest luminance (nits) | T95 (h) |
|---|---|---|---|---|---|---|---|---|
| 28 | 13:1 | 10.4 | 8.0 | 0.144 | 0.171 | 4.0 | 1683 | 60 |
| 29 | 32:1 | 10.4 | 7.8 | 0.144 | 0.175 | 4.0 | 1721 | 100 |
| 30 | 99:1 | 8.6 | 7.9 | 0.144 | 0.129 | 4.0 | 1425 | 80 |

All data at 1000 nits except for lifetest.
Ratio is the weight ratio of host:dopant;
CE is the current efficiency;
EQE = external quantum efficiency;
CIEx and CIEy are the x and y color coordinates according to the C.I.E. chromaticity scale (Commission Internationale de L'Eclairage, 1931);
V is the voltage at 15 mA/cm2;
T95 is the time in hours for a device to reach 95% of the initial luminance at temperature = 50° C. and current density of 16.5 mA/cm2.

Device Examples 31-40

These examples demonstrate the fabrication and performance of devices including a photoactive layer with a polymer having Formula II or Formula VI.

The devices were made as described for Device Type 1.

Examples 31-32 were carried out as in Devices Examples 6-8, but with different dopants. Examples 33-40 were carried out as in Device Examples 18-27, but with different dopants.

The dopants, host:dopant ratio, and the device results are given in Table 8.

TABLE 8

Device results

| Ex. | Dopant Compound | Ratio | CE (cd/A) | EQE (%) | CIEx | CIEy | V |
|---|---|---|---|---|---|---|---|
| 31 | II-5 | 96:4 | 3.4 | 2.8 | 0.129 | 0.193 | 4.7 |
| 32 | II-5 | 98:2 | 3.7 | 3.0 | 0.134 | 0.192 | 4.7 |
| 33 | II-6 | 93:7 | 3.0 | 2.1 | 0.140 | 0.211 | 5.3 |
| 34 | II-6 | 97:3 | 4.1 | 3.0 | 0.143 | 0.184 | 4.5 |
| 35 | II-6 | 85:15 | 2.8 | 2.0 | 0.141 | 0.219 | 5.8 |
| 36 | VI-2* | 93:7 | 1.0 | 0.7 | 0.158 | 0.204 | 3.3 |
| 37 | VI-2** | 93:7 | 1.5 | 1.1 | 0.149 | 0.175 | 3.3 |
| 38 | VI-2** | 96.5:3.5 | 3.3 | 2.7 | 0.142 | 0.160 | 4.1 |
| 39 | VI-2** | 98:2 | 3.6 | 3.0 | 0.142 | 0.150 | 4.3 |
| 40 | VI-2** | 99:1 | 3.0 | 2.8 | 0.145 | 0.132 | 4.3 |

*indicates the higher molecular weight polymer from Synthesis Ex. 16
**indicates the lower molecular weight polymer from Synthesis Ex. 16
All data at 1000 nits.
Ratio is the weight ratio of host:dopant;
CE is the current efficiency;
EQE = external quantum efficiency;
CIEx and CIEy are the x and y color coordinates according to the C.I.E. chromaticity scale (Commission Internationale de L'Eclairage, 1931);
V is the voltage at 15 mA/cm2.

Device Examples 41-42

These examples demonstrate the fabrication and performance of devices including a photoactive layer with a compound having Formula VIII, Compound VIII-6.

The examples were carried out the same as Device Examples 6-8, with liquid deposition of the photoactive layer, but with Compound VIII-6. The host:dopant ratio and the device results are given in Table 8.

TABLE 8

Device results

| Ex. | Ratio | CE (cd/A) | EQE (%) | CIEx | CIEy | V |
|---|---|---|---|---|---|---|
| 41 | 99:1 | 1.4 | 2.5 | 0.151 | 0.057 | 4.9 |
| 42 | 93:7 | 1.0 | 1.4 | 0.150 | 0.078 | 5.0 |

All data at 1000 nits.
Ratio is the weight ratio of host:dopant;
CE is the current efficiency;
EQE = external quantum efficiency;
CIEx and CIEy are the x and y color coordinates according to the C.I.E. chromaticity scale (Commission Internationale de L'Eclairage, 1931);
V is the voltage at 15 mA/cm2.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. A compound having Formula I

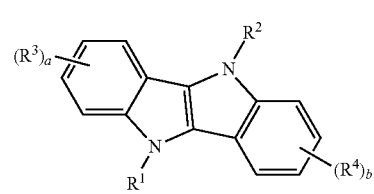

(I)

wherein:
R$^1$ and R$^2$ are the same or different at each occurrence and are selected from the group consisting of alkyl, silyl, germyl, hydrocarbon aryl, N-heteroaryl, O-heteroaryl, S-heteroaryl, N,O-heteroaryl, and deuterated analogs thereof;
R$^3$ and R$^4$ are the same or different at each occurrence and are selected from the group consisting of alkoxy, siloxy, siloxane, alkenylaryl, aryloxy, deuterated alkoxy, deuterated siloxy, deuterated siloxane, deuterated alkenylaryl, and deuterated aryloxy;
a is an integer from 1-4; and
b is an integer from 0-4;
wherein the N-heteroaryl is derived from a compound selected from the group consisting of pyrrole, pyridine, pyrimidine, carbazole, imidazole, benzimidazole, imidazolobenzimidazole, triazole, benzotriazole, triazolopyridine, indole, indolocarbazole, phenanthroline, quinoline, isoquinoline, quinoxaline, substituted derivatives thereof, and deuterated analogs thereof;

wherein the O-heteroaryl is derived from a compound selected from the group consisting of furan, benzofuran, dibenzofuran, substituted derivatives thereof, and deuterated analogs thereof;

wherein the S-heteroaryl is derived from a compound selected form the group consisting of thiophene, benzothiophene, dibenzothiophene, substituted derivatives thereof, and deuterated analogs thereof; and wherein the N,O-heteroaryl is derived from a compound selected from the group consisting of oxazole, benzoxazole, phenoxazine, substituted derivatives thereof, and deuterated analogs thereof;

wherein the substituted derivatives have substituents selected from the group consisting of D, alkyl, silyl, germyl, aryl, deuterated alkyl, deuterated silyl, deuterated germyl, and deuterated aryl.

2. The compound of claim 1, wherein $R^1$ is an alkyl group or deuterated alkyl group having 1-30 carbons.

3. The compound of claim 1, wherein a>0 and at least one $R^3$ is alkenylaryl or deuterated alkenylaryl.

4. The compound of claim 3, wherein b>0 and at least one $R^4$ is alkenylaryl or deuterated alkenylaryl.

5. The compound of claim 1, wherein a>0 and b>0.

6. An organic electronic device comprising an anode, a cathode, and at least one organic active layer therebetween, wherein the organic active layer is a photoactive layer which comprises a compound having Formula I as a photoactive material and further comprises a host material

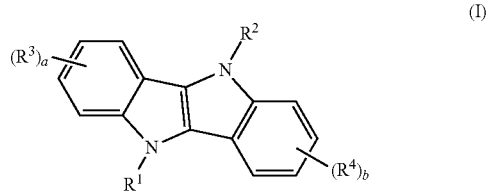

(I)

wherein:

$R^1$ and $R^2$ are the same or different at each occurrence and are selected from the group consisting of alkyl, silyl, germyl, hydrocarbon aryl, N-heteroaryl, O-heteroaryl, S-heteroaryl, N,O-heteroaryl, and deuterated analogs thereof;

$R^3$ and $R^4$ are the same or different at each occurrence and are selected from the group consisting of D, alkyl, alkoxy, silyl, siloxy, siloxane, germyl, aryl, alkenylaryl, aryloxy, heteroaryl, diarylamino, deuterated alkyl, deuterated alkoxy, deuterated silyl, deuterated siloxy, deuterated siloxane, deuterated germyl, deuterated aryl, deuterated alkenylaryl, deuterated aryloxy, deuterated heteroaryl, and deuterated diarylamino;

a and b are the same or different and are an integer from 0-4; and wherein the N-heteroaryl is derived from a compound selected from the group consisting of pyrrole, pyridine, pyrimidine, carbazole, imidazole, benzimidazole, imidazolobenzimidazole, triazole, benzotriazole, triazolopyridine, indole, indolocarbazole, phenanthroline, quinoline, isoquinoline, quinoxaline, substituted derivatives thereof, and deuterated analogs thereof;

wherein the O-heteroaryl is derived from a compound selected from the group consisting of furan, benzofuran, dibenzofuran, substituted derivatives thereof, and deuterated analogs thereof;

wherein the S-heteroaryl is derived from a compound selected form the group consisting of thiophene, benzothiophene, dibenzothiophene, substituted derivatives thereof, and deuterated analogs thereof; and wherein the N,O-heteroaryl is derived from a compound selected from the group consisting of oxazole, benzoxazole, phenoxazine, substituted derivatives thereof, and deuterated analogs thereof;

wherein the substituted derivatives have substituents selected from the group consisting of D, alkyl, silyl, germyl, aryl, deuterated alkyl, deuterated silyl, deuterated germyl, and deuterated aryl.

7. The device of claim 6, wherein the compound having Formula I is selected from the group consisting of Compound I-1 through Compound I-32

Compound I-1

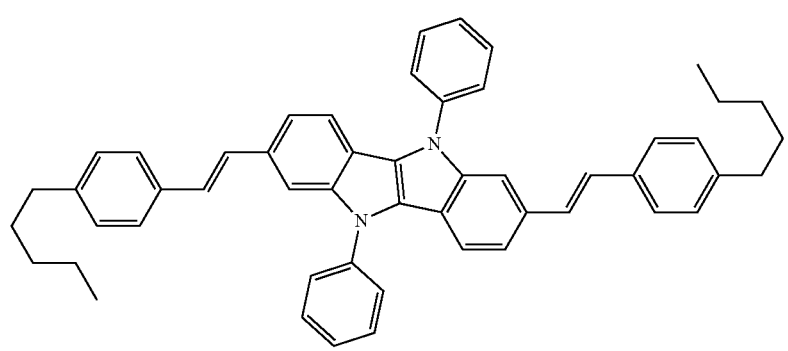

Compound I-2
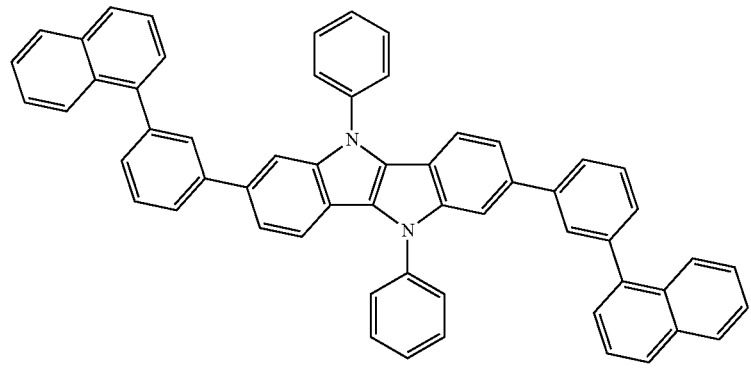
Compound I-3
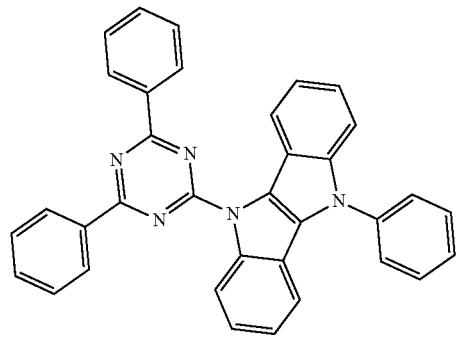
Compound I-4
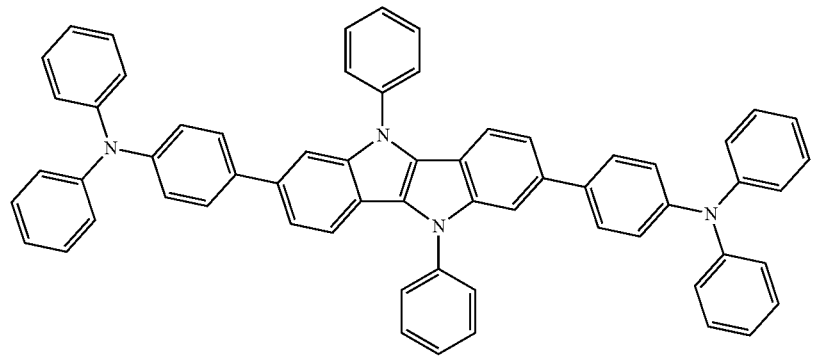
Compound I-5
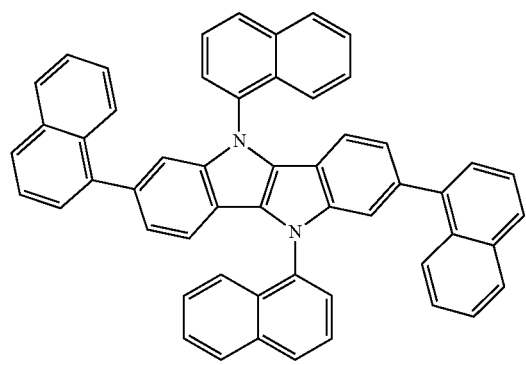
Compound I-6
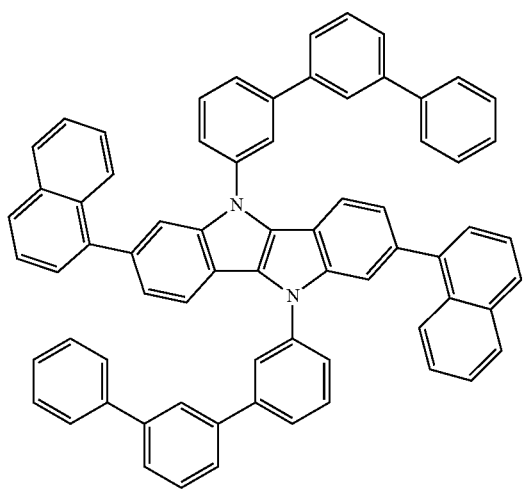

Compound I-7
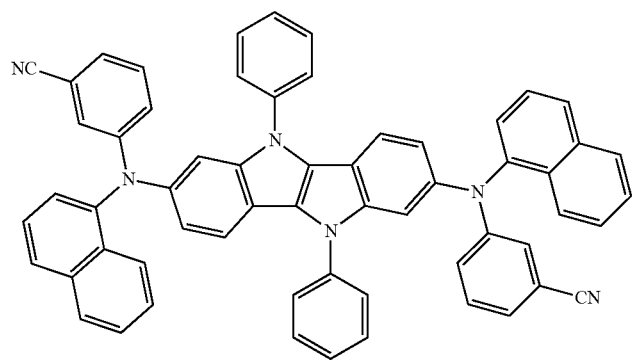
Compound I-8
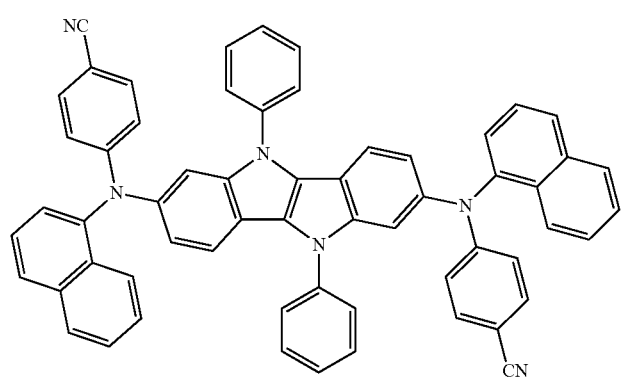
Compound I-9
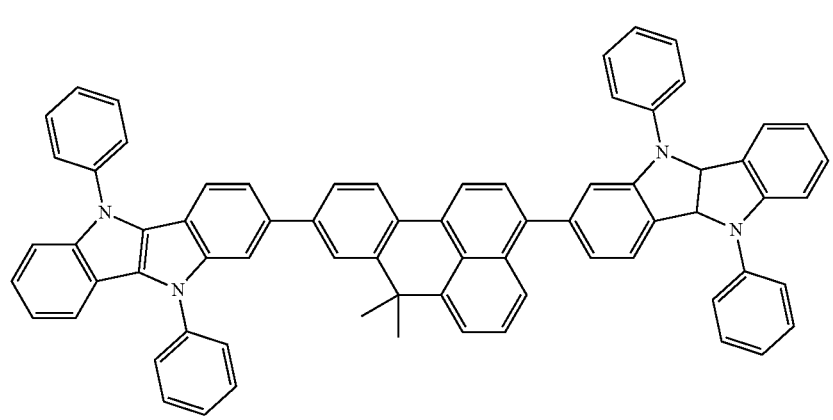
Compound I-10
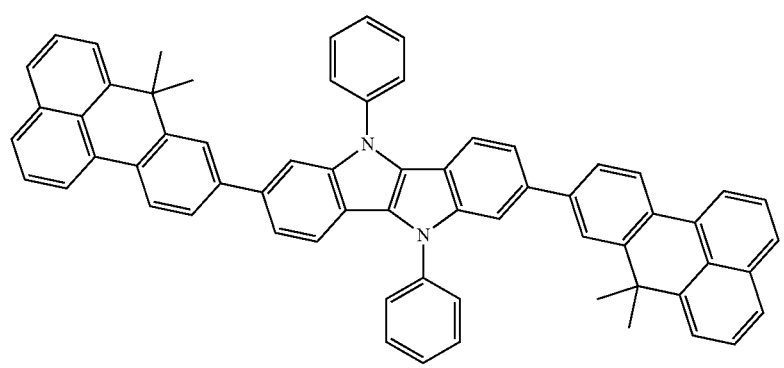

Compound I-11
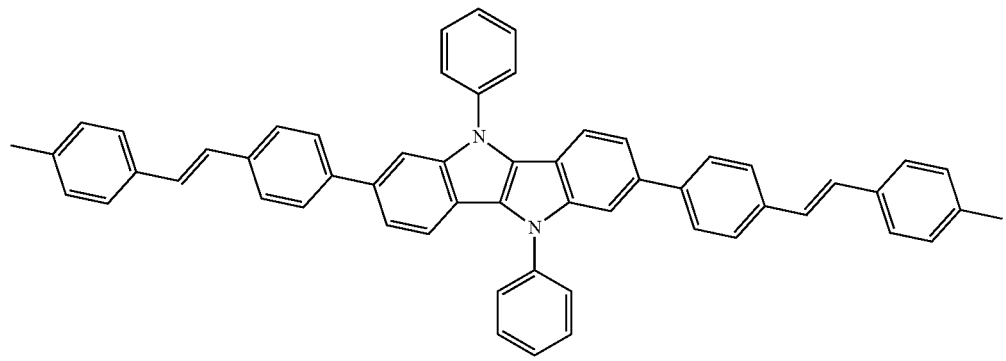
Compound I-12
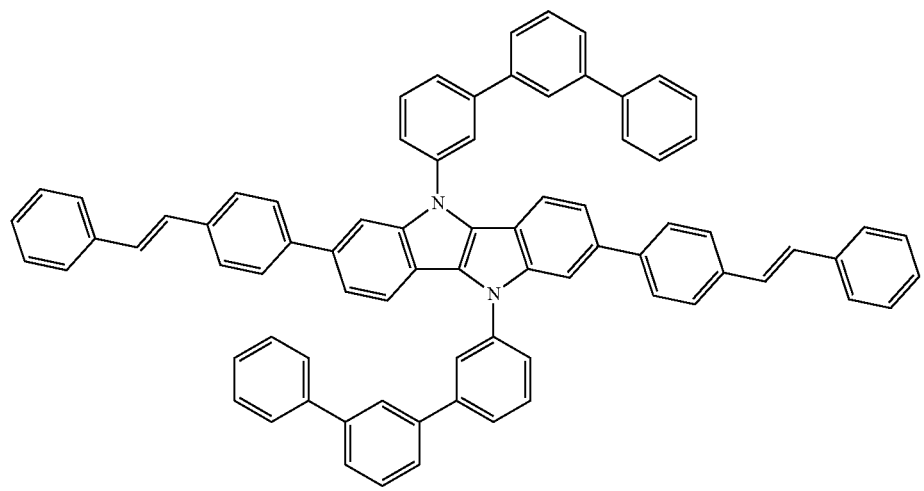
Compound I-13
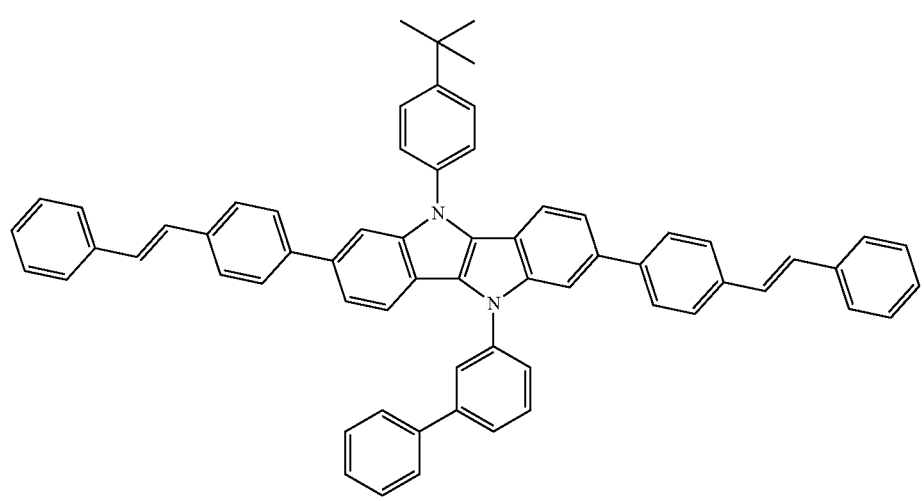

Compound I-14
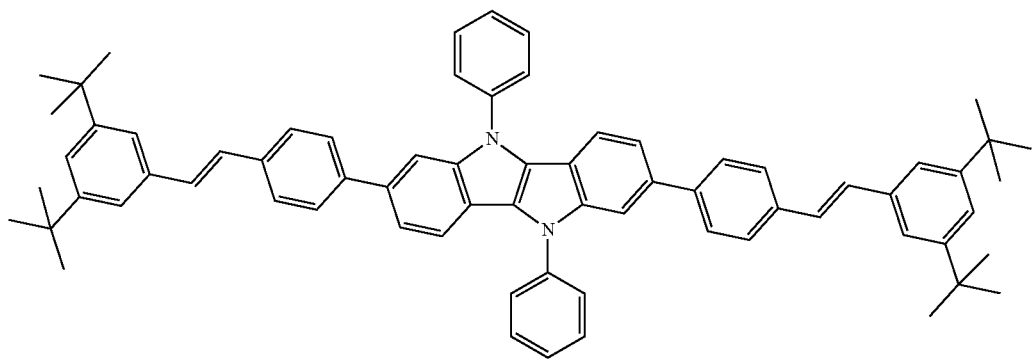
Compound I-15
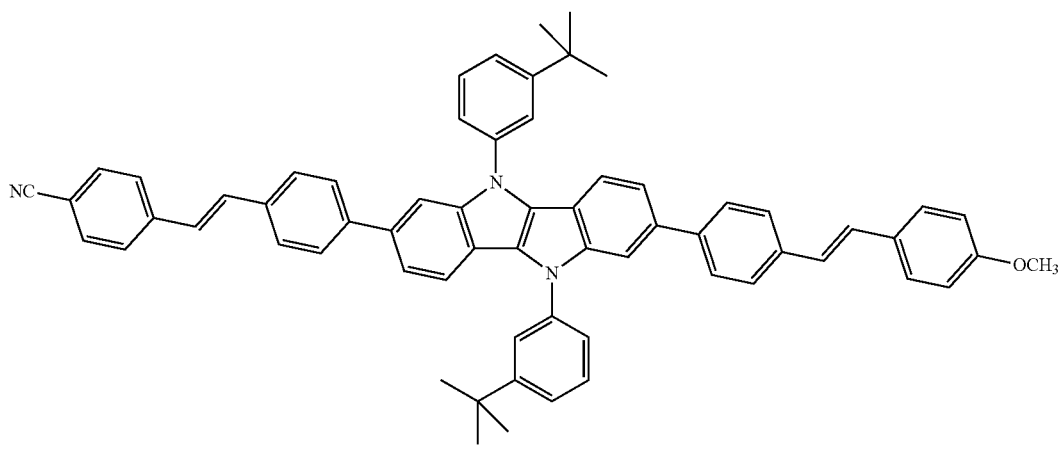
Compound I-16
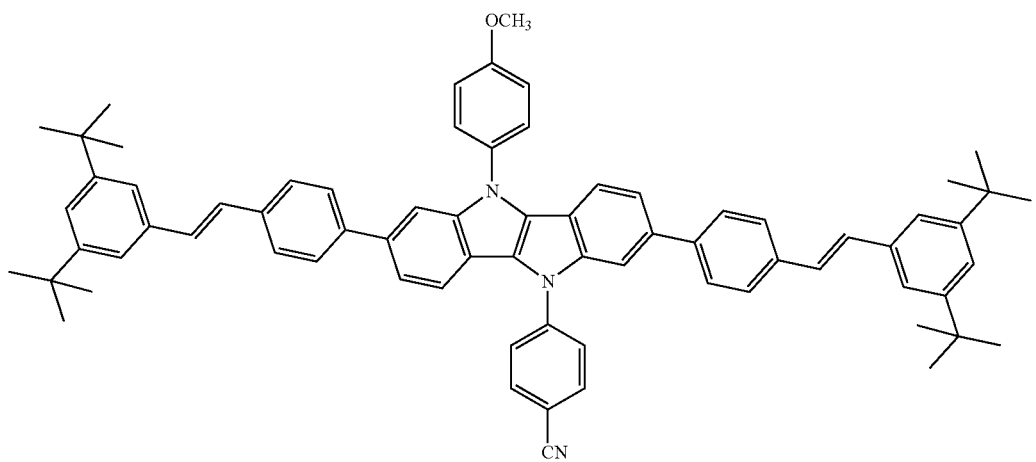
Compound I-17
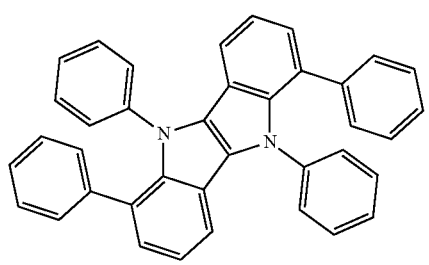

Compound I-18
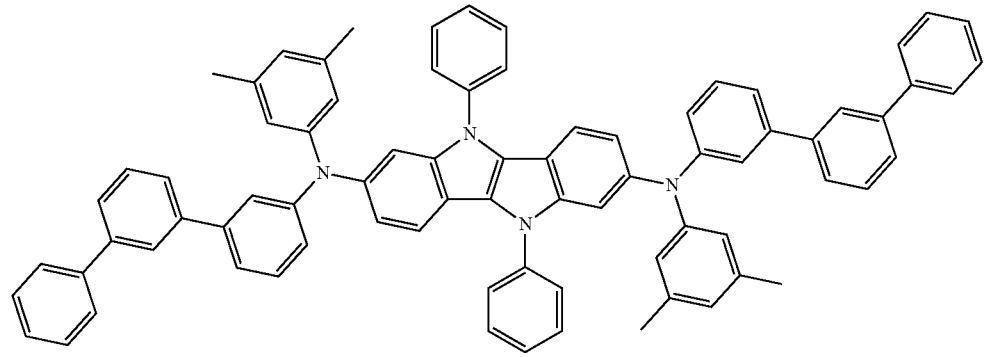
Compound I-19
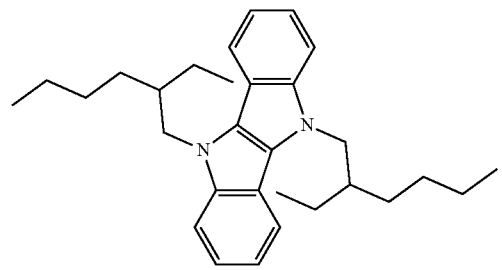
Compound I-20
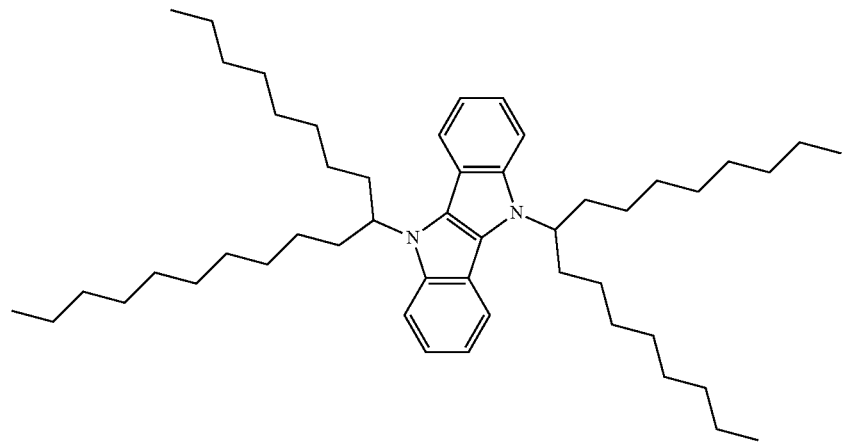
Compound I-21
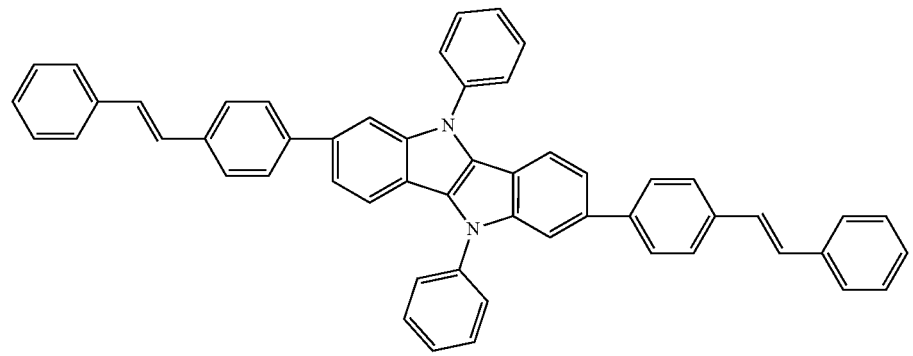

Compound I-22
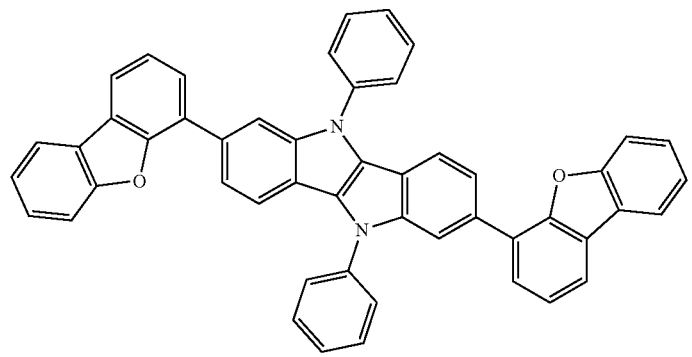
Compound I-23
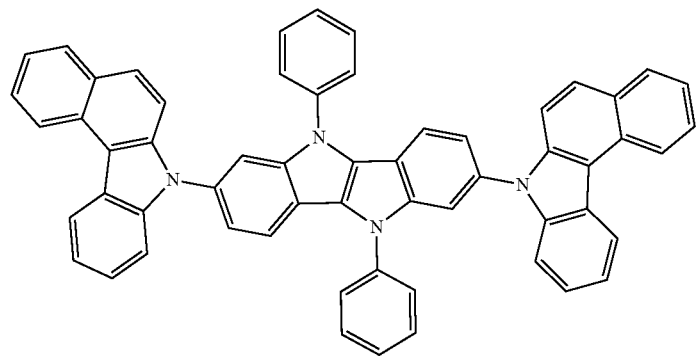
Compound I-24
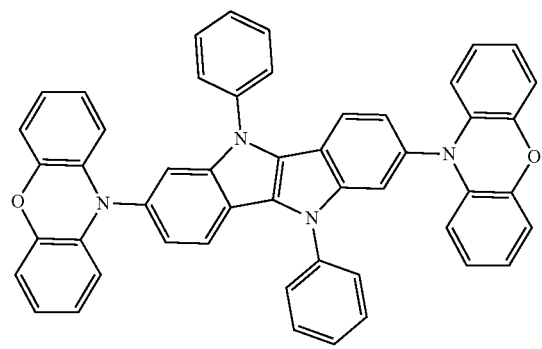
Compound I-25
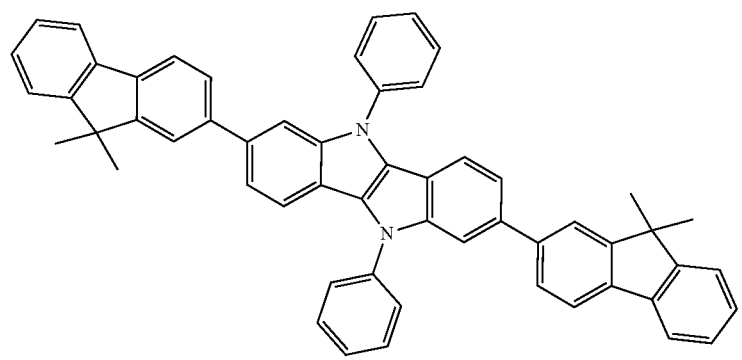

Compound I-26
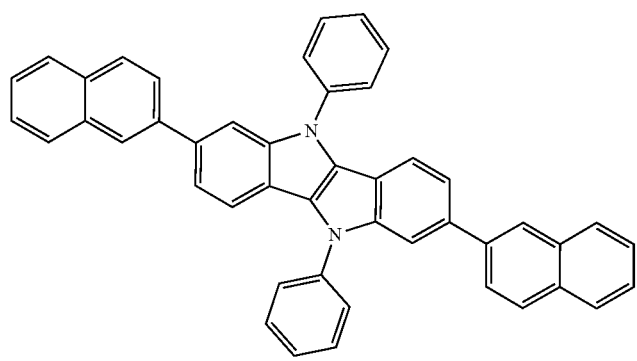
Compound I-27
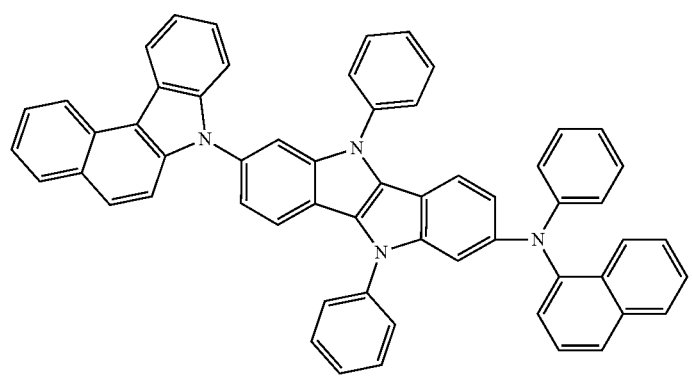
Compound I-28
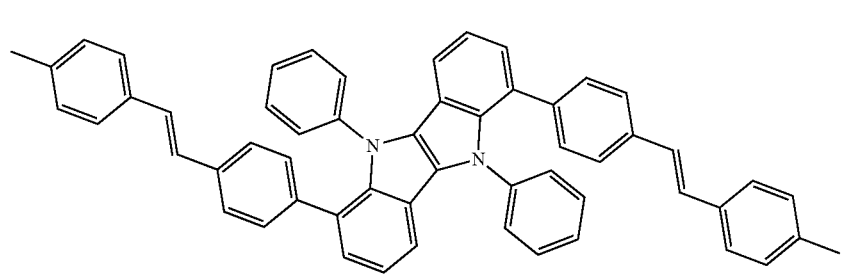
Compound I-29
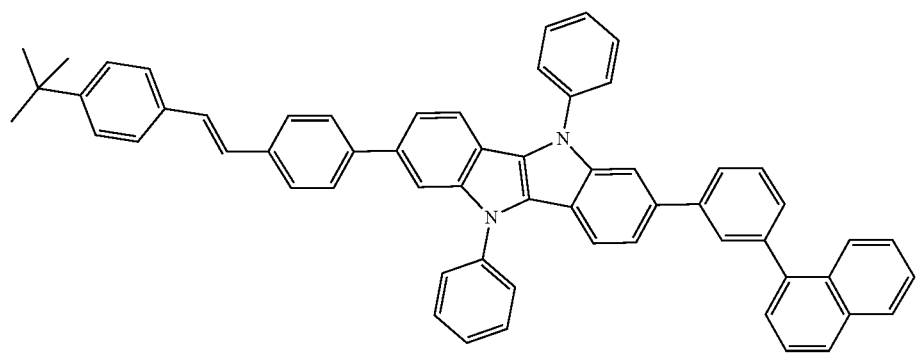

Compound I-30
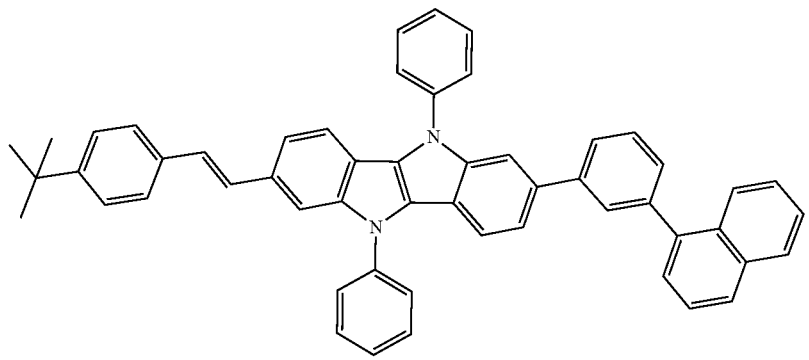
Compound I-31
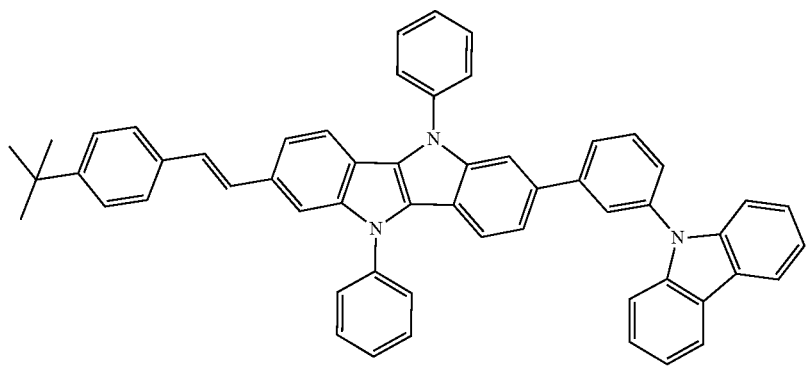
and
Compound I-32
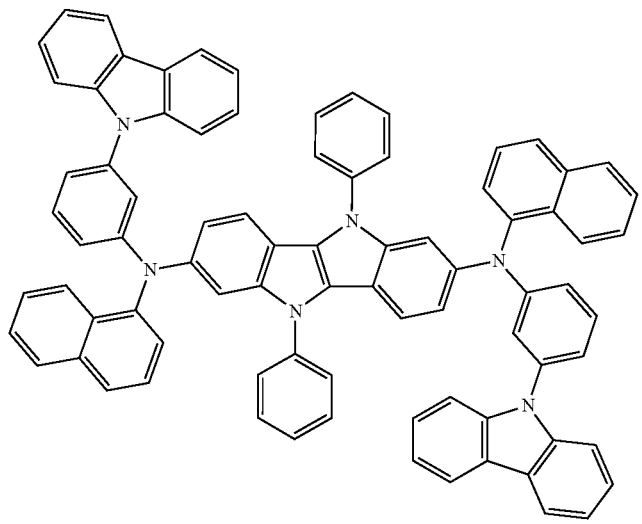
.
8. The device of claim 6, wherein a>0 and b>0.
9. The device of claim 6, wherein $R^1$ has Formula a
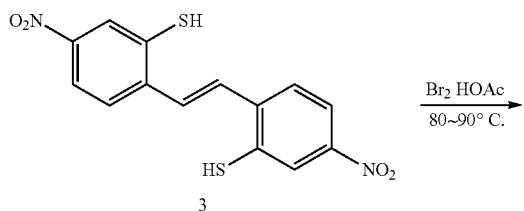
-continued
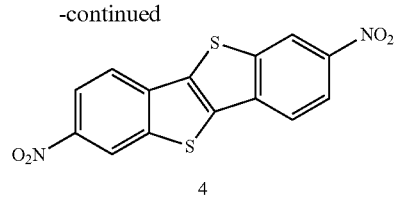
where:
$R^5$ is the same or different at each occurrence and is selected from the group consisting of D, alkyl, alkoxy, siloxane, silyl, germyl, deuterated alkyl, deuterated alkoxy, deuterated siloxane, deuterated silyl, and deuterated germyl, where adjacent $R^5$ groups can be joined together to form an fused aromatic ring or a deuterated fused aromatic ring;

p is the same or different at each occurrence and is an integer from 0-4;

q is an integer from 0-5;

r is an integer from 1 to 5; and

** represents a point of attachment to N.

10. The device of claim 9, wherein $R^2$ has Formula a.

11. The device of claim 6, wherein a>0 and at least one $R^3$ is selected from the group consisting of styryl, stilbenyl, phenyl, naphthyl, Formula a1, substituted derivatives thereof, and deuterated analogs thereof, where Formula a1 is

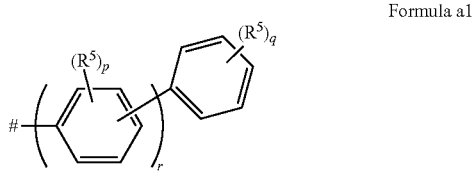

Formula a1 where:

$R^5$ is the same or different at each occurrence and is selected from the group consisting of D, alkyl, alkoxy, siloxane, silyl, germyl, deuterated alkyl, deuterated alkoxy, deuterated siloxane, deuterated silyl, and deu-terated germyl, where adjacent $R^5$ groups can be joined together to form an fused aromatic ring or a deuterated fused aromatic ring;

p is the same or different at each occurrence and is an integer from 0-4;

q is an integer from 0-5;

r is an integer from 1 to 5; and # indicates a point of attachment;

wherein the substituted derivatives have substituents selected from the group consisting of D, CN, alkyl, silyl, germyl, diarylamino, aryl, heteroaryl, deuterated alkyl, deuterated silyl, deuterated germyl, deuterated diarylamino, deuterated aryl, and deuterated heteroaryl.

12. The device of claim 6, wherein a>0 and at least one $R^3$ is an N-heteroaryl group.

13. The compound of claim 6, wherein a=1 and $R^3$ is a diarylamino group or deuterated diarylamino group.

14. The device of claim 13, wherein b=1 and $R^4$ is a diarylamino group or deuterated diarylamino group.

15. The device of claim 6, wherein a>0 and at least one $R^3$ is alkenylaryl or deuterated alkenylaryl.

16. The device of claim 15, wherein b>0 and at least one $R^4$ is alkenylaryl or deuterated alkenylaryl an N-heteroaryl group.

17. A compound selected from the group consisting of Compound I-1, Compound I-11 through Compound I-16, Compound I-21, and Compound I-28 through Compound I-31

Compound I-1

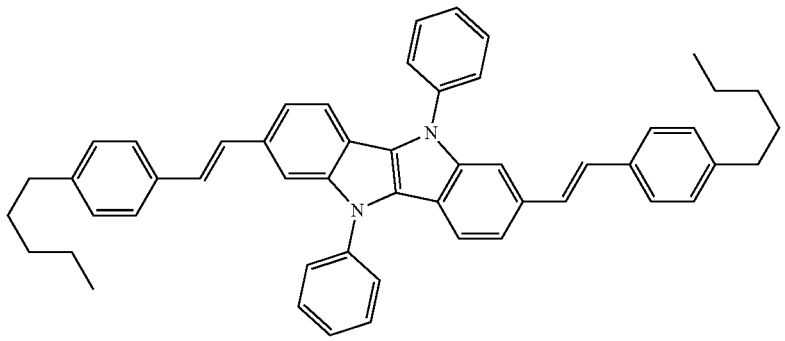

Compound I-11

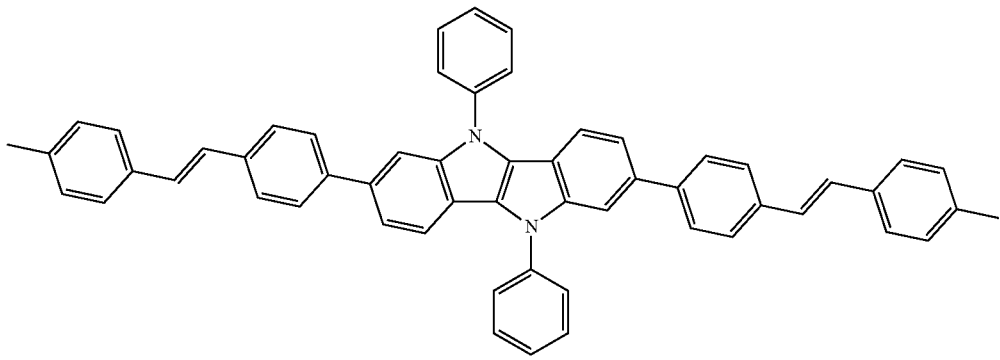

-continued
Compound I-12
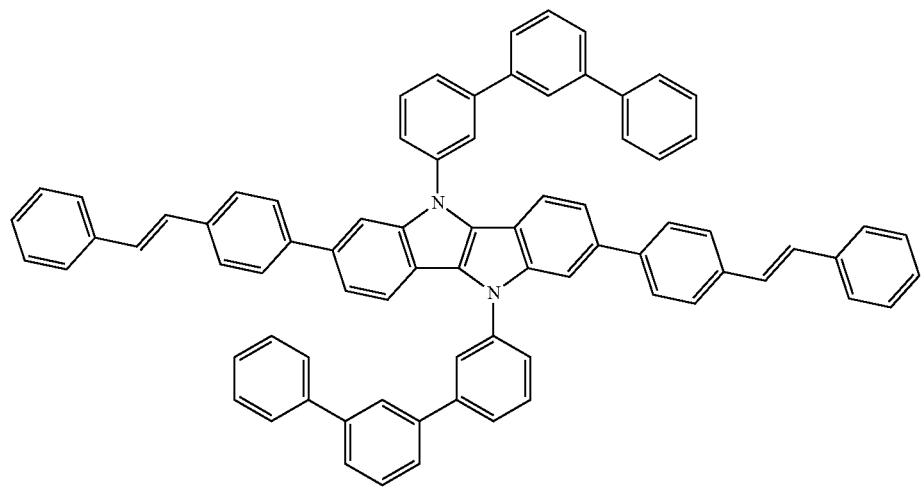
Compound I-13
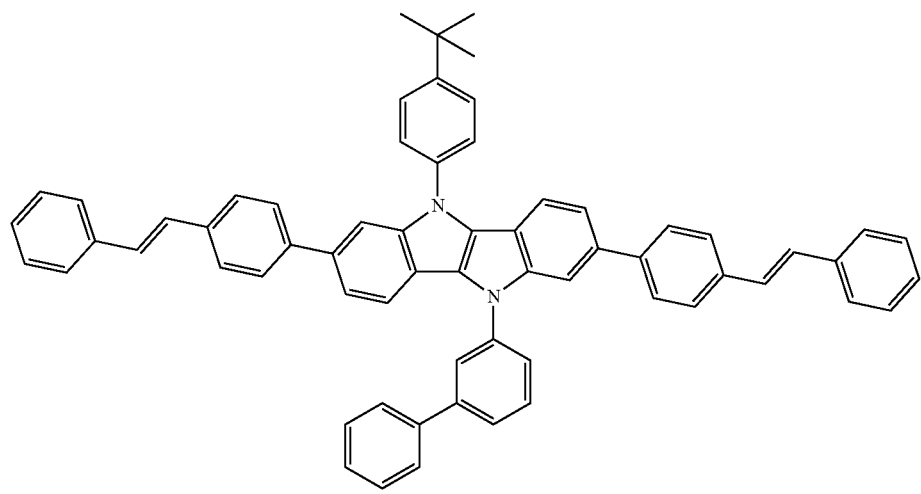
Compound I-14
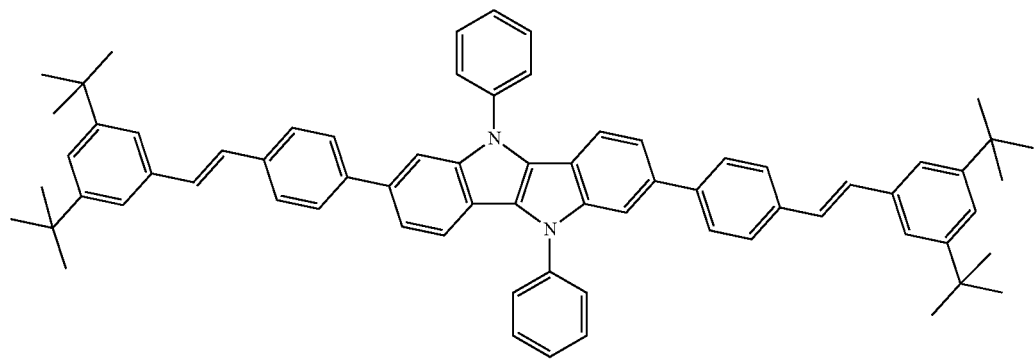

Compound I-15
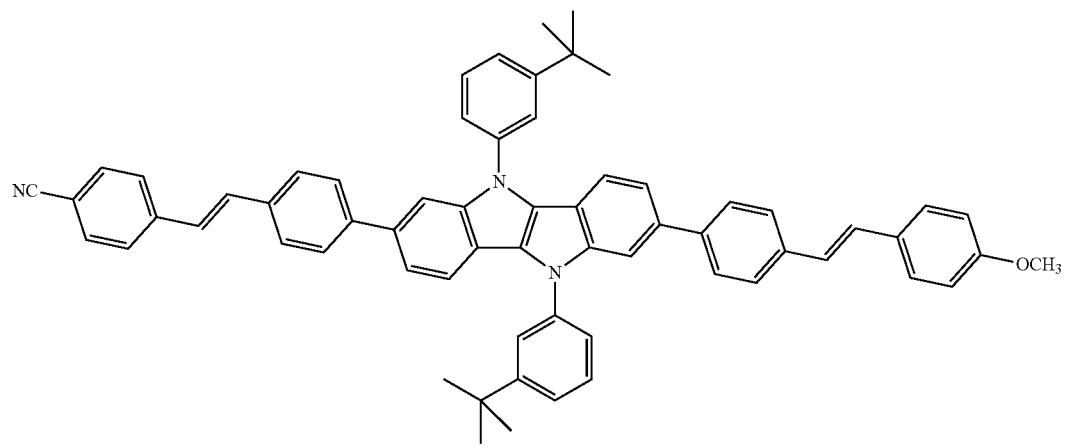
Compound I-16
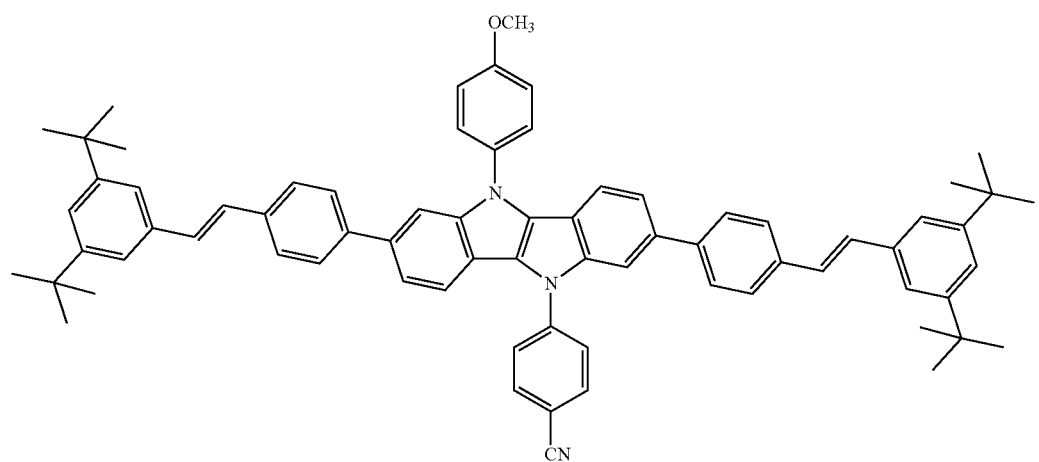
Compound I-21
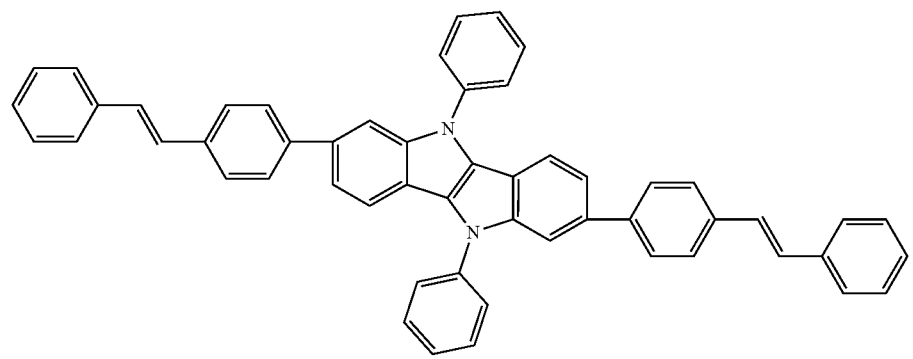
Compound I-28
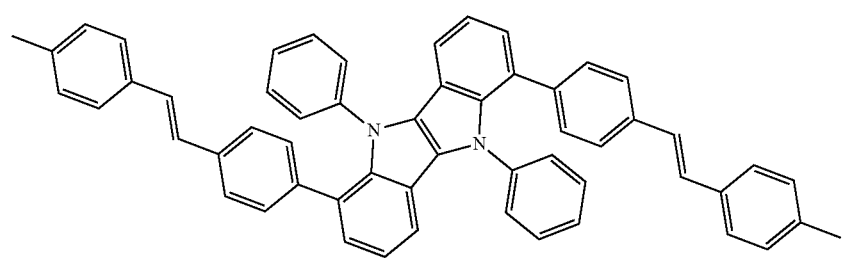

-continued
Compound I-29
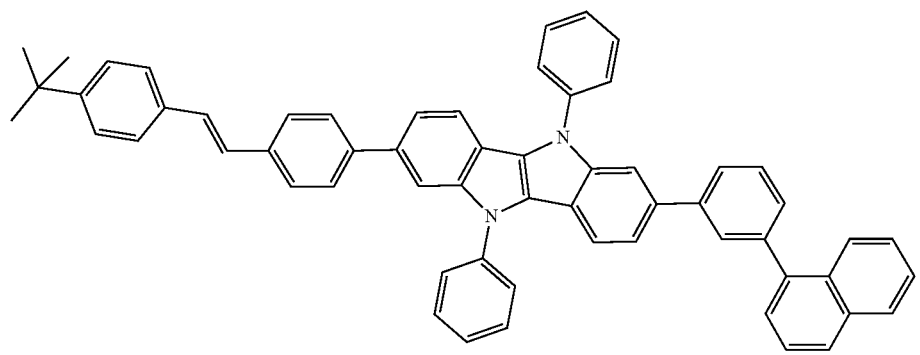
Compound I-30
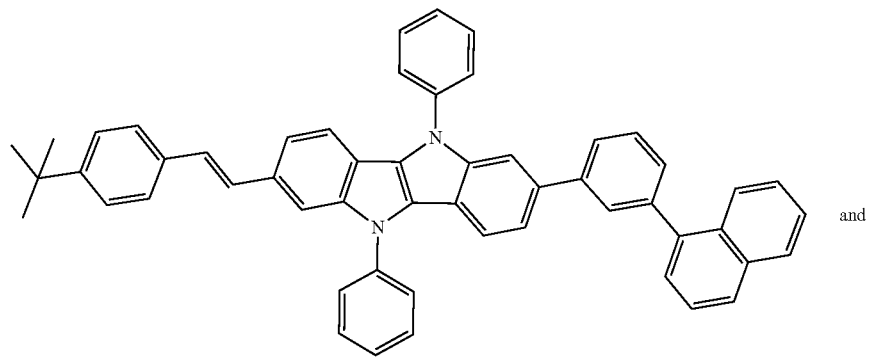
and
Compound I-31
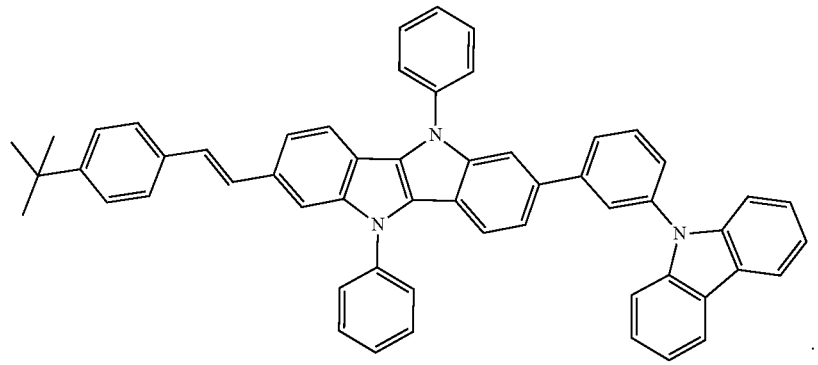
.
* * * * *